United States Patent
Morgan et al.

(10) Patent No.: US 10,638,952 B2
(45) Date of Patent: May 5, 2020

(54) METHODS, SYSTEMS, AND COMPUTER-READABLE MEDIA FOR CALIBRATING AN ELECTROMAGNETIC NAVIGATION SYSTEM

(71) Applicant: COVIDIEN LP, Mansfield, MA (US)

(72) Inventors: Sean M. Morgan, Golden Valley, MN (US); Lev A. Koyrakh, Plymouth, MN (US)

(73) Assignee: COVIDIEN LP, Mansfield, MA (US)

( * ) Notice: Subject to any disclaimer, the term of this patent is extended or adjusted under 35 U.S.C. 154(b) by 683 days.

(21) Appl. No.: 15/337,099

(22) Filed: Oct. 28, 2016

(65) Prior Publication Data

US 2018/0116548 A1    May 3, 2018

(51) Int. Cl.
  *A61B 5/06*    (2006.01)
  *G01C 21/20*   (2006.01)
  *G01C 25/00*   (2006.01)

(52) U.S. Cl.
  CPC .............. *A61B 5/062* (2013.01); *G01C 21/20* (2013.01); *G01C 25/00* (2013.01)

(58) Field of Classification Search
  CPC ......... A61B 5/062; G01C 21/20; G01C 25/00
  USPC .......................................................... 702/95
  See application file for complete search history.

(56) References Cited

U.S. PATENT DOCUMENTS

| | | | |
|---|---|---|---|
| 1,576,781 | A | 3/1926 | Phillips |
| 1,735,726 | A | 11/1929 | Bornhardt |
| 2,407,845 | A | 9/1946 | Nemeyer |
| 2,650,588 | A | 9/1953 | Drew |

(Continued)

FOREIGN PATENT DOCUMENTS

| | | |
|---|---|---|
| CA | 964149 | 3/1975 |
| DE | 3508730 A1 | 9/1986 |

(Continued)

OTHER PUBLICATIONS

Frederick H. Raab, Quasi-Static Magnetic-Field Technique for Determining Position and Orientation, Oct. 1981, IEEE Transactions on Geoscience and Remote Sensing, vol. GE-19, No. 4, pp. 235-243.*

(Continued)

*Primary Examiner* — Eman A Alkafawi

(57) ABSTRACT

Systems, methods, and computer-readable media for calibrating an electromagnetic navigation system are provided. A signal having a first magnitude value and a first phase value is received by way of a receiving antenna. A non-calibrated in-phase component and a non-calibrated quadrature component are computed based on the first magnitude value and the first phase value. A calibrated phase value is computed based on the non-calibrated in-phase component and the non-calibrated quadrature component, and a calibrated in-phase component is computed based on the calibrated phase value, the non-calibrated in-phase component, and the non-calibrated quadrature component. A calibrated quadrature component is computed based on the calibrated phase value, the non-calibrated in-phase component, and the non-calibrated quadrature component, and a calibrated magnitude value is computed based on the calibrated in-phase component. The calibrated phase value and the calibrated magnitude value are stored in a table for use during an electromagnetic navigation procedure.

19 Claims, 18 Drawing Sheets

(2 of 18 Drawing Sheet(s) Filed in Color)

(56) References Cited

U.S. PATENT DOCUMENTS

| | | |
|---|---|---|
| 2,697,433 A | 12/1954 | Sehnder |
| 3,016,899 A | 1/1962 | Stenvall |
| 3,017,887 A | 1/1962 | Heyer |
| 3,061,936 A | 11/1962 | Dobbeleer |
| 3,073,310 A | 1/1963 | Mocarski |
| 3,109,588 A | 11/1963 | Polhemus et al. |
| 3,121,228 A | 2/1964 | Kalmus |
| 3,294,083 A | 12/1966 | Alderson |
| 3,367,326 A | 2/1968 | Frazier |
| 3,439,256 A | 4/1969 | Kahne et al. |
| 3,519,436 A | 7/1970 | Bauer et al. |
| 3,577,160 A | 5/1971 | White |
| 3,600,625 A | 8/1971 | Tsuneta et al. |
| 3,605,725 A | 9/1971 | Bentov |
| 3,614,950 A | 10/1971 | Rabey |
| 3,644,825 A | 2/1972 | Davis, Jr. et al. |
| 3,674,014 A | 7/1972 | Tillander |
| 3,702,935 A | 11/1972 | Carey et al. |
| 3,704,707 A | 12/1972 | Halloran |
| 3,821,469 A | 6/1974 | Whetstone et al. |
| 3,822,697 A | 7/1974 | Komiya |
| 3,868,565 A | 2/1975 | Kuipers |
| 3,941,127 A | 3/1976 | Froning |
| 3,983,474 A | 9/1976 | Kuipers |
| 4,017,858 A | 4/1977 | Kuipers |
| 4,037,592 A | 7/1977 | Kronner |
| 4,052,620 A | 10/1977 | Brunnett |
| 4,054,881 A | 10/1977 | Raab |
| 4,117,337 A | 9/1978 | Staats |
| 4,135,184 A | 1/1979 | Pruzick |
| 4,173,228 A | 11/1979 | Van Steenwyk et al. |
| 4,182,312 A | 1/1980 | Mushabac |
| 4,202,349 A | 5/1980 | Jones |
| 4,228,799 A | 10/1980 | Anichkov et al. |
| 4,249,167 A | 2/1981 | Purinton et al. |
| 4,256,112 A | 3/1981 | Kopf et al. |
| 4,262,306 A | 4/1981 | Renner |
| 4,287,809 A | 9/1981 | Egli et al. |
| 4,298,874 A | 11/1981 | Kuipers |
| 4,308,530 A | 12/1981 | Kip et al. |
| 4,314,251 A | 2/1982 | Raab |
| 4,317,078 A | 2/1982 | Weed et al. |
| 4,319,136 A | 3/1982 | Jinkins |
| 4,328,548 A | 5/1982 | Crow et al. |
| 4,328,813 A | 5/1982 | Ray |
| 4,339,953 A | 7/1982 | Iwasaki |
| 4,341,220 A | 7/1982 | Perry |
| 4,341,385 A | 7/1982 | Doyle et al. |
| 4,346,384 A | 8/1982 | Raab |
| 4,358,856 A | 11/1982 | Stivender et al. |
| 4,368,536 A | 1/1983 | Pfeiler |
| 4,394,831 A | 7/1983 | Egli et al. |
| 4,396,885 A | 8/1983 | Constant |
| 4,396,945 A | 8/1983 | DiMatteo et al. |
| 4,403,321 A | 9/1983 | Kruger |
| 4,418,422 A | 11/1983 | Richter et al. |
| 4,419,012 A | 12/1983 | Stephenson et al. |
| 4,422,041 A | 12/1983 | Lienau |
| 4,425,511 A | 1/1984 | Brosh |
| 4,431,005 A | 2/1984 | McCormick |
| 4,447,224 A | 5/1984 | DeCant, Jr. et al. |
| 4,447,462 A | 5/1984 | Tafuri et al. |
| 4,485,815 A | 12/1984 | Amplatz et al. |
| 4,506,676 A | 3/1985 | Duska |
| 4,543,959 A | 10/1985 | Sepponen |
| 4,548,208 A | 10/1985 | Niemi |
| 4,571,834 A | 2/1986 | Fraser et al. |
| 4,572,198 A | 2/1986 | Codrington |
| 4,583,538 A | 4/1986 | Onik et al. |
| 4,584,577 A | 4/1986 | Temple |
| 4,586,491 A | 5/1986 | Carpenter |
| 4,587,975 A | 5/1986 | Salo et al. |
| 4,608,977 A | 9/1986 | Brown |
| 4,613,866 A | 9/1986 | Blood |
| 4,617,925 A | 10/1986 | Laitinen |
| 4,618,978 A | 10/1986 | Cosman |
| 4,621,628 A | 11/1986 | Brudermann |
| 4,625,718 A | 12/1986 | Olerud et al. |
| 4,638,798 A | 1/1987 | Shelden et al. |
| 4,642,786 A | 2/1987 | Hansen |
| 4,645,343 A | 2/1987 | Stockdale et al. |
| 4,649,504 A | 3/1987 | Krouglicof et al. |
| 4,651,732 A | 3/1987 | Frederick |
| 4,653,509 A | 3/1987 | Oloff et al. |
| 4,659,971 A | 4/1987 | Suzuki et al. |
| 4,660,970 A | 4/1987 | Ferrano |
| 4,673,352 A | 6/1987 | Hansen |
| 4,686,695 A | 8/1987 | Macovski |
| 4,688,037 A | 8/1987 | Krieg |
| 4,696,544 A | 9/1987 | Costella |
| 4,697,595 A | 10/1987 | Breyer et al. |
| 4,701,049 A | 10/1987 | Beckman et al. |
| 4,704,602 A | 11/1987 | Asbrink |
| 4,705,395 A | 11/1987 | Hageniers |
| 4,705,401 A | 11/1987 | Addleman et al. |
| 4,706,665 A | 11/1987 | Gouda |
| 4,709,156 A | 11/1987 | Murphy et al. |
| 4,710,708 A | 12/1987 | Rorden et al. |
| 4,719,419 A | 1/1988 | Dawley |
| 4,722,056 A | 1/1988 | Roberts et al. |
| 4,722,336 A | 2/1988 | Kim et al. |
| 4,723,544 A | 2/1988 | Moore et al. |
| 4,726,355 A | 2/1988 | Okada |
| 4,727,565 A | 2/1988 | Ericson |
| RE32,619 E | 3/1988 | Damadian |
| 4,733,969 A | 3/1988 | Case et al. |
| 4,737,032 A | 4/1988 | Addleman et al. |
| 4,737,794 A | 4/1988 | Jones |
| 4,737,921 A | 4/1988 | Goldwasser et al. |
| 4,742,356 A | 5/1988 | Kuipers |
| 4,742,815 A | 5/1988 | Ninan et al. |
| 4,743,770 A | 5/1988 | Lee |
| 4,743,771 A | 5/1988 | Sacks et al. |
| 4,745,290 A | 5/1988 | Frankel et al. |
| 4,750,487 A | 6/1988 | Zanetti |
| 4,753,528 A | 6/1988 | Hines et al. |
| 4,761,072 A | 8/1988 | Pryor |
| 4,764,016 A | 8/1988 | Johansson |
| 4,771,787 A | 9/1988 | Wurster et al. |
| 4,779,212 A | 10/1988 | Levy |
| 4,782,239 A | 11/1988 | Hirose et al. |
| 4,784,117 A | 11/1988 | Miyazaki |
| 4,788,481 A | 11/1988 | Niwa |
| 4,791,934 A | 12/1988 | Brunnett |
| 4,793,355 A | 12/1988 | Crum et al. |
| 4,794,262 A | 12/1988 | Sato et al. |
| 4,797,907 A | 1/1989 | Anderton |
| 4,803,976 A | 2/1989 | Frigg et al. |
| 4,804,261 A | 2/1989 | Kirschen |
| 4,805,615 A | 2/1989 | Carol |
| 4,809,694 A | 3/1989 | Ferrara |
| 4,821,200 A | 4/1989 | Oberg |
| 4,821,206 A | 4/1989 | Arora |
| 4,821,731 A | 4/1989 | Martinelli et al. |
| 4,822,163 A | 4/1989 | Schmidt |
| 4,825,091 A | 4/1989 | Breyer et al. |
| 4,829,250 A | 5/1989 | Rotier |
| 4,829,373 A | 5/1989 | Leberl et al. |
| 4,836,778 A | 6/1989 | Baumrind et al. |
| 4,838,265 A | 6/1989 | Cosman et al. |
| 4,841,967 A | 6/1989 | Chang et al. |
| 4,845,771 A | 7/1989 | Wislocki et al. |
| 4,849,692 A | 7/1989 | Blood |
| 4,860,331 A | 8/1989 | Williams et al. |
| 4,862,893 A | 9/1989 | Martinelli |
| 4,869,247 A | 9/1989 | Howard, III et al. |
| 4,875,165 A | 10/1989 | Fencil et al. |
| 4,875,478 A | 10/1989 | Chen |
| 4,884,566 A | 12/1989 | Mountz et al. |
| 4,889,526 A | 12/1989 | Rauscher et al. |
| 4,896,673 A | 1/1990 | Rose et al. |
| 4,905,698 A | 3/1990 | Strohl, Jr. et al. |
| 4,923,459 A | 5/1990 | Nambu |
| 4,931,056 A | 6/1990 | Ghajar et al. |

(56) References Cited

U.S. PATENT DOCUMENTS

| | | |
|---|---|---|
| 4,945,305 A | 7/1990 | Blood |
| 4,945,912 A | 8/1990 | Langberg |
| 4,945,914 A | 8/1990 | Allen |
| 4,951,653 A | 8/1990 | Fry et al. |
| 4,955,891 A | 9/1990 | Carol |
| 4,961,422 A | 10/1990 | Marchosky et al. |
| 4,977,655 A | 12/1990 | Martinelli |
| 4,989,608 A | 2/1991 | Ratner |
| 4,991,579 A | 2/1991 | Allen |
| 5,002,058 A | 3/1991 | Martinelli |
| 5,005,592 A | 4/1991 | Cartmell |
| 5,013,047 A | 5/1991 | Schwab |
| 5,013,317 A | 5/1991 | Cole et al. |
| 5,016,639 A | 5/1991 | Allen |
| 5,017,139 A | 5/1991 | Mushabac |
| 5,023,102 A | 6/1991 | Given, Jr. |
| 5,027,818 A | 7/1991 | Bova et al. |
| 5,030,196 A | 7/1991 | Inoue |
| 5,030,222 A | 7/1991 | Calandruccio et al. |
| 5,031,203 A | 7/1991 | Trecha |
| RE33,662 E | 8/1991 | Blair et al. |
| 5,042,486 A | 8/1991 | Pfeiler et al. |
| 5,047,036 A | 9/1991 | Koutrouvelis |
| 5,050,608 A | 9/1991 | Watanabe et al. |
| 5,054,492 A | 10/1991 | Scribner et al. |
| 5,057,095 A | 10/1991 | Fabian |
| 5,059,789 A | 10/1991 | Salcudean |
| 5,070,462 A | 12/1991 | Chau |
| 5,078,140 A | 1/1992 | Kwoh |
| 5,079,699 A | 1/1992 | Tuy et al. |
| 5,082,286 A | 1/1992 | Ryan et al. |
| 5,086,401 A | 2/1992 | Glassman et al. |
| 5,088,928 A | 2/1992 | Chan |
| 5,094,241 A | 3/1992 | Allen |
| 5,097,839 A | 3/1992 | Allen |
| 5,098,426 A | 3/1992 | Sklar et al. |
| 5,099,845 A | 3/1992 | Besz et al. |
| 5,099,846 A | 3/1992 | Hardy |
| 5,104,393 A | 4/1992 | Isner et al. |
| 5,105,829 A | 4/1992 | Fabian et al. |
| 5,107,839 A | 4/1992 | Houdek et al. |
| 5,107,843 A | 4/1992 | Aarnio et al. |
| 5,107,862 A | 4/1992 | Fabian et al. |
| 5,109,194 A | 4/1992 | Cantaloube |
| 5,119,817 A | 6/1992 | Allen |
| 5,127,408 A | 7/1992 | Parsons et al. |
| 5,129,654 A | 7/1992 | Bogner |
| 5,142,930 A | 9/1992 | Allen et al. |
| 5,143,076 A | 9/1992 | Hardy et al. |
| 5,152,277 A | 10/1992 | Honda et al. |
| 5,152,288 A | 10/1992 | Hoenig et al. |
| 5,160,337 A | 11/1992 | Cosman |
| 5,161,536 A | 11/1992 | Vilkomerson et al. |
| 5,178,130 A | 1/1993 | Kaiya |
| 5,178,164 A | 1/1993 | Allen |
| 5,178,621 A | 1/1993 | Cook et al. |
| 5,186,174 A | 2/1993 | Schlondorff et al. |
| 5,187,475 A | 2/1993 | Wagener et al. |
| 5,188,126 A | 2/1993 | Fabian et al. |
| 5,188,368 A | 2/1993 | Ryan |
| 5,190,059 A | 3/1993 | Fabian et al. |
| 5,190,285 A | 3/1993 | Levy et al. |
| 5,193,106 A | 3/1993 | DeSena |
| 5,196,928 A | 3/1993 | Karasawa et al. |
| 5,197,476 A | 3/1993 | Nowacki et al. |
| 5,197,965 A | 3/1993 | Cherry et al. |
| 5,198,768 A | 3/1993 | Keren |
| 5,198,877 A | 3/1993 | Schulz |
| 5,203,337 A | 4/1993 | Feldman |
| 5,207,688 A | 5/1993 | Carol |
| 5,211,164 A | 5/1993 | Allen |
| 5,211,165 A | 5/1993 | Dumoulin et al. |
| 5,211,176 A | 5/1993 | Ishiguro et al. |
| 5,212,720 A | 5/1993 | Landi et al. |
| 5,214,615 A | 5/1993 | Bauer |
| 5,219,351 A | 6/1993 | Teubner et al. |
| 5,222,499 A | 6/1993 | Allen et al. |
| 5,224,049 A | 6/1993 | Mushabac |
| 5,228,442 A | 7/1993 | Imran |
| 5,230,338 A | 7/1993 | Allen et al. |
| 5,230,623 A | 7/1993 | Guthrie et al. |
| 5,233,990 A | 8/1993 | Barnea |
| 5,237,996 A | 8/1993 | Waldman et al. |
| 5,249,581 A | 10/1993 | Horbal et al. |
| 5,251,127 A | 10/1993 | Raab |
| 5,251,635 A | 10/1993 | Dumoulin et al. |
| 5,253,647 A | 10/1993 | Takahashi et al. |
| 5,255,680 A | 10/1993 | Darrow et al. |
| 5,257,636 A | 11/1993 | White |
| 5,257,998 A | 11/1993 | Ota et al. |
| 5,261,404 A | 11/1993 | Mick et al. |
| 5,262,722 A | 11/1993 | Hedengren et al. |
| 5,265,610 A | 11/1993 | Darrow et al. |
| 5,265,611 A | 11/1993 | Hoenig et al. |
| 5,269,759 A | 12/1993 | Hernandez et al. |
| 5,271,400 A | 12/1993 | Dumoulin et al. |
| 5,273,025 A | 12/1993 | Sakiyama et al. |
| 5,274,551 A | 12/1993 | Corby, Jr. |
| 5,279,309 A | 1/1994 | Taylor et al. |
| 5,285,787 A | 2/1994 | Machida |
| 5,291,199 A | 3/1994 | Overman et al. |
| 5,291,889 A | 3/1994 | Kenet et al. |
| 5,295,483 A | 3/1994 | Nowacki et al. |
| 5,297,549 A | 3/1994 | Beatty et al. |
| 5,299,253 A | 3/1994 | Wessels |
| 5,299,254 A | 3/1994 | Dancer et al. |
| 5,299,288 A | 3/1994 | Glassman et al. |
| 5,300,080 A | 4/1994 | Clayman et al. |
| 5,301,061 A | 4/1994 | Nakada et al. |
| 5,305,091 A | 4/1994 | Gelbart et al. |
| 5,305,203 A | 4/1994 | Raab |
| 5,306,271 A | 4/1994 | Zinreich et al. |
| 5,307,072 A * | 4/1994 | Jones, Jr. ............... F41G 3/08 324/244 |
| 5,307,816 A | 5/1994 | Hashimoto et al. |
| 5,309,913 A | 5/1994 | Kormos et al. |
| 5,315,630 A | 5/1994 | Sturm et al. |
| 5,316,024 A | 5/1994 | Hirschi et al. |
| 5,318,025 A | 6/1994 | Dumoulin et al. |
| 5,320,111 A | 6/1994 | Livingston |
| 5,325,728 A | 7/1994 | Zimmerman et al. |
| 5,325,873 A | 7/1994 | Hirschi et al. |
| 5,327,889 A | 7/1994 | Imran |
| 5,329,944 A | 7/1994 | Fabian et al. |
| 5,330,485 A | 7/1994 | Clayman et al. |
| 5,333,168 A | 7/1994 | Fernandes et al. |
| 5,341,807 A | 8/1994 | Nardella |
| 5,347,289 A | 9/1994 | Elhardt |
| 5,353,795 A | 10/1994 | Souza et al. |
| 5,353,800 A | 10/1994 | Pohndorf et al. |
| 5,353,807 A | 10/1994 | DeMarco |
| 5,357,253 A | 10/1994 | Van Etten et al. |
| 5,359,417 A | 10/1994 | Muller et al. |
| 5,368,030 A | 11/1994 | Zinreich et al. |
| 5,371,778 A | 12/1994 | Yanof et al. |
| 5,375,596 A | 12/1994 | Twiss et al. |
| 5,376,795 A | 12/1994 | Hasegawa et al. |
| 5,377,678 A | 1/1995 | Dumoulin et al. |
| 5,383,454 A | 1/1995 | Bucholz |
| 5,383,852 A | 1/1995 | Stevens-Wright |
| 5,385,146 A | 1/1995 | Goldreyer |
| 5,385,148 A | 1/1995 | Lesh et al. |
| 5,386,828 A | 2/1995 | Owens et al. |
| 5,389,073 A | 2/1995 | Imran |
| 5,389,101 A | 2/1995 | Heilbrun et al. |
| 5,391,199 A | 2/1995 | Ben-Haim |
| 5,394,457 A | 2/1995 | Leibinger et al. |
| 5,394,875 A | 3/1995 | Lewis et al. |
| 5,397,321 A | 3/1995 | Houser et al. |
| 5,397,329 A | 3/1995 | Allen |
| 5,398,684 A | 3/1995 | Hardy |
| 5,398,691 A | 3/1995 | Martin et al. |
| 5,399,146 A | 3/1995 | Nowacki et al. |
| 5,400,384 A | 3/1995 | Fernandes et al. |

(56) References Cited

U.S. PATENT DOCUMENTS

| | | |
|---|---|---|
| 5,400,771 A | 3/1995 | Pirak et al. |
| 5,402,801 A | 4/1995 | Taylor |
| 5,405,346 A | 4/1995 | Grundy et al. |
| 5,408,409 A | 4/1995 | Glassman et al. |
| 5,409,000 A | 4/1995 | Imran |
| 5,412,414 A | 5/1995 | Ast et al. |
| 5,413,573 A | 5/1995 | Koivukangas |
| 5,417,210 A | 5/1995 | Funda et al. |
| 5,419,325 A | 5/1995 | Dumoulin et al. |
| 5,423,334 A | 6/1995 | Jordan |
| 5,425,367 A | 6/1995 | Shapiro et al. |
| 5,425,382 A | 6/1995 | Golden et al. |
| 5,426,683 A | 6/1995 | O'Farrell, Jr. et al. |
| 5,426,687 A | 6/1995 | Goodall et al. |
| 5,427,097 A | 6/1995 | Depp |
| 5,429,132 A | 7/1995 | Guy et al. |
| 5,433,198 A | 7/1995 | Desai |
| 5,435,573 A | 7/1995 | Oakford |
| RE35,025 E | 8/1995 | Anderton |
| 5,437,277 A | 8/1995 | Dumoulin et al. |
| 5,443,066 A | 8/1995 | Dumoulin et al. |
| 5,443,489 A | 8/1995 | Ben-Haim |
| 5,444,756 A | 8/1995 | Pai et al. |
| 5,445,144 A | 8/1995 | Wodicka et al. |
| 5,445,150 A | 8/1995 | Dumoulin et al. |
| 5,445,166 A | 8/1995 | Taylor |
| 5,446,548 A | 8/1995 | Gerig et al. |
| 5,447,154 A | 9/1995 | Cinquin et al. |
| 5,447,156 A | 9/1995 | Dumoulin et al. |
| 5,448,610 A | 9/1995 | Yamamoto et al. |
| 5,453,686 A | 9/1995 | Anderson |
| 5,456,254 A | 10/1995 | Pietroski et al. |
| 5,456,664 A | 10/1995 | Heinzelman et al. |
| 5,456,689 A | 10/1995 | Kresch et al. |
| 5,456,718 A | 10/1995 | Szymaitis |
| 5,457,641 A | 10/1995 | Zimmer et al. |
| 5,458,718 A | 10/1995 | Venkitachalam |
| 5,464,446 A | 11/1995 | Dreessen et al. |
| 5,469,847 A | 11/1995 | Zinreich et al. |
| 5,472,441 A | 12/1995 | Edwards et al. |
| 5,476,100 A | 12/1995 | Galel |
| 5,476,495 A | 12/1995 | Kordis et al. |
| 5,478,341 A | 12/1995 | Cook et al. |
| 5,478,343 A | 12/1995 | Ritter |
| 5,480,422 A | 1/1996 | Ben-Haim |
| 5,480,439 A | 1/1996 | Bisek et al. |
| 5,483,961 A | 1/1996 | Kelly et al. |
| 5,485,849 A | 1/1996 | Panescu et al. |
| 5,487,391 A | 1/1996 | Panescu |
| 5,487,729 A | 1/1996 | Avellanet et al. |
| 5,487,757 A | 1/1996 | Truckai et al. |
| 5,489,256 A | 2/1996 | Adair |
| 5,490,196 A | 2/1996 | Rudich et al. |
| 5,492,131 A | 2/1996 | Galel |
| 5,492,713 A | 2/1996 | Sommermeyer |
| 5,493,517 A | 2/1996 | Frazier |
| 5,494,034 A | 2/1996 | Schlondorff et al. |
| 5,503,416 A | 4/1996 | Aoki et al. |
| 5,513,637 A | 5/1996 | Twiss et al. |
| 5,514,146 A | 5/1996 | Lam et al. |
| 5,515,160 A | 5/1996 | Schulz et al. |
| 5,515,853 A | 5/1996 | Smith et al. |
| 5,517,990 A | 5/1996 | Kalfas et al. |
| 5,520,059 A | 5/1996 | Garshelis |
| 5,522,814 A | 6/1996 | Bemaz |
| 5,522,815 A | 6/1996 | Durgin, Jr. et al. |
| 5,531,227 A | 7/1996 | Schneider |
| 5,531,520 A | 7/1996 | Grimson et al. |
| 5,531,686 A | 7/1996 | Lundquist et al. |
| 5,542,938 A | 8/1996 | Avellanet et al. |
| 5,543,951 A | 8/1996 | Moehrmann |
| 5,545,200 A | 8/1996 | West et al. |
| 5,546,940 A | 8/1996 | Panescu et al. |
| 5,546,949 A | 8/1996 | Frazin et al. |
| 5,546,951 A | 8/1996 | Ben-Haim |
| 5,551,429 A | 9/1996 | Fitzpatrick et al. |
| 5,555,883 A | 9/1996 | Avitall |
| 5,558,091 A | 9/1996 | Acker et al. |
| 5,566,681 A | 10/1996 | Manwaring et al. |
| 5,568,384 A | 10/1996 | Robb et al. |
| 5,568,809 A | 10/1996 | Ben-haim |
| 5,571,083 A | 11/1996 | Lemelson |
| 5,572,999 A | 11/1996 | Funda et al. |
| 5,573,533 A | 11/1996 | Strul |
| 5,575,794 A | 11/1996 | Walus et al. |
| 5,575,798 A | 11/1996 | Koutrouvelis |
| 5,577,991 A | 11/1996 | Akui et al. |
| 5,583,909 A | 12/1996 | Hanover |
| 5,588,033 A | 12/1996 | Yeung |
| 5,588,430 A | 12/1996 | Bova et al. |
| 5,590,215 A | 12/1996 | Allen |
| 5,592,939 A | 1/1997 | Martinelli |
| 5,595,193 A | 1/1997 | Walus et al. |
| 5,596,228 A | 1/1997 | Anderton et al. |
| 5,599,305 A | 2/1997 | Hermann et al. |
| 5,600,330 A | 2/1997 | Blood |
| 5,603,318 A | 2/1997 | Heilbrun et al. |
| 5,606,975 A | 3/1997 | Liang et al. |
| 5,611,025 A | 3/1997 | Lorensen et al. |
| 5,617,462 A | 4/1997 | Spratt |
| 5,617,857 A | 4/1997 | Chader et al. |
| 5,619,261 A | 4/1997 | Anderton |
| 5,620,734 A | 4/1997 | Wesdorp et al. |
| 5,622,169 A | 4/1997 | Golden et al. |
| 5,622,170 A | 4/1997 | Schulz |
| 5,627,873 A | 5/1997 | Hanover et al. |
| 5,628,315 A | 5/1997 | Vilsmeier et al. |
| 5,630,431 A | 5/1997 | Taylor |
| 5,636,634 A | 6/1997 | Kordis et al. |
| 5,636,644 A | 6/1997 | Hart et al. |
| 5,638,819 A | 6/1997 | Manwaring et al. |
| 5,640,170 A | 6/1997 | Anderson |
| 5,642,395 A | 6/1997 | Anderton et al. |
| 5,643,175 A | 7/1997 | Adair |
| 5,643,268 A | 7/1997 | Vilsmeier et al. |
| 5,645,065 A | 7/1997 | Shapiro et al. |
| 5,646,524 A | 7/1997 | Gilboa |
| 5,646,525 A | 7/1997 | Gilboa |
| 5,647,361 A | 7/1997 | Damadian |
| 5,651,047 A | 7/1997 | Moorman et al. |
| 5,660,865 A | 8/1997 | Pedersen et al. |
| 5,662,108 A | 9/1997 | Budd et al. |
| 5,662,111 A | 9/1997 | Cosman |
| 5,664,001 A | 9/1997 | Tachibana et al. |
| 5,674,296 A | 10/1997 | Bryan et al. |
| 5,676,673 A | 10/1997 | Ferre et al. |
| 5,681,260 A | 10/1997 | Ueda et al. |
| 5,682,165 A | 10/1997 | Lewis et al. |
| 5,682,886 A | 11/1997 | Delp et al. |
| 5,682,890 A | 11/1997 | Kormos et al. |
| 5,690,108 A | 11/1997 | Chakeres |
| 5,694,945 A | 12/1997 | Ben-Haim |
| 5,695,500 A | 12/1997 | Taylor et al. |
| 5,695,501 A | 12/1997 | Carol et al. |
| 5,696,500 A | 12/1997 | Diem |
| 5,697,377 A | 12/1997 | Wittkampf |
| 5,701,898 A | 12/1997 | Adam et al. |
| 5,702,406 A | 12/1997 | Vilsmeier et al. |
| 5,711,299 A | 1/1998 | Manwaring et al. |
| 5,713,369 A | 2/1998 | Tao et al. |
| 5,713,853 A | 2/1998 | Clark et al. |
| 5,713,946 A | 2/1998 | Ben-Haim |
| 5,715,822 A | 2/1998 | Watkins et al. |
| 5,715,836 A | 2/1998 | Kliegis et al. |
| 5,718,241 A | 2/1998 | Ben-Haim et al. |
| 5,727,552 A | 3/1998 | Ryan |
| 5,727,553 A | 3/1998 | Saad |
| 5,729,129 A | 3/1998 | Acker |
| 5,730,129 A | 3/1998 | Darrow et al. |
| 5,730,130 A | 3/1998 | Fitzpatrick et al. |
| 5,732,703 A | 3/1998 | Kalfas et al. |
| 5,735,278 A | 4/1998 | Hoult et al. |
| 5,738,096 A | 4/1998 | Ben-Haim |
| 5,740,802 A | 4/1998 | Nafis et al. |

(56) References Cited

U.S. PATENT DOCUMENTS

| | | |
|---|---|---|
| 5,740,808 A | 4/1998 | Panescu et al. |
| 5,741,214 A | 4/1998 | Ouchi et al. |
| 5,741,320 A | 4/1998 | Thornton et al. |
| 5,742,394 A | 4/1998 | Hansen |
| 5,744,802 A | 4/1998 | Muehllehner et al. |
| 5,744,953 A | 4/1998 | Hansen |
| 5,748,767 A | 5/1998 | Raab |
| 5,749,362 A | 5/1998 | Funda et al. |
| 5,749,835 A | 5/1998 | Glantz |
| 5,752,513 A | 5/1998 | Acker et al. |
| 5,752,518 A | 5/1998 | McGee et al. |
| 5,755,725 A | 5/1998 | Druais |
| RE35,816 E | 6/1998 | Schulz |
| 5,758,667 A | 6/1998 | Slettenmark |
| 5,760,335 A | 6/1998 | Gilboa |
| 5,762,064 A | 6/1998 | Polvani |
| 5,767,669 A | 6/1998 | Hansen et al. |
| 5,767,699 A | 6/1998 | Bosnyak et al. |
| 5,767,960 A | 6/1998 | Orman |
| 5,769,789 A | 6/1998 | Wang et al. |
| 5,769,843 A | 6/1998 | Abela et al. |
| 5,769,861 A | 6/1998 | Vilsmeier |
| 5,772,594 A | 6/1998 | Barrick |
| 5,775,322 A | 7/1998 | Silverstein et al. |
| 5,776,050 A | 7/1998 | Chen et al. |
| 5,776,064 A | 7/1998 | Kalfas et al. |
| 5,782,765 A | 7/1998 | Jonkman |
| 5,782,828 A | 7/1998 | Chen et al. |
| 5,787,886 A | 8/1998 | Kelly et al. |
| 5,792,055 A | 8/1998 | McKinnon |
| 5,795,294 A | 8/1998 | Luber et al. |
| 5,797,849 A | 8/1998 | Vesely et al. |
| 5,799,055 A | 8/1998 | Peshkin et al. |
| 5,799,099 A | 8/1998 | Wang et al. |
| 5,800,352 A | 9/1998 | Ferre et al. |
| 5,800,535 A | 9/1998 | Howard, III |
| 5,802,719 A | 9/1998 | O'Farrell, Jr. et al. |
| 5,803,084 A | 9/1998 | Olson |
| 5,803,089 A | 9/1998 | Ferre et al. |
| 5,807,252 A | 9/1998 | Hassfeld et al. |
| 5,810,008 A | 9/1998 | Dekel et al. |
| 5,810,728 A | 9/1998 | Kuhn |
| 5,810,735 A | 9/1998 | Halperin et al. |
| 5,820,553 A | 10/1998 | Hughes |
| 5,820,591 A | 10/1998 | Thompson et al. |
| 5,823,192 A | 10/1998 | Kalend et al. |
| 5,823,958 A | 10/1998 | Truppe |
| 5,828,725 A | 10/1998 | Levinson |
| 5,828,770 A | 10/1998 | Leis et al. |
| 5,829,444 A | 11/1998 | Ferre et al. |
| 5,831,260 A | 11/1998 | Hansen |
| 5,833,608 A | 11/1998 | Acker |
| 5,834,759 A | 11/1998 | Glossop |
| 5,836,954 A | 11/1998 | Heilbrun et al. |
| 5,837,001 A | 11/1998 | Mackey |
| 5,840,024 A | 11/1998 | Taniguchi et al. |
| 5,840,025 A | 11/1998 | Ben-Haim |
| 5,842,984 A | 12/1998 | Avitall |
| 5,843,051 A | 12/1998 | Adams et al. |
| 5,843,076 A | 12/1998 | Webster, Jr. et al. |
| 5,846,183 A | 12/1998 | Chilcoat |
| 5,848,967 A | 12/1998 | Cosman |
| 5,851,183 A | 12/1998 | Bucholz |
| 5,853,327 A | 12/1998 | Gilboa |
| 5,857,997 A | 1/1999 | Cimino et al. |
| 5,865,726 A | 2/1999 | Katsurada et al. |
| 5,865,846 A | 2/1999 | Bryan et al. |
| 5,868,673 A | 2/1999 | Vesely |
| 5,868,674 A | 2/1999 | Glowinski et al. |
| 5,868,675 A | 2/1999 | Henrion et al. |
| 5,871,445 A | 2/1999 | Bucholz |
| 5,871,455 A | 2/1999 | Ueno |
| 5,871,487 A | 2/1999 | Warner et al. |
| 5,871,523 A | 2/1999 | Fleischman et al. |
| 5,873,822 A | 2/1999 | Ferre et al. |
| 5,882,304 A | 3/1999 | Ehnholm et al. |
| 5,884,410 A | 3/1999 | Prinz |
| 5,889,834 A | 3/1999 | Vilsmeier et al. |
| 5,891,034 A | 4/1999 | Bucholz |
| 5,891,134 A | 4/1999 | Goble et al. |
| 5,891,157 A | 4/1999 | Day et al. |
| 5,893,885 A | 4/1999 | Webster, Jr. |
| 5,899,860 A | 5/1999 | Pfeiffer et al. |
| 5,902,239 A | 5/1999 | Buurman |
| 5,902,324 A | 5/1999 | Thompson et al. |
| 5,904,691 A | 5/1999 | Barnett et al. |
| 5,907,395 A | 5/1999 | Schulz et al. |
| 5,909,476 A | 6/1999 | Cheng et al. |
| 5,913,820 A | 6/1999 | Bladen et al. |
| 5,916,210 A | 6/1999 | Winston |
| 5,919,147 A | 7/1999 | Jain |
| 5,919,188 A | 7/1999 | Shearon et al. |
| 5,920,395 A | 7/1999 | Schulz |
| 5,921,992 A | 7/1999 | Costales et al. |
| 5,923,727 A | 7/1999 | Navab |
| 5,928,248 A | 7/1999 | Acker |
| 5,930,329 A | 7/1999 | Navab |
| 5,935,160 A | 8/1999 | Auricchio et al. |
| 5,938,585 A | 8/1999 | Donofrio |
| 5,938,602 A | 8/1999 | Lloyd |
| 5,938,603 A | 8/1999 | Ponzi |
| 5,938,694 A | 8/1999 | Jaraczewski et al. |
| 5,941,251 A | 8/1999 | Panescu et al. |
| 5,944,023 A | 8/1999 | Johnson et al. |
| 5,947,925 A | 9/1999 | Ashiya et al. |
| 5,947,980 A | 9/1999 | Jensen et al. |
| 5,947,981 A | 9/1999 | Cosman |
| 5,950,629 A | 9/1999 | Taylor et al. |
| 5,951,461 A | 9/1999 | Nyo et al. |
| 5,951,475 A | 9/1999 | Gueziec et al. |
| 5,951,571 A | 9/1999 | Audette |
| 5,954,647 A | 9/1999 | Bova et al. |
| 5,954,649 A | 9/1999 | Chia et al. |
| 5,954,796 A | 9/1999 | McCarty et al. |
| 5,957,844 A | 9/1999 | Dekel et al. |
| 5,966,090 A | 10/1999 | McEwan |
| 5,967,980 A | 10/1999 | Ferre et al. |
| 5,967,982 A | 10/1999 | Barnett |
| 5,968,047 A | 10/1999 | Reed |
| 5,971,997 A | 10/1999 | Guthrie et al. |
| 5,976,127 A | 11/1999 | Lax |
| 5,976,156 A | 11/1999 | Taylor et al. |
| 5,980,504 A | 11/1999 | Sharkey et al. |
| 5,980,535 A | 11/1999 | Barnett et al. |
| 5,983,126 A | 11/1999 | Wittkampf |
| 5,987,349 A | 11/1999 | Schulz |
| 5,987,960 A | 11/1999 | Messner et al. |
| 5,999,837 A | 12/1999 | Messner et al. |
| 5,999,840 A | 12/1999 | Grimson et al. |
| 6,001,130 A | 12/1999 | Bryan et al. |
| 6,004,269 A | 12/1999 | Crowley et al. |
| 6,006,126 A | 12/1999 | Cosman |
| 6,006,127 A | 12/1999 | Van Der Brug et al. |
| 6,013,087 A | 1/2000 | Adams et al. |
| 6,014,580 A | 1/2000 | Blume et al. |
| 6,016,439 A | 1/2000 | Acker |
| 6,019,724 A | 2/2000 | Gronningsaeter et al. |
| 6,019,725 A | 2/2000 | Vesely et al. |
| 6,019,728 A | 2/2000 | Iwata et al. |
| 6,022,578 A | 2/2000 | Miller |
| 6,024,695 A | 2/2000 | Taylor et al. |
| 6,024,739 A | 2/2000 | Ponzi et al. |
| 6,032,675 A | 3/2000 | Rubinsky |
| 6,035,229 A | 3/2000 | Silverstein et al. |
| 6,050,724 A | 4/2000 | Schmitz et al. |
| 6,059,718 A | 5/2000 | Taniguchi et al. |
| 6,061,588 A | 5/2000 | Thornton et al. |
| 6,063,022 A | 5/2000 | Ben-Haim |
| 6,064,390 A | 5/2000 | Sagar et al. |
| 6,071,288 A | 6/2000 | Carol et al. |
| 6,073,043 A | 6/2000 | Schneider |
| 6,076,008 A | 6/2000 | Bucholz |
| 6,077,257 A | 6/2000 | Edwards et al. |
| 6,096,036 A | 8/2000 | Bowe et al. |

(56) References Cited

U.S. PATENT DOCUMENTS

| | | | |
|---|---|---|---|
| 6,096,050 A | 8/2000 | Audette |
| 6,104,294 A | 8/2000 | Andersson et al. |
| 6,104,944 A | 8/2000 | Martinelli |
| 6,106,517 A | 8/2000 | Zupkas |
| 6,112,111 A | 8/2000 | Glantz |
| 6,115,626 A | 9/2000 | Whayne et al. |
| 6,117,476 A | 9/2000 | Eger et al. |
| 6,118,845 A | 9/2000 | Simon et al. |
| 6,122,538 A | 9/2000 | Sliwa, Jr. et al. |
| 6,122,541 A | 9/2000 | Cosman et al. |
| 6,123,979 A | 9/2000 | Hepburn et al. |
| 6,131,396 A | 10/2000 | Duerr et al. |
| 6,139,183 A | 10/2000 | Graumann |
| 6,147,480 A | 11/2000 | Osadchy et al. |
| 6,149,592 A | 11/2000 | Yanof et al. |
| 6,156,067 A | 12/2000 | Bryan et al. |
| 6,161,032 A | 12/2000 | Acker |
| 6,165,181 A | 12/2000 | Heilbrun et al. |
| 6,167,296 A | 12/2000 | Shahidi |
| 6,171,303 B1 | 1/2001 | Ben-Haim et al. |
| 6,172,499 B1 | 1/2001 | Ashe |
| 6,175,756 B1 | 1/2001 | Ferre et al. |
| 6,178,345 B1 | 1/2001 | Vilsmeier et al. |
| 6,179,809 B1 | 1/2001 | Khairkhahan et al. |
| 6,183,444 B1 | 2/2001 | Glines et al. |
| 6,188,355 B1 | 2/2001 | Gilboa |
| 6,192,280 B1 | 2/2001 | Sommer et al. |
| 6,194,639 B1 | 2/2001 | Botella et al. |
| 6,201,387 B1 | 3/2001 | Govari |
| 6,203,493 B1 | 3/2001 | Ben-Haim |
| 6,203,497 B1 | 3/2001 | Dekel et al. |
| 6,208,884 B1 | 3/2001 | Kumar et al. |
| 6,210,362 B1 | 4/2001 | Ponzi |
| 6,211,666 B1 | 4/2001 | Acker |
| 6,213,995 B1 | 4/2001 | Steen et al. |
| 6,213,998 B1 | 4/2001 | Shen et al. |
| 6,216,027 B1 | 4/2001 | Willis et al. |
| 6,216,029 B1 | 4/2001 | Paltieli |
| 6,223,067 B1 | 4/2001 | Vilsmeier et al. |
| 6,226,543 B1 | 5/2001 | Gilboa et al. |
| 6,233,476 B1 | 5/2001 | Strommer et al. |
| 6,236,875 B1 | 5/2001 | Bucholz et al. |
| 6,245,020 B1 | 6/2001 | Moore et al. |
| 6,246,231 B1 | 6/2001 | Ashe |
| 6,246,784 B1 | 6/2001 | Summers et al. |
| 6,246,898 B1 | 6/2001 | Vesely et al. |
| 6,246,899 B1 | 6/2001 | Chia et al. |
| 6,248,074 B1 | 6/2001 | Ohno et al. |
| 6,253,770 B1 | 7/2001 | Acker et al. |
| 6,259,942 B1 | 7/2001 | Westermann et al. |
| 6,264,654 B1 | 7/2001 | Swartz et al. |
| 6,272,371 B1 | 8/2001 | Shlomo |
| 6,273,896 B1 | 8/2001 | Franck et al. |
| 6,285,902 B1 | 9/2001 | Kienzle, III et al. |
| 6,298,262 B1 | 10/2001 | Franck et al. |
| 6,304,769 B1 | 10/2001 | Arenson et al. |
| 6,306,097 B1 | 10/2001 | Park et al. |
| 6,314,310 B1 | 11/2001 | Ben-Haim et al. |
| 6,319,250 B1 | 11/2001 | Falwell et al. |
| 6,331,116 B1 | 12/2001 | Kaufman et al. |
| 6,331,156 B1 | 12/2001 | Haefele et al. |
| 6,332,089 B1 | 12/2001 | Acker et al. |
| 6,335,617 B1 | 1/2002 | Osadchy et al. |
| 6,341,231 B1 | 1/2002 | Ferre et al. |
| 6,345,112 B1 | 2/2002 | Summers et al. |
| 6,346,940 B1 | 2/2002 | Fukunaga |
| 6,351,513 B1 | 2/2002 | Bani-Hashemi et al. |
| 6,351,659 B1 | 2/2002 | Vilsmeier |
| 6,366,799 B1 | 4/2002 | Acker et al. |
| 6,373,240 B1 | 4/2002 | Govari |
| 6,380,732 B1 | 4/2002 | Gilboa |
| 6,381,485 B1 | 4/2002 | Hunter et al. |
| 6,383,144 B1 | 5/2002 | Mooney et al. |
| 6,405,072 B1 | 6/2002 | Cosman |
| 6,423,009 B1 | 7/2002 | Downey et al. |
| 6,424,856 B1 | 7/2002 | Vilsmeier et al. |
| 6,427,314 B1 | 8/2002 | Acker |
| 6,428,547 B1 | 8/2002 | Vilsmeier et al. |
| 6,434,415 B1 | 8/2002 | Foley et al. |
| 6,437,567 B1 | 8/2002 | Schenck et al. |
| 6,443,894 B1 | 9/2002 | Sumanaweera et al. |
| 6,445,943 B1 | 9/2002 | Ferre et al. |
| 6,447,504 B1 | 9/2002 | Ben-Haim et al. |
| 6,453,190 B1 | 9/2002 | Acker et al. |
| 6,468,265 B1 | 10/2002 | Evans et al. |
| 6,470,207 B1 | 10/2002 | Simon et al. |
| 6,473,635 B1 | 10/2002 | Rasche |
| 6,474,341 B1 | 11/2002 | Hunter et al. |
| 6,478,802 B2 | 11/2002 | Kienzle, III et al. |
| 6,484,049 B1 | 11/2002 | Seeley et al. |
| 6,484,118 B1 | 11/2002 | Govari |
| 6,490,475 B1 | 12/2002 | Seeley et al. |
| 6,493,573 B1 | 12/2002 | Martinelli et al. |
| 6,498,477 B1 | 12/2002 | Govari et al. |
| 6,498,944 B1 | 12/2002 | Ben-Haim et al. |
| 6,499,488 B1 | 12/2002 | Hunter et al. |
| 6,516,046 B1 | 2/2003 | Frohlich et al. |
| 6,517,534 B1 | 2/2003 | McGovern et al. |
| 6,527,443 B1 | 3/2003 | Vilsmeier et al. |
| 6,551,325 B2 | 4/2003 | Neubauer et al. |
| 6,558,333 B2 | 5/2003 | Gilboa et al. |
| 6,574,492 B1 | 6/2003 | Ben-Haim et al. |
| 6,574,498 B1 | 6/2003 | Gilboa |
| 6,580,938 B1 | 6/2003 | Acker |
| 6,584,174 B2 | 6/2003 | Schubert et al. |
| 6,585,763 B1 | 7/2003 | Keilman et al. |
| 6,591,129 B1 | 7/2003 | Ben-Haim et al. |
| 6,593,884 B1 | 7/2003 | Gilboa et al. |
| 6,609,022 B2 | 8/2003 | Vilsmeier et al. |
| 6,611,700 B1 | 8/2003 | Vilsmeier et al. |
| 6,615,155 B2 | 9/2003 | Gilboa |
| 6,618,612 B1 | 9/2003 | Acker et al. |
| 6,628,980 B2 | 9/2003 | Atalar et al. |
| 6,640,128 B2 | 10/2003 | Vilsmeier et al. |
| 6,650,927 B1 | 11/2003 | Keidar |
| 6,666,864 B2 | 12/2003 | Bencini et al. |
| 6,676,659 B2 | 1/2004 | Hutchins et al. |
| 6,690,816 B2 | 2/2004 | Aylward et al. |
| 6,690,963 B2 | 2/2004 | Ben-Haim et al. |
| 6,694,162 B2 | 2/2004 | Hartlep |
| 6,701,179 B1 | 3/2004 | Martinelli et al. |
| 6,702,780 B1 | 3/2004 | Gilboa et al. |
| 6,706,041 B1 | 3/2004 | Costantino |
| 6,711,429 B1 | 3/2004 | Gilboa et al. |
| 6,735,465 B2 | 5/2004 | Panescu |
| 6,751,342 B2 * | 6/2004 | Shepard ............ G01N 25/72 |
| | | 250/332 |
| 6,751,492 B2 | 6/2004 | Ben-Haim |
| 6,770,070 B1 | 8/2004 | Balbierz |
| 6,788,967 B2 | 9/2004 | Ben-Haim et al. |
| 6,796,963 B2 | 9/2004 | Carpenter et al. |
| 6,810,281 B2 | 10/2004 | Brock et al. |
| 6,833,814 B2 | 12/2004 | Gilboa et al. |
| 6,887,236 B2 | 5/2005 | Gilboa |
| 6,947,788 B2 | 9/2005 | Gilboa et al. |
| 6,976,013 B1 | 12/2005 | Mah |
| 6,995,729 B2 | 2/2006 | Govari et al. |
| 6,996,430 B1 | 2/2006 | Gilboa et al. |
| 7,015,859 B2 * | 3/2006 | Anderson ............ A61B 5/06 |
| | | 342/450 |
| 7,033,325 B1 | 4/2006 | Sullivan |
| 7,158,754 B2 | 1/2007 | Anderson |
| 7,176,936 B2 | 2/2007 | Sauer et al. |
| 7,197,354 B2 | 3/2007 | Sobe |
| 7,233,820 B2 | 6/2007 | Gilboa |
| 7,236,567 B2 | 6/2007 | Sandkamp et al. |
| 7,286,868 B2 | 10/2007 | Govari |
| 7,301,332 B2 | 11/2007 | Govari et al. |
| 7,321,228 B2 | 1/2008 | Govari |
| 7,324,915 B2 | 1/2008 | Altmann et al. |
| 7,343,195 B2 | 3/2008 | Strommer et al. |
| 7,353,125 B2 | 4/2008 | Nieminen et al. |
| 7,357,795 B2 | 4/2008 | Kaji et al. |
| 7,366,562 B2 | 4/2008 | Dukesherer et al. |

(56) References Cited

U.S. PATENT DOCUMENTS

| | | |
|---|---|---|
| 7,370,656 B2 | 5/2008 | Gleich et al. |
| 7,373,271 B1 | 5/2008 | Schneider |
| 7,386,339 B2 | 6/2008 | Strommer et al. |
| 7,397,364 B2 | 7/2008 | Govari |
| 7,399,296 B2 | 7/2008 | Poole et al. |
| 7,420,468 B2 | 9/2008 | Fabian et al. |
| 7,497,029 B2 | 3/2009 | Plassky et al. |
| 7,505,809 B2 | 3/2009 | Strommer et al. |
| 7,517,318 B2 | 4/2009 | Altmann et al. |
| 7,536,218 B2 | 5/2009 | Govari et al. |
| 7,555,330 B2 | 6/2009 | Gilboa et al. |
| RE40,852 E | 7/2009 | Martinelli et al. |
| 7,570,987 B2 | 8/2009 | Raabe et al. |
| 7,577,474 B2 | 8/2009 | Vilsmeier |
| 7,579,837 B2 | 8/2009 | Fath et al. |
| 7,587,235 B2 | 9/2009 | Wist et al. |
| 7,599,535 B2 | 10/2009 | Kiraly et al. |
| 7,599,810 B2 | 10/2009 | Yamazaki |
| 7,630,753 B2 | 12/2009 | Simon et al. |
| 7,634,122 B2 | 12/2009 | Bertram et al. |
| 7,636,595 B2 | 12/2009 | Marquart et al. |
| 7,641,609 B2 | 1/2010 | Ohnishi et al. |
| 7,648,458 B2 | 1/2010 | Niwa et al. |
| 7,652,468 B2 | 1/2010 | Kruger et al. |
| 7,652,578 B2 | 1/2010 | Braun et al. |
| 7,657,300 B2 | 2/2010 | Hunter et al. |
| 7,659,912 B2 | 2/2010 | Akimoto et al. |
| 7,660,623 B2 | 2/2010 | Hunter et al. |
| 7,680,528 B2 | 3/2010 | Pfister et al. |
| 7,684,849 B2 | 3/2010 | Wright et al. |
| 7,686,767 B2 | 3/2010 | Maschke |
| 7,688,064 B2 | 3/2010 | Shalgi et al. |
| 7,696,899 B2 | 4/2010 | Immerz et al. |
| 7,697,973 B2 | 4/2010 | Strommer et al. |
| 7,697,974 B2 | 4/2010 | Jenkins et al. |
| 7,720,517 B2 | 5/2010 | Drysen |
| 7,722,565 B2 | 5/2010 | Wood et al. |
| 7,725,154 B2 | 5/2010 | Beck et al. |
| 7,725,164 B2 | 5/2010 | Suurmond et al. |
| 7,727,269 B2 | 6/2010 | Abraham-Fuchs et al. |
| 7,729,742 B2 | 6/2010 | Govari |
| 7,744,605 B2 | 6/2010 | Vilsmeier et al. |
| 7,747,307 B2 | 6/2010 | Wright et al. |
| 7,751,865 B2 | 7/2010 | Jascob et al. |
| 7,782,046 B2 | 8/2010 | Anderson |
| 7,782,189 B2 | 8/2010 | Spoonhower et al. |
| 7,784,468 B2 | 8/2010 | Fabian et al. |
| 7,831,076 B2 | 11/2010 | Altmann et al. |
| 7,905,827 B2 | 3/2011 | Uchiyama et al. |
| 7,912,662 B2 | 3/2011 | Zuhars et al. |
| 7,969,143 B2 | 6/2011 | Gilboa |
| 8,692,707 B2 | 4/2014 | Lee et al. |
| 9,575,140 B2 | 2/2017 | Zur |
| 2001/0007918 A1 | 7/2001 | Vilsmeier et al. |
| 2001/0031919 A1 | 10/2001 | Strommer et al. |
| 2001/0034530 A1 | 10/2001 | Malackowski et al. |
| 2001/0036245 A1 | 11/2001 | Kienzle et al. |
| 2001/0038705 A1 | 11/2001 | Rubbert et al. |
| 2002/0022837 A1 | 2/2002 | Mazzocchi et al. |
| 2002/0045916 A1 | 4/2002 | Gray et al. |
| 2002/0045919 A1 | 4/2002 | Johansson-Ruden et al. |
| 2002/0065461 A1 | 5/2002 | Cosman |
| 2002/0082498 A1 | 6/2002 | Wendt et al. |
| 2002/0095081 A1 | 7/2002 | Vilsmeier |
| 2002/0128565 A1 | 9/2002 | Rudy |
| 2002/0137014 A1 | 9/2002 | Anderson et al. |
| 2002/0143324 A1 | 10/2002 | Edwards |
| 2002/0165448 A1 | 11/2002 | Ben-Haim et al. |
| 2002/0173689 A1 | 11/2002 | Kaplan |
| 2002/0193686 A1 | 12/2002 | Gilboa |
| 2003/0018251 A1 | 1/2003 | Solomon |
| 2003/0074011 A1 | 4/2003 | Gilboa et al. |
| 2003/0086599 A1 | 5/2003 | Armato et al. |
| 2003/0099390 A1 | 5/2003 | Zeng et al. |
| 2003/0142753 A1 | 7/2003 | Gunday |
| 2003/0144658 A1 | 7/2003 | Schwartz et al. |
| 2003/0160721 A1 | 8/2003 | Gilboa et al. |
| 2003/0184285 A1* | 10/2003 | Anderson ............... A61B 5/06 324/207.17 |
| 2003/0216639 A1 | 11/2003 | Gilboa et al. |
| 2004/0006268 A1 | 1/2004 | Gilboa et al. |
| 2004/0015049 A1 | 1/2004 | Zaar |
| 2004/0019350 A1 | 1/2004 | O'Brien et al. |
| 2004/0024309 A1 | 2/2004 | Ferre et al. |
| 2004/0086161 A1 | 5/2004 | Sivaramakrishna et al. |
| 2004/0097804 A1 | 5/2004 | Sobe |
| 2004/0122310 A1 | 6/2004 | Lim |
| 2004/0135992 A1* | 7/2004 | Munro ................... G01S 7/483 356/4.01 |
| 2004/0138548 A1 | 7/2004 | Strommer et al. |
| 2004/0143317 A1 | 7/2004 | Stinson et al. |
| 2004/0169509 A1 | 9/2004 | Czipott et al. |
| 2004/0215181 A1 | 10/2004 | Christopherson et al. |
| 2004/0249267 A1 | 12/2004 | Gilboa |
| 2004/0254454 A1 | 12/2004 | Kockro |
| 2005/0018885 A1 | 1/2005 | Chen et al. |
| 2005/0027193 A1 | 2/2005 | Mitschke et al. |
| 2005/0033149 A1 | 2/2005 | Strommer et al. |
| 2005/0059890 A1 | 3/2005 | Deal et al. |
| 2005/0085715 A1 | 4/2005 | Dukesherer et al. |
| 2005/0085720 A1 | 4/2005 | Jascob et al. |
| 2005/0090818 A1 | 4/2005 | Pike et al. |
| 2005/0107687 A1 | 5/2005 | Anderson |
| 2005/0107688 A1 | 5/2005 | Strommer |
| 2005/0119527 A1 | 6/2005 | Banik et al. |
| 2005/0182295 A1 | 8/2005 | Soper et al. |
| 2005/0197566 A1 | 9/2005 | Strommer et al. |
| 2005/0222793 A1 | 10/2005 | Lloyd et al. |
| 2005/0272971 A1 | 12/2005 | Ohnishi et al. |
| 2006/0015126 A1 | 1/2006 | Sher |
| 2006/0025677 A1 | 2/2006 | Verard et al. |
| 2006/0036151 A1 | 2/2006 | Ferre et al. |
| 2006/0058647 A1 | 3/2006 | Strommer et al. |
| 2006/0064006 A1 | 3/2006 | Strommer et al. |
| 2006/0079759 A1 | 4/2006 | Valliant et al. |
| 2006/0084867 A1 | 4/2006 | Tremblay et al. |
| 2006/0116575 A1 | 6/2006 | Willis |
| 2006/0149134 A1 | 7/2006 | Soper et al. |
| 2006/0181271 A1 | 8/2006 | Lescourret |
| 2006/0208725 A1 | 9/2006 | Tapson |
| 2006/0241396 A1 | 10/2006 | Fabian et al. |
| 2006/0241399 A1 | 10/2006 | Fabian |
| 2007/0163597 A1 | 7/2007 | Mikkaichi et al. |
| 2007/0167714 A1 | 7/2007 | Kiraly et al. |
| 2007/0167738 A1 | 7/2007 | Timinger et al. |
| 2007/0167743 A1 | 7/2007 | Honda et al. |
| 2007/0167804 A1 | 7/2007 | Park et al. |
| 2007/0167806 A1 | 7/2007 | Wood et al. |
| 2007/0225553 A1 | 9/2007 | Shahidi |
| 2007/0232898 A1 | 10/2007 | Huynh et al. |
| 2007/0265639 A1 | 11/2007 | Danek et al. |
| 2007/0287901 A1 | 12/2007 | Strommer et al. |
| 2008/0008368 A1 | 1/2008 | Matsumoto |
| 2008/0018468 A1 | 1/2008 | Volpi et al. |
| 2008/0033452 A1 | 2/2008 | Vetter et al. |
| 2008/0086051 A1 | 4/2008 | Voegele |
| 2008/0097154 A1 | 4/2008 | Makower et al. |
| 2008/0097187 A1 | 4/2008 | Gielen et al. |
| 2008/0118135 A1 | 5/2008 | Averbuch et al. |
| 2008/0132909 A1 | 6/2008 | Jascob et al. |
| 2008/0132911 A1 | 6/2008 | Sobe |
| 2008/0139886 A1 | 6/2008 | Tatsuyama |
| 2008/0139915 A1 | 6/2008 | Dolan et al. |
| 2008/0144909 A1 | 6/2008 | Wiemker et al. |
| 2008/0147000 A1 | 6/2008 | Seibel et al. |
| 2008/0154172 A1 | 6/2008 | Mauch |
| 2008/0157755 A1 | 7/2008 | Kruger et al. |
| 2008/0161682 A1 | 7/2008 | Kendrick et al. |
| 2008/0162074 A1 | 7/2008 | Schneider |
| 2008/0183071 A1 | 7/2008 | Strommer et al. |
| 2008/0188749 A1 | 8/2008 | Rasche et al. |
| 2008/0247622 A1 | 10/2008 | Aylward et al. |
| 2008/0284554 A1 | 11/2008 | Schroeder et al. |
| 2009/0027258 A1 | 1/2009 | Stayton |

(56) References Cited

U.S. PATENT DOCUMENTS

| | | | |
|---|---|---|---|
| 2009/0082665 A1 | 3/2009 | Anderson | |
| 2009/0182224 A1 | 7/2009 | Shmarak et al. | |
| 2009/0189820 A1 | 7/2009 | Saito et al. | |
| 2009/0318797 A1 | 12/2009 | Hadani | |
| 2011/0066025 A1* | 3/2011 | Bahn | G01N 24/08 |
| | | | 600/410 |
| 2011/0085720 A1 | 4/2011 | Barak et al. | |
| 2011/0112425 A1* | 5/2011 | Muhlsteff | A61B 5/0507 |
| | | | 600/534 |
| 2011/0181273 A1* | 7/2011 | Iida | A61B 1/00158 |
| | | | 324/207.11 |
| 2015/0035697 A1 | 2/2015 | Cho | |
| 2016/0274060 A1* | 9/2016 | Denenberg | G01N 27/9046 |
| 2016/0363664 A1* | 12/2016 | Mindell | G01S 7/352 |

FOREIGN PATENT DOCUMENTS

| | | |
|---|---|---|
| DE | 3520782 A1 | 12/1986 |
| DE | 3717871 A1 | 12/1988 |
| DE | 3838011 A1 | 7/1989 |
| DE | 4213426 A1 | 10/1992 |
| DE | 4225112 C1 | 12/1993 |
| DE | 4233978 C1 | 4/1994 |
| DE | 19715202 A1 | 10/1998 |
| DE | 19751761 A1 | 10/1998 |
| DE | 19832296 A1 | 2/1999 |
| DE | 19747427 A1 | 5/1999 |
| DE | 10085137 T1 | 11/2002 |
| EP | 0062941 A1 | 10/1982 |
| EP | 0119660 A1 | 9/1984 |
| EP | 0155857 A2 | 9/1985 |
| EP | 0319844 A1 | 6/1989 |
| EP | 0326768 A2 | 8/1989 |
| EP | 0350996 A1 | 1/1990 |
| EP | 0427358 A1 | 5/1991 |
| EP | 0456103 A2 | 11/1991 |
| EP | 0581704 A1 | 2/1994 |
| EP | 0600610 A2 | 6/1994 |
| EP | 0655138 B1 | 5/1995 |
| EP | 0796633 A1 | 9/1997 |
| EP | 0 829 229 A1 | 3/1998 |
| EP | 0894473 A2 | 2/1999 |
| EP | 0908146 A2 | 4/1999 |
| EP | 0 922 966 A2 | 6/1999 |
| EP | 0930046 A2 | 7/1999 |
| EP | 1078644 A1 | 2/2001 |
| EP | 2096523 A1 | 9/2009 |
| FR | 2618211 A1 | 1/1989 |
| GB | 2094590 A | 9/1982 |
| GB | 2164856 A | 4/1986 |
| GB | 2197078 A | 5/1988 |
| JP | 03-267054 A | 11/1991 |
| JP | 06194639 A | 7/1994 |
| JP | 3025752 B2 | 3/2000 |
| WO | 88/09151 A1 | 12/1988 |
| WO | 89/05123 A1 | 6/1989 |
| WO | 90/05494 A1 | 5/1990 |
| WO | 91/03982 A1 | 4/1991 |
| WO | 91/04711 A1 | 4/1991 |
| WO | 91/07726 A1 | 5/1991 |
| WO | 92/03090 A1 | 3/1992 |
| WO | 92/06645 A1 | 4/1992 |
| WO | 94/04938 A1 | 3/1994 |
| WO | 94/23647 A1 | 10/1994 |
| WO | 94/24933 A1 | 11/1994 |
| WO | 95/07055 A1 | 3/1995 |
| WO | 95/09562 A1 | 4/1995 |
| WO | 9605768 A1 | 2/1996 |
| WO | 96/11624 A2 | 4/1996 |
| WO | 96/32059 A1 | 10/1996 |
| WO | 96/41119 A1 | 12/1996 |
| WO | 97/00011 A1 | 1/1997 |
| WO | 97/00054 A1 | 1/1997 |
| WO | 97/00058 A1 | 1/1997 |
| WO | 97/00059 A1 | 1/1997 |
| WO | 97/00308 A1 | 1/1997 |
| WO | 97/02650 A1 | 1/1997 |
| WO | 97/25101 A2 | 7/1997 |
| WO | 97/29682 A1 | 8/1997 |
| WO | 97/29684 A1 | 8/1997 |
| WO | 97/29685 A1 | 8/1997 |
| WO | 97/29701 A1 | 8/1997 |
| WO | 97/29709 A1 | 8/1997 |
| WO | 97/36143 A1 | 10/1997 |
| WO | 97/36192 A1 | 10/1997 |
| WO | 97/42517 A1 | 11/1997 |
| WO | 97/44089 A1 | 11/1997 |
| WO | 97/49453 A1 | 12/1997 |
| WO | 98/00034 A2 | 1/1998 |
| WO | 98/08554 A1 | 3/1998 |
| WO | 98/11840 A1 | 3/1998 |
| WO | 98/29032 A1 | 7/1998 |
| WO | 98/35720 A2 | 8/1998 |
| WO | 98/38908 A1 | 9/1998 |
| WO | 98/48722 A1 | 11/1998 |
| WO | 99/15097 A2 | 4/1999 |
| WO | 99/16350 A1 | 4/1999 |
| WO | 99/21498 A1 | 5/1999 |
| WO | 99/23956 A1 | 5/1999 |
| WO | 99/26549 A1 | 6/1999 |
| WO | 99/26826 A1 | 6/1999 |
| WO | 99/27839 A2 | 6/1999 |
| WO | 99/29253 A1 | 6/1999 |
| WO | 9930777 A1 | 6/1999 |
| WO | 99/32033 A1 | 7/1999 |
| WO | 99/33406 A1 | 7/1999 |
| WO | 99/37208 A1 | 7/1999 |
| WO | 99/38449 A1 | 8/1999 |
| WO | 99/52094 A1 | 10/1999 |
| WO | 9955415 A1 | 11/1999 |
| WO | 99/60939 A1 | 12/1999 |
| WO | 00/06701 A1 | 2/2000 |
| WO | 00/16684 A1 | 3/2000 |
| WO | 0010456 A1 | 3/2000 |
| WO | 00/35531 A1 | 6/2000 |
| WO | 01/06917 A1 | 2/2001 |
| WO | 0112057 A1 | 2/2001 |
| WO | 01/30437 A1 | 5/2001 |
| WO | 0167035 A1 | 9/2001 |
| WO | 01/87136 A2 | 11/2001 |
| WO | 01/91842 A1 | 12/2001 |
| WO | 02/64011 A2 | 8/2002 |
| WO | 02/70047 A1 | 9/2002 |
| WO | 03/86498 A2 | 10/2003 |
| WO | 2004/023986 A1 | 3/2004 |
| WO | 2006/116597 A2 | 11/2006 |
| WO | 2015164171 A1 | 10/2015 |

* cited by examiner

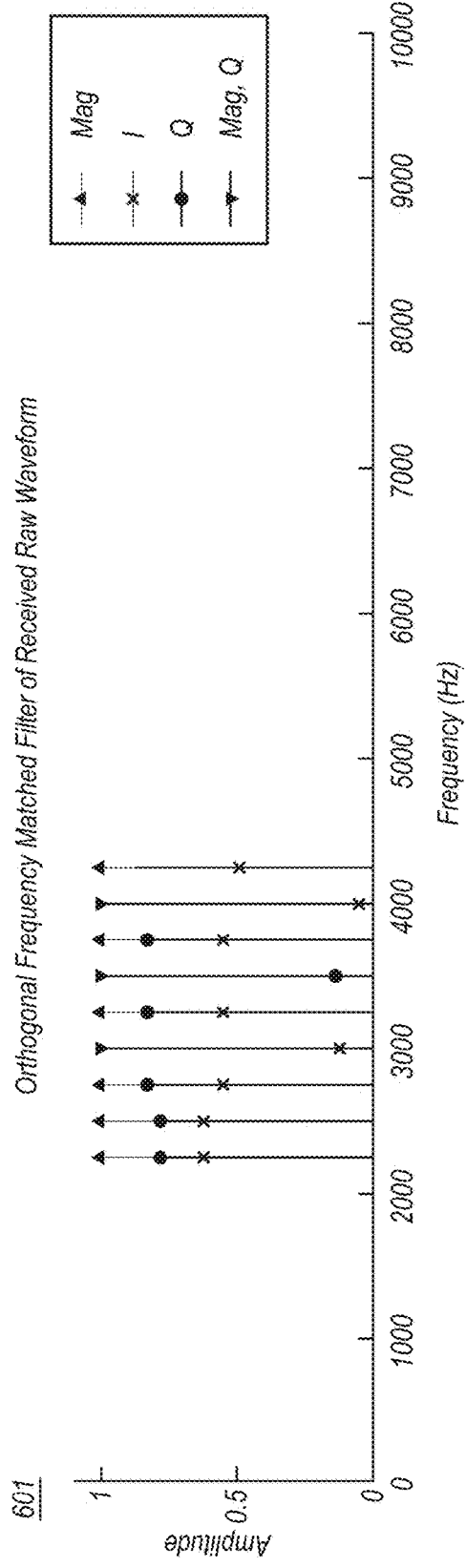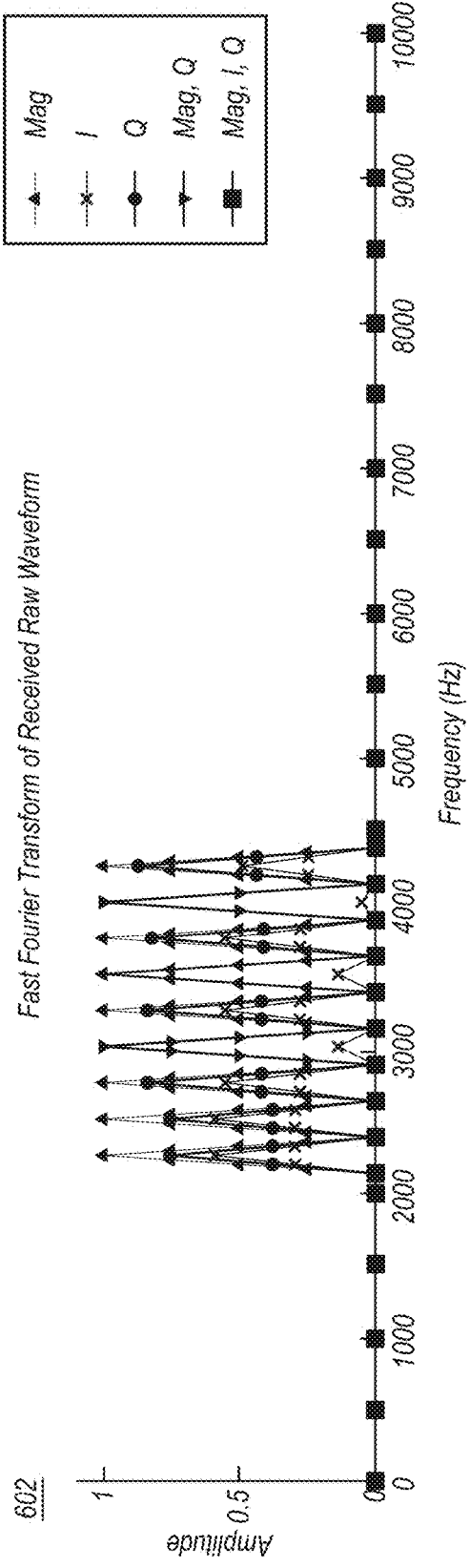

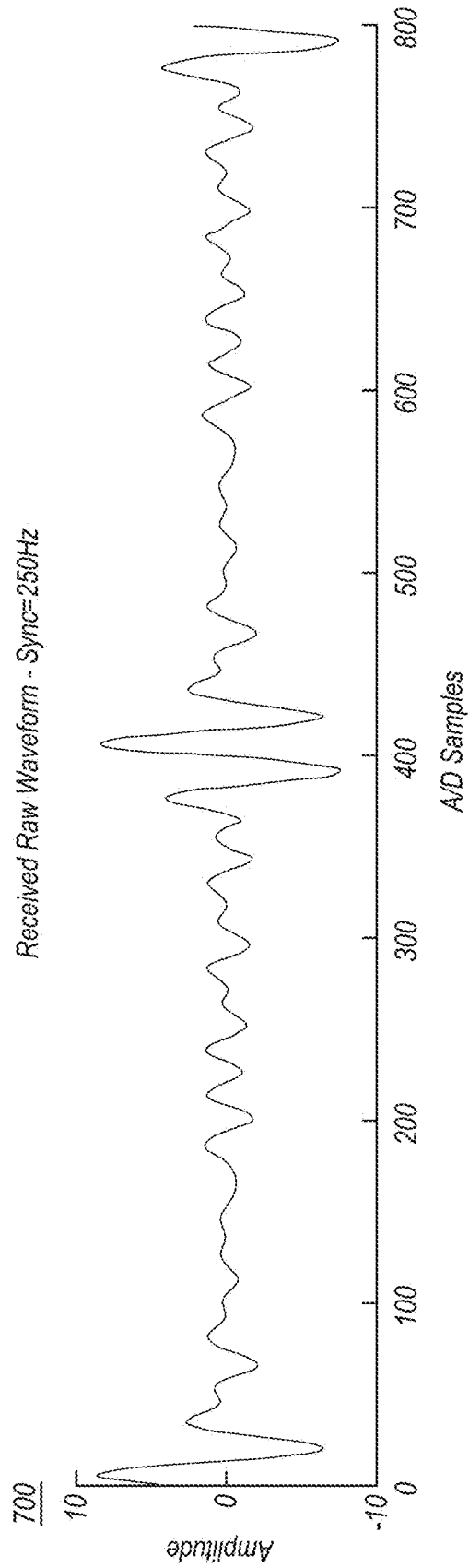
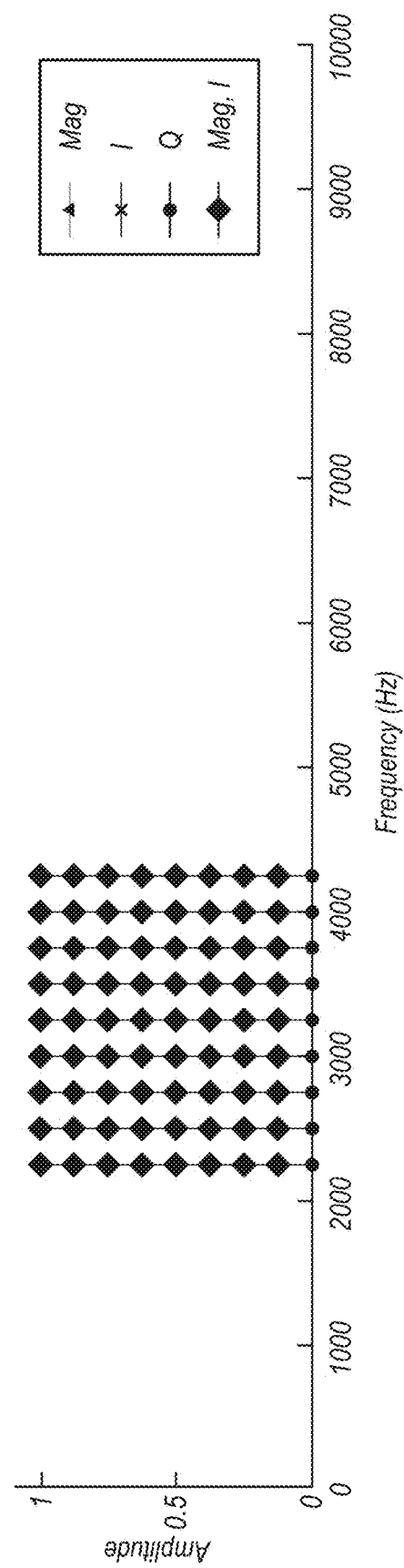
FIG. 7A
FIG. 7B

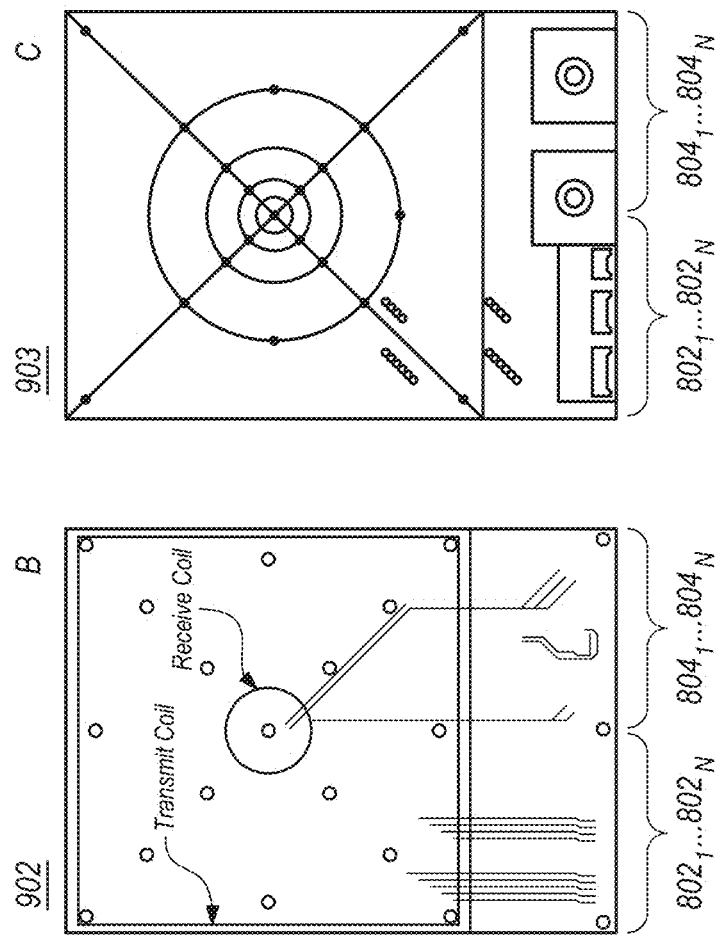
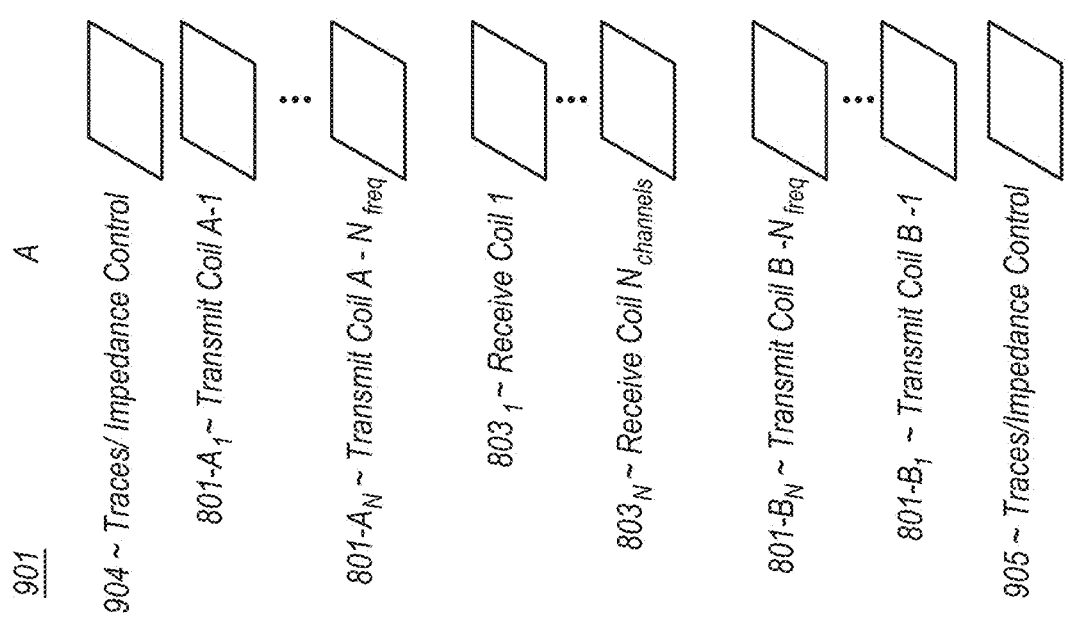

METHODS, SYSTEMS, AND COMPUTER-READABLE MEDIA FOR CALIBRATING AN ELECTROMAGNETIC NAVIGATION SYSTEM

BACKGROUND

Technical Field

The present disclosure generally relates to electromagnetic navigation, and more particularly, to systems, methods, and computer-readable media for calibrating and optimizing an electromagnetic navigation system.

Discussion of Related Art

Electromagnetic navigation (EMN) has helped expand medical imaging, diagnosis, prognosis, and treatment capabilities by enabling a location and/or an orientation of a medical device to be accurately determined while the device is within the body of a patient. One example of a medical procedure in which EMN is employed is ELECTROMAGNETIC NAVIGATION BRONCHOSCOPY® (ENB™), which includes a planning phase and a navigation phase. During the planning phase, a computed tomography (CT) scan of the chest of the patient is used to generate a virtual three-dimensional bronchial map of the patient and a planned pathway for the navigation phase. During the navigation phase, a field generating antenna assembly radiates an electromagnetic signal (for example, including one or more cosine waves) throughout a sensing volume within which the chest of the patient is positioned. A practitioner inserts into the airway of the patient an electromagnetic sensor that senses the radiated electromagnetic signal. A computing device captures a sample of the electromagnetic signal during a sampling window, and determines a location and/or an orientation (e.g., relative to the planned pathway) of the electromagnetic sensor based on characteristics (e.g., amplitude and/or phase) of the sampled electromagnetic signal and based on a previously generated mapping of electromagnetic signal measurements at respective sensor locations in the sensing volume.

In some cases—for instance, because of various sensor or antenna inductances, signal chain delays (e.g., analog or digital), and/or any delay from when the synchronization pulse occurs to when the acquisition or electromagnetic field generation actually begins—the sampled electromagnetic signal captured during the sampling window may not include a perfect cosine (or sine) waveform. Also, because of variations in the output current level(s) of transmitter channel(s) and/or in the gain(s) of receiver channel circuitry, the amplitude of the sampled electromagnetic signal captured at a particular location and orientation within the sensing volume relative to the field generating antenna assembly may vary from system to system. Additionally, because generating the mapping of electromagnetic signal measurements at respective sensor locations in the sensing volume can be laborious and time consuming, it may be desirable to reuse in multiple other systems a mapping that was previously generated based on an initial system. In order to do so, however, the initial system and the multiple other systems may require calibration to some common baseline.

Given the foregoing, a need exists for systems and methods for calibrating and/or optimizing an electromagnetic navigation system.

SUMMARY

In accordance with one aspect of the present disclosure, a method for calibrating an electromagnetic navigation system is provided. The method includes receiving, by way of a receiving antenna, a signal having a first magnitude value and a first phase value. A non-calibrated in-phase component and a non-calibrated quadrature component are computed based on the first magnitude value and the first phase value. A calibrated phase value is computed based on the non-calibrated in-phase component and the non-calibrated quadrature component. A calibrated in-phase component is computed based on the calibrated phase value, the non-calibrated in-phase component, and the non-calibrated quadrature component. A calibrated quadrature component is computed based on the calibrated phase value, the non-calibrated in-phase component, and the non-calibrated quadrature component. A calibrated magnitude value is computed based on the calibrated in-phase component. The calibrated phase value and the calibrated magnitude value are stored in a table for use during an electromagnetic navigation procedure.

In another aspect of the present disclosure, the method further includes transmitting the signal by way of a transmitting antenna, with the transmitting and receiving being synchronized to one another.

In yet another aspect of the present disclosure, the method further includes performing a lookup in a sine table and/or a cosine table based on the first magnitude value and the first phase value, with the computing of the non-calibrated in-phase component and/or the non-calibrated quadrature component being based on a result of the lookup.

In a further aspect of the present disclosure, the calibrated phase value is computed according to the equation:

$$\theta_{cal} = \tan^{-1}\left(\frac{Q_{non-calibrated}}{I_{non-calibrated}}\right),$$

where $\theta_{cal}$ represents the calibrated phase value, $Q_{non-calibrated}$ represents the non-calibrated quadrature component, and $I_{non-calibrated}$ represents the non-calibrated in-phase component.

In still another aspect of the present disclosure, the calibrated in-phase component is computed according to the equation:

$$I_{calibrated} = I_{non-calibrated} \times \cos(\theta_{cal}) + Q_{non-calibrated} \times \sin(\theta_{cal}),$$

where $I_{calibrated}$ represents the calibrated in-phase component, $I_{non-calibrated}$ represents the non-calibrated in-phase component, $\theta_{cal}$ represents the calibrated phase value, and $\theta_{non-calibrated}$ represents the non-calibrated quadrature component.

In another aspect of the present disclosure, the calibrated quadrature component is computed according to the equation:

$$Q_{calibrated} = -I_{non-calibrated} \times \sin(\theta_{cal}) + Q_{non-calibrated} \times \cos(\theta_{cal}),$$

where $Q_{calibrated}$ represents the calibrated quadrature component, $I_{non-calibrated}$ represents the non-calibrated in-phase component, $\theta_{cal}$ represents the calibrated phase value, and $\theta_{non-calibrated}$ represents the non-calibrated quadrature component.

In yet another aspect of the present disclosure, the calibrated magnitude value is computed according to the equation:

$$M_{cal} = \frac{1}{I_{calibrated}},$$

where $M_{cal}$ represents the calibrated magnitude value and $I_{calibrated}$ represents the calibrated in-phase component.

In a further aspect of the present disclosure, the method further includes determining whether the calibrated magnitude value is less than zero. In response to a determination that the calibrated magnitude value is less than zero, a second calibrated phase value is computed, and the calibrated magnitude value, the calibrated in-phase component, and the calibrated quadrature component are recomputed based on the second calibrated phase value.

In still another aspect of the present disclosure, the method further includes determining whether the calibrated magnitude value is less than zero and whether the calibrated phase value is less than or equal to zero. In response to a determination that the calibrated magnitude value is less than zero and the calibrated phase value is less than or equal to zero, a second calibrated phase value is computed according to the equation:

$$\theta_{cal}' = \theta_{cal} + \pi,$$

where $\theta_{cal}'$ represents the second calibrated phase value and $\theta_{cal}$ represents the calibrated phase value. The calibrated magnitude value, the calibrated in-phase component, and the calibrated quadrature component are recomputed based on the second calibrated phase value.

In another aspect of the present disclosure, the method further includes determining whether the calibrated magnitude value is less than zero and whether the calibrated phase value is greater than zero. In response to a determination that the calibrated magnitude value is less than zero and the calibrated phase value is greater than zero, a second calibrated phase value is computed according to the equation:

$$\theta_{cal}' = \theta_{cal} - \pi,$$

where $\theta_{cal}'$ represents the second calibrated phase value and $\theta_{cal}$ represents the calibrated phase value. The calibrated magnitude value, the calibrated in-phase component, and the calibrated quadrature component are recomputed based on the second calibrated phase value.

In yet another aspect of the present disclosure, the method further includes, during the electromagnetic navigation procedure, receiving a second signal having a second magnitude value and a second phase value; computing a second non-calibrated in-phase component and a second non-calibrated quadrature component based on the second magnitude value and the second phase value; and computing a corrected in-phase component and a corrected quadrature component based on the calibrated phase value, the calibrated magnitude value, the second non-calibrated in-phase component, and the second non-calibrated quadrature component.

In a further aspect of the present disclosure, the corrected in-phase component is computed according to the equation:

$$I_c = M_{cal} \times ((I_{non-cal2}) \times \cos(\theta_{cal}) + (Q_{non-cal2}) \times \sin(\theta_{cal})), \text{ and}$$

the corrected quadrature component is computed according to the equation:

$$Q_c = M_{cal} \times (-(I_{non-cal2}) \times \sin(\theta_{cal}) + (Q_{non-cal2}) \times \cos(\theta_{cal})),$$

where $I_c$ represents the corrected in-phase component, $M_{cal}$ represents the calibrated magnitude value, $I_{non-cal2}$ represents the second non-calibrated in-phase component, $\theta_{cal}$ represents the calibrated phase value, $Q_{non-cal2}$ represents the second non-calibrated quadrature component, and $Q_c$ represents the corrected quadrature component.

In accordance with another aspect of the present disclosure, a system for calibrating an electromagnetic navigation system is provided. The system includes a processor and a memory. The memory includes instructions that, when executed by the processor, cause the processor to receive, by way of a receiving antenna, a signal having a first magnitude value and a first phase value. A non-calibrated in-phase component and a non-calibrated quadrature component are computed based on the first magnitude value and the first phase value. A calibrated phase value is computed based on the non-calibrated in-phase component and the non-calibrated quadrature component. A calibrated in-phase component is computed based on the calibrated phase value, the non-calibrated in-phase component, and the non-calibrated quadrature component. A calibrated quadrature component is computed based on the calibrated phase value, the non-calibrated in-phase component, and the non-calibrated quadrature component. A calibrated magnitude value is computed based on the calibrated in-phase component. The calibrated phase value and the calibrated magnitude value are stored, in a table in the memory, for use during an electromagnetic navigation procedure.

In another aspect of the present disclosure, the memory further stores instructions that, when executed by the processor, cause the processor to compute the calibrated phase value according to the equation:

$$\theta_{cal} = \tan^{-1}\left(\frac{Q_{non-calibrated}}{I_{non-calibrated}}\right),$$

where $\theta_{cal}$ represents the calibrated phase value, $Q_{non-calibrated}$ represents the non-calibrated quadrature component, and $I_{non-calibrated}$ represents the non-calibrated in-phase component.

In a further aspect of the present disclosure, the memory further stores instructions that, when executed by the processor, cause the processor to compute the calibrated in-phase component according to the equation:

$$I_{calibrated} = I_{non-calibrated} \times \cos(\theta_{cal}) + Q_{non-calibrated} \times \sin(\theta_{cal}),$$

where $I_{calibrated}$ represents the calibrated in-phase component, $I_{non-calibrated}$ represents the non-calibrated in-phase component, $\theta_{cal}$ represents the calibrated phase value, and $Q_{non-calibrated}$ represents the non-calibrated quadrature component.

In yet another aspect of the present disclosure, the memory further stores instructions that, when executed by the processor, cause the processor to compute the calibrated quadrature component according to the equation:

$$Q_{calibrated} = -I_{non-calibrated} \times \sin(\theta_{cal}) + Q_{non-calibrated} \times \cos(\theta_{cal}),$$

where $Q_{calibrated}$ represents the calibrated quadrature component, $I_{non-calibrated}$ represents the non-calibrated in-phase component, $\theta_{cal}$ represents the calibrated phase value, and $Q_{non-calibrated}$ represents the non-calibrated quadrature component.

In another aspect of the present disclosure, the memory further stores instructions that, when executed by the processor, cause the processor to compute the calibrated magnitude value according to the equation:

$$M_{cal} = \frac{1}{I_{calibrated}},$$

where $M_{cal}$ represents the calibrated magnitude value and $I_{calibrated}$ represents the calibrated in-phase component.

In a further aspect of the present disclosure, the memory also stores instructions that, when executed by the processor, cause the processor to determine whether the calibrated magnitude value is less than zero. In response to a determination that the calibrated magnitude value is less than zero the processor executes the instructions to compute a second calibrated phase value, and recompute the calibrated magnitude value, the calibrated in-phase component, and the calibrated quadrature component based on the second calibrated phase value.

In yet another aspect of the present disclosure, the memory further stores instructions that, when executed by the processor, cause the processor to, during the electromagnetic navigation procedure, (1) receive a second signal having a second magnitude value and a second phase value; (2) compute a second non-calibrated in-phase component and a second non-calibrated quadrature component based on the second magnitude value and the second phase value; and (3) compute a corrected in-phase component and a corrected quadrature component based on the calibrated phase value, the calibrated magnitude value, the second non-calibrated in-phase component, and the second non-calibrated quadrature component.

In accordance with another aspect of the present disclosure, a non-transitory computer-readable medium is provided. The computer-readable medium stores sequences of instructions that, when executed by a processor, cause the processor to perform a method for calibrating an electromagnetic navigation system. The method includes receiving, by way of a receiving antenna, a signal having a first magnitude value and a first phase value. A non-calibrated in-phase component and a non-calibrated quadrature component are computed based on the first magnitude value and the first phase value. A calibrated phase value is computed based on the non-calibrated in-phase component and the non-calibrated quadrature component. A calibrated in-phase component is computed based on the calibrated phase value, the non-calibrated in-phase component, and the non-calibrated quadrature component, and a calibrated quadrature component is computed based on the calibrated phase value, the non-calibrated in-phase component, and the non-calibrated quadrature component. A calibrated magnitude value is computed based on the calibrated in-phase component. The calibrated phase value and the calibrated magnitude value are stored in a table for use during an electromagnetic navigation procedure.

In accordance with another aspect of the present disclosure, a system including an antenna assembly for calibrating an electromagnetic navigation system is provided. The antenna assembly includes a substrate, multiple pairs of transmit coils, multiple receive coils, multiple input terminals, and multiple output terminals. The substrate includes multiple layers, with each of the transmit coils being deposited on a respective one of the layers, and each of the receive coils being deposited on another respective one of the layers. Each of the pairs of transmit coils corresponds to a respective one of the receive coils. Each of the input terminals is coupled to a respective one of the pairs of transmit coils, and each of the output terminals is coupled to a respective one of the receive coils.

In another aspect of the present disclosure, each of the receive coils of the system is arranged on a respective one of the layers that is located in between a pair of the layers on which the corresponding pair of transmit coils are respectively deposited.

In further aspects of the present disclosure, each of the pairs of transmit coils of the system forms a Helmholtz pair and/or the antenna assembly of the system is an impedance-controlled antenna assembly.

In yet another aspect of the present disclosure, the system further includes a computing device including a processor and a memory. The processor is coupled to the pairs of transmit coils by way of the input terminals, respectively, and is coupled to the receive coils by way of the output terminals, respectively. The memory includes instructions that, when executed by the processor, cause the processor to transmit, by way of at least one of the pairs of transmit coils, a signal having a first magnitude value and a first phase value. The signal is received by way of at least one of the receive coils. A non-calibrated in-phase component and a non-calibrated quadrature component are computed based on the first magnitude value and the first phase value. A calibrated phase value is computed based on the non-calibrated in-phase component and the non-calibrated quadrature component. A calibrated in-phase component is computed based on the calibrated phase value, the non-calibrated in-phase component, and the non-calibrated quadrature component. A calibrated quadrature component is computed based on the calibrated phase value, the non-calibrated in-phase component, and the non-calibrated quadrature component. A calibrated magnitude value is computed based on the calibrated in-phase component. The calibrated phase value and the calibrated magnitude value are stored in a table for use during an electromagnetic navigation procedure.

In another aspect of the present disclosure, the system is configured such that the transmitting of the signal by way of one or more of the pairs of transmit coils and the receiving of the signal by way of one or more of the receive coils are synchronized to one another.

In a further aspect of the present disclosure, the memory stores further instructions that, when executed by the processor, cause the processor to perform a lookup in a sine table and/or a cosine table based on the first magnitude value and the first phase value, and the computing of the non-calibrated in-phase component and/or the non-calibrated quadrature component is further based on a result of the lookup.

In yet another aspect of the present disclosure, the memory stores further instructions that, when executed by the processor, cause the processor to compute the calibrated phase value according to the equation:

$$\theta_{cal} = \tan^{-1}\left(\frac{Q_{non-calibrated}}{I_{non-calibrated}}\right),$$

where $\theta_{cal}$ represents the calibrated phase value, $Q_{non-calibrated}$ represents the non-calibrated quadrature component, and $I_{non-calibrated}$ represents the non-calibrated in-phase component.

In another aspect of the present disclosure, the memory stores further instructions that, when executed by the processor, cause the processor to compute the calibrated in-phase component according to the equation:

$$I_{calibrated} = I_{non-calibrated} \times \cos(\theta_{cal}) + Q_{non-calibrated} \times \sin(\theta_{cal}),$$

where $I_{calibrated}$ represents the calibrated in-phase component, $I_{non-calibrated}$ represents the non-calibrated in-phase component, $\theta_{cal}$ represents the calibrated phase value, and $Q_{non-calibrated}$ represents the non-calibrated quadrature component.

In a further aspect of the present disclosure, the memory further stores instructions that, when executed by the processor, cause the processor to compute the calibrated quadrature component according to the equation:

$$Q_{calibrated} = -I_{non-calibrated} \times \sin(\theta_{cal}) + Q_{non-calibrated} \times \cos(\theta_{cal}),$$

where $Q_{calibrated}$ represents the calibrated quadrature component, $I_{non-calibrated}$ represents the non-calibrated in-phase component, $\theta_{cal}$ represents the calibrated phase value, and $Q_{non-calibrated}$ represents the non-calibrated quadrature component.

In yet another aspect of the present disclosure, the memory further stores instructions that, when executed by the processor, cause the processor to compute the calibrated magnitude value according to the equation:

$$M_{cal} = \frac{1}{I_{calibrated}},$$

where $M_{cal}$ represents the calibrated magnitude value and $I_{calibrated}$ represents the calibrated in-phase component.

In another aspect of the present disclosure, the memory further stores instructions that, when executed by the processor, cause the processor to determine whether the calibrated magnitude value is less than zero, and, in response to a determination that the calibrated magnitude value is less than zero: (1) compute a second calibrated phase value, and (2) recompute the calibrated magnitude value, the calibrated in-phase component, and the calibrated quadrature component based on the second calibrated phase value.

In still a further aspect of the present disclosure, the memory stores further instructions that, when executed by the processor, cause the processor to determine whether the calibrated magnitude value is less than zero and whether the calibrated phase value is less than or equal to zero; and, in response to a determination that the calibrated magnitude value is less than zero and the calibrated phase value is less than or equal to zero: (1) compute a second calibrated phase value according to the equation:

$$\theta_{cal}' = \theta_{cal} + \pi,$$

where $\theta_{cal}'$ represents the second calibrated phase value and $\theta_{cal}$ represents the calibrated phase value; and (2) recompute the calibrated magnitude value, the calibrated in-phase component, and the calibrated quadrature component based on the second calibrated phase value.

In another aspect of the present disclosure, the memory further stores instructions that, when executed by the processor, cause the processor to determine whether the calibrated magnitude value is less than zero and whether the calibrated phase value is greater than zero; and, in response to a determination that the calibrated magnitude value is less than zero and the calibrated phase value is greater than zero: (1) compute a second calibrated phase value according to the equation:

$$\theta_{cal}' = \theta_{cal} - \pi,$$

where $\theta_{cal}'$ represents the second calibrated phase value and $\theta_{cal}$ represents the calibrated phase value; and (2) recompute the calibrated magnitude value, the calibrated in-phase component, and the calibrated quadrature component based on the second calibrated phase value.

In yet another aspect of the present disclosure, the memory further stores instructions that, when executed by the processor, cause the processor to: (1) receive a second signal having a second magnitude value and a second phase value; (2) compute a second non-calibrated in-phase component and a second non-calibrated quadrature component based on the second magnitude value and the second phase value; and (3) compute a corrected in-phase component and a corrected quadrature component based on the calibrated phase value, the calibrated magnitude value, the second non-calibrated in-phase component, and the second non-calibrated quadrature component.

In a further aspect of the present disclosure, the memory further stores instructions that, when executed by the processor, cause the processor to compute the corrected in-phase component according to the equation:

$$I_c = M_{cal} \times ((I_{non-cal2}) \times \cos(\theta_{cal}) + (Q_{non-cal2}) \times \sin(\theta_{cal})),$$

where $I_c$ represents the corrected in-phase component, $M_{cal}$ represents the calibrated magnitude value, $I_{non-cal2}$ represents the second non-calibrated in-phase component, $\theta_{cal}$ represents the calibrated phase value, and $Q_{non-cal2}$ represents the second non-calibrated quadrature component.

In another aspect of the present disclosure, the memory stores further instructions that, when executed by the processor, cause the processor to compute the corrected quadrature component according to the equation:

$$Q_c = M_{cal} \times (-(I_{non-cal2}) \times \sin(\theta_{cal}) + (Q_{non-cal2}) \times \cos(\theta_{cal})),$$

where $Q_c$ represents the corrected quadrature component, $M_{cal}$ represents the calibrated magnitude value, $I_{non-cal2}$ represents the second non-calibrated in-phase component, $\theta_{cal}$ represents the calibrated phase value, and $Q_{non-cal2}$ represents the second non-calibrated quadrature component.

In accordance with another aspect of the present disclosure, a system including an antenna assembly for calibrating an electromagnetic navigation system is provided. The antenna assembly includes a substrate, multiple pairs of transmit coils, multiple pairs of receive coils, multiple input terminals, and multiple output terminals. The substrate includes multiple layers, with each of the transmit coils being deposited on a respective one of the layers and each of the receive coils being deposited on another respective one of the layers. Each of the pairs of transmit coils corresponds to a respective pair of receive coils. The multiple input terminals are coupled to the multiple pairs of transmit coils, respectively, and the multiple output terminals are coupled to the multiple pairs of receive coils, respectively.

In another aspect of the present disclosure, the system further includes a computing device having a processor and a memory. The processor is coupled to the pairs of transmit coils by way of the input terminals, respectively, and is also coupled to the pairs of receive coils by way of the output terminals, respectively. The memory includes instructions that, when executed by the processor, cause the processor to: (1) transmit, by way of at least one of the pairs of transmit coils, a signal having a first magnitude value and a first phase value; (2) receive the signal by way of at least one of the pairs of receive coils; (3) compute a non-calibrated in-phase component and a non-calibrated quadrature component based on the first magnitude value and the first phase value; (4) compute a calibrated phase value based on the non-calibrated in-phase component and the non-calibrated quadrature component; (5) compute a calibrated in-phase component based on the calibrated phase value, the non-calibrated in-phase component, and the non-calibrated quadrature component; (6) compute a calibrated quadrature component based on the calibrated phase value, the non-calibrated in-phase component, and the non-calibrated quadrature component; (7) compute a calibrated magnitude value based on the calibrated in-phase component; and (8) store the calibrated phase value and the calibrated magnitude value in a table for use during an electromagnetic navigation procedure.

In yet another aspect of the present disclosure, each of the pairs of receive coils includes a first receive coil, deposited on a first layer of the plurality of layers, and a second receive coil, deposited on a second layer of the plurality of layers, with the first layer and the second layer each being located between a pair of the layers on which the corresponding pair of transmit coils are respectively deposited.

In accordance with yet a further aspect of the present disclosure, a method for optimizing an electromagnetic navigation system is provided. The method includes generating multiple test signals corresponding to multiple combinations of phase offset values of multiple frequency components, respectively. Based on the test signals, a table is generated, the table including multiple peak signal amplitudes associated with the multiple test signals, respectively. A minimum value of the stored peak signal amplitudes is identified in the table. Based on the table, a determination is made as to which one of the combinations of phase offset values is associated with the minimum value of the stored peak signal amplitudes. The determined combination of phase offset values is stored in a memory for use, during an electromagnetic navigation procedure, in generating a signal including the frequency components having the determined combination of phase offset values, respectively.

In another aspect of the present disclosure, as part of the method, the generating the multiple test signals includes, for each of the combinations of phase offset values, respectively: (1) generating a test signal including the frequency components having the respective combination of phase offset values, respectively; and (2) transmitting the test signal by way of a transmitting antenna.

In a further aspect of the present disclosure, the method further includes, for each of the combinations of phase offset values, respectively: (1) receiving the test signal by way of a receiving antenna; (2) capturing, during a sampling window, a sample of the received test signal; (3) measuring a peak signal amplitude of the captured sample; and (4) storing, in the table, the peak signal amplitude in association with the respective combination of phase offset values.

In yet another aspect of the present disclosure, as part of the method, the generating the test signal, the transmitting the test signal, and/or the receiving the test signal is performed by way of computer-implemented simulation.

In still another aspect of the present disclosure, each of the combinations of phase offset values employed in the method includes multiple phase offset values that correspond to the multiple frequency components, respectively.

In another aspect of the present disclosure, the method further includes generating the multiple combinations of phase offset values based on the multiple frequency components and a phase offset step size. Each of the combinations of phase offset values includes a respective set of phase offset values that correspond to the set of frequency components, respectively, and each of the phase offset values has a value in a range from zero to a maximum value, in increments of the phase offset step size.

In a further aspect of the present disclosure, the method further includes, during the electromagnetic navigation procedure: (1) generating a second signal including the multiple frequency components having the determined combination of phase offset values, respectively; (2) amplifying the second signal so as to have a magnitude greater than a magnitude of the test signal; and (3) transmitting the second signal.

In yet another aspect of the present disclosure, the method further includes, during the electromagnetic navigation procedure, (1) receiving a second signal that includes the multiple frequency components having the determined combination of phase offset values, respectively; and (2) amplifying the second signal so as to have a magnitude greater than a magnitude of the test signal.

In accordance with another aspect of the present disclosure, a system for optimizing an electromagnetic navigation system is provided. The system includes a processor and a memory. The memory stores instructions that, when executed by the processor, cause the processor to: (1) generate multiple test signals corresponding to multiple combinations of phase offset values of multiple frequency components, respectively; (2) generate, based on the multiple test signals, a table that includes a plurality of peak signal amplitudes associated with the multiple test signals, respectively; (3) identify, in the table, a minimum value of the stored peak signal amplitudes; (4) determine, based on the table, which one of the plurality of combinations of phase offset values is associated with the minimum value of the stored peak signal amplitudes; and (5) store the determined combination of phase offset values in the memory for use, during an electromagnetic navigation procedure, in generating a signal including the multiple frequency components having the determined combination of phase offset values, respectively In another aspect of the present disclosure, the memory of the system further stores instructions that, when executed by the processor, cause the processor to generate the plurality of test signals by, for each of the combinations of phase offset values, respectively: (1) generating a test signal including the multiple frequency components having the respective combination of phase offset values; and (2) transmitting the test signal by way of a transmitting antenna.

In a further aspect of the present disclosure, the memory of the system further stores instructions that, when executed by the processor, cause the processor to, for each of the combinations of phase offset values, respectively: (1) receive the test signal by way of a receiving antenna; (2) capture a sample of the received test signal during a sampling window; (3) measure a peak signal amplitude of the captured sample; and (4) store, in the table, the peak signal amplitude in association with the respective combination of phase offset values.

In yet another aspect of the present disclosure, each of the combinations of phase offset values employed in the system includes multiple phase offset values that correspond to the multiple frequency components, respectively.

In another aspect of the present disclosure, the memory of the system further stores instructions that, when executed by the processor, cause the processor to generate the multiple combinations of phase offset values based on the multiple frequency components and a phase offset step size. In this example, each of the combinations of phase offset values includes a respective set of phase offset values corresponding to the set of frequency components, respectively, and each of the phase offset values has a value in a range from zero to a maximum value, in increments of the phase offset step size.

In a further aspect of the present disclosure, the memory further stores instructions that, when executed by the processor, cause the processor to, during the electromagnetic navigation procedure: (1) generate a second signal including the multiple frequency components having the determined combination of phase offset values, respectively; (2) amplify the second signal so as to have a magnitude greater than a magnitude of the test signal; and (3) transmit the second signal.

In yet another aspect of the present disclosure, the memory further stores instructions that, when executed by the processor, cause the processor to, during the electromagnetic navigation procedure: (1) receive a second signal that includes the multiple frequency components having the determined combination of phase offset values, respectively; and (2) amplify the second signal so as to have a magnitude greater than a magnitude of the test signal.

In accordance with another aspect of the present disclosure, a non-transitory computer-readable medium is provided. The computer-readable medium stores sequences of instructions that, when executed by a processor, cause the processor to perform a method for optimizing an electromagnetic navigation system. The method includes generating multiple test signals corresponding to multiple combinations of phase offset values of multiple frequency components, respectively. Based on the multiple test signals, a table is generated, the table including multiple peak signal amplitudes associated with the multiple test signals, respectively. A minimum value of the stored peak signal amplitudes is identified in the table. Based on the table, a determination is made as to which one of the combinations of phase offset values is associated with the minimum value of the stored peak signal amplitudes. The determined combination of phase offset values is stored in a memory for use, during an electromagnetic navigation procedure, in generating a signal including the frequency components having the determined combination of phase offset values, respectively In another aspect of the present disclosure, the non-transitory computer-readable medium further stores sequences of instructions that cause the generating of the test signals to include, for each of the combinations of phase offset values, respectively: (1) generating a test signal including the frequency components having the respective combination of phase offset values; and (2) transmitting the test signal by way of a transmitting antenna.

In a further aspect of the present disclosure, the computer-readable medium further stores sequences of instructions that, when executed by the processor, cause the processor to, for each of the combinations of phase offset values, respectively: (1) receive the test signal by way of a receiving antenna; (2) capture a sample of the received test signal during a sampling window; (3) measure a peak signal amplitude of the captured sample; and (4) store the peak signal amplitude in the table in association with the respective combination of phase offset values.

In yet another aspect of the present disclosure, each of the combinations of phase offset values includes multiple phase offset values that correspond to the multiple frequency components, respectively.

In still a further aspect of the present disclosure, the computer readable medium further stores sequences of instructions that, when executed by the processor, cause the processor to generate the combinations of phase offset values based on the multiple frequency components and a phase offset step size. In this example, each of the combinations of phase offset values includes a respective set of phase offset values that correspond to the set of frequency components, respectively, and each of the phase offset values has a value in a range from zero to a maximum value, in increments of the phase offset step size.

Any of the above aspects and embodiments of the present disclosure may be combined without departing from the scope of the present disclosure.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Objects and features of the presently disclosed systems and methods will become apparent to those of ordinary skill in the art when descriptions of various embodiments are read with reference to the accompanying drawings, of which:

FIG. 6A, FIG. 6B, and FIG. 6C (collectively, FIG. 6) illustrate an example frequency multiplexed electromagnetic signal, and results of applying a filter and an FFT to the signal in a non-calibrated electromagnetic navigation system, in accordance with the present disclosure;

FIG. 7A, FIG. 7B, and FIG. 7C (collectively, FIG. 7) illustrate an example frequency multiplexed electromagnetic signal, and results of applying a filter and an FFT to the signal in a calibrated electromagnetic navigation system, in accordance with the present disclosure;

FIG. 9A, FIG. 9B, and FIG. 9C (collectively, FIG. 9) illustrate aspects of an example antenna assembly of a system for calibrating an electromagnetic navigation system, in accordance with an embodiment of the present disclosure;

DETAILED DESCRIPTION

The present disclosure is related to systems and methods for calibrating and/or optimizing an electromagnetic navigation system. The systems and methods herein may be employed to render electromagnetic navigation systems less susceptible to various sensor or antenna inductances, signal chain delays, and/or any delay from when the synchronization pulse occurs to when the acquisition or electromagnetic field generation actually begins, which may otherwise cause the sampled electromagnetic signal captured during the sampling window to not include a perfect cosine (or sine) waveform. The systems and methods herein also may be employed to render electromagnetic navigation systems less susceptible to variations in output current level(s) of transmitter channel(s) and/or in the gain(s) of receiver channel circuitry, which may otherwise cause the amplitude of the sampled electromagnetic signal captured at a particular location and orientation within the sensing volume relative to the field generating antenna assembly to vary from system to system.

Additionally, the systems and methods herein may be employed to calibrate an initial electromagnetic navigation system and multiple other systems to a common baseline, thereby facilitating the reuse, in the multiple other electromagnetic navigation systems, of a mapping of electromagnetic signal measurements at respective sensor locations in the sensing volume that was previously generated based on the initial electromagnetic navigation system.

Figure 1:
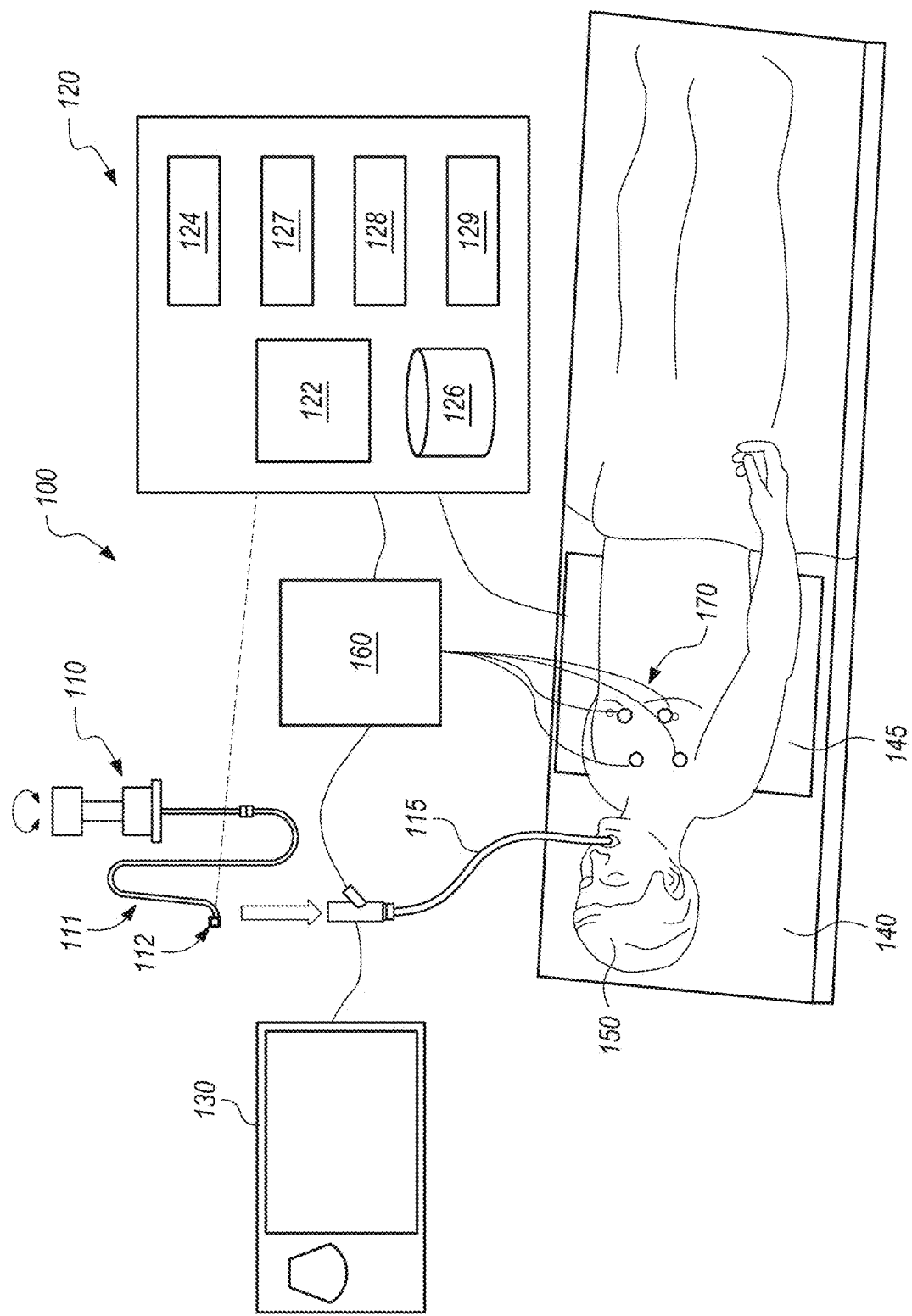
FIG. 1 shows an example electromagnetic navigation system, in accordance with the present disclosure.

FIG. 1 illustrates an example electromagnetic navigation (EMN) system 100 provided in accordance with the present disclosure. In general, the EMN system 100 is configured to identify a location and/or an orientation of a medical device being navigated toward a target location within the patient's body by using, among other things, an antenna assembly that generates one or more electromagnetic fields that are sensed by a sensor affixed to the medical device. In some cases, the EMN system 100 is further configured to augment computed tomography (CT) images, magnetic resonance imaging (MRI) images, and/or fluoroscopic images employed during navigation of the medical device through the patient's body toward a target of interest, such as a deceased portion in a luminal network of the patient's lung.

The EMN system 100 includes a catheter guide assembly 110, a bronchoscope 115, a computing device 120, a monitoring device 130, a patient platform 140 (which may be referred to as an EM board), a tracking device 160, and reference sensors 170 (three sensors of which are sometimes collectively referred to as a patient sensor triplet (PST)). The bronchoscope 115 is operatively coupled to the computing device 120 (by way of the tracking device 160) and the monitoring device 130 via respective wired connections (as shown in FIG. 1) or wireless connections (not shown in FIG. 1).

During a navigation phase of an EMN bronchoscopy procedure, the bronchoscope 115 is inserted into the oral cavity of a patient 150 and captures images of the luminal network of the lung. The catheter guide assembly 110 is inserted into the bronchoscope 115 to access the periphery of the luminal network of the lung of the patient 150. The catheter guide assembly 110 may include a catheter or extended working channel (EWC) 111 with an EM sensor 112 affixed to a portion (for example, a distal portion) of the EWC 111. A locatable guide catheter (LG) may be inserted into the EWC 111 with another EM sensor (not shown in FIG. 1) affixed to a portion (for example, a distal portion) of the LG. The EM sensor 112 affixed to the EWC 111 or the EM sensor affixed to the LG is configured to receive a signal based on an electromagnetic field radiated by the antenna assembly 145 (a field generating antenna assembly), and based upon the received signal, is used to determine a location and/or an orientation of the EWC 111 or the LG during navigation through the luminal network of the lung.

The computing device 120, such as a laptop, desktop, tablet, or other suitable computing device, includes a display 122, one or more processors 124, one or more memories 126, an AC current driver 127 for providing AC current signals to the antenna assembly 145, a network interface controller 128, and one or more input devices 129. The particular configuration of the computing device 120 illustrated in FIG. 1 is provided as an example, but other configurations of the components shown in FIG. 1 as being included in the computing device 120 are also contemplated. In particular, in some embodiments, one or more of the components (122, 124, 126, 127, 128, and/or 129) shown in FIG. 1 as being included in the computing device 120 may instead be separate from the computing device 120 and may be coupled to the computing device 120 and/or to any other component(s) of the system 100 by way of one or more respective wired or wireless path(s) to facilitate the transmission of power and/or data signals throughout the system 100. For example, although not shown in FIG. 1, the AC current driver 127 may, in some example aspects, be separate from the computing device 120 and may be coupled to the antenna assembly 145 and/or coupled to one or more components of the computing device 120, such as the processor 124 and the memory 126, by way of one or more corresponding paths.

In some aspects, the EMN system 100 may also include multiple computing devices 120, wherein the multiple computing devices 120 are employed for planning, treatment, visualization, or helping clinicians in a manner suitable for medical operations. The display 122 may be touch-sensitive and/or voice-activated, enabling the display 122 to serve as both an input device and an output device. The display 122 may display two-dimensional (2D) images or three-dimensional (3D) images, such as a 3D model of a lung, to enable a practitioner to locate and identify a portion of the lung that displays symptoms of lung diseases.

The one or more memories 126 store one or more programs and/or computer-executable instructions that, when executed by the one or more processors 124, cause the one or more processors 124 to perform various functions and/or procedures. For example, the processors 124 may calculate a location and/or an orientation of the EM sensor 112 based on the electromagnetic signal that is radiated by the antenna assembly 145 and received by the EM sensor 112. The processors 124 may also perform image-processing functions to cause the 3D model of the lung to be displayed on the display 122. The processors 124 may also generate one or more electromagnetic signals to be radiated by way of the antenna assembly 145. In some embodiments, the computing device 120 may further include a separate graphic accelerator (not shown in FIG. 1) that performs only the image-processing functions so that the one or more processors 124 may be available for other programs. The one or more memories 126 also store data, such as mapping data for EMN, image data, patients' medical record data, prescription data, and/or data regarding a history of the patient's diseases, and/or other types of data.

The mapping data may link multiple grid points, in a coordinate system of an EM volume in which a medical device (e.g., the EWC 111, the LG, treatment probe, or another surgical device) navigates, to the EM signal characteristics (for example, signal strength) that correspond to the grid points, respectively. In this manner, when the EM sensor 112 senses an EM signal having certain characteristics at a particular grid point, the one or more processors 124 may compare the sensed EM signal characteristics to the EM signal characteristics in the mapping data and determine the location and/or orientation of the EM sensor 112 within the EM volume based on a result of the comparison.

As shown in FIG. 1, the platform 140 is configured to provide a flat surface upon which the patient 150 lies during the EMN navigation procedure. The antenna assembly 145, which may also be referred to as an EM field generating device, is arranged upon the platform 140 or is included as a component of the platform 140. The antenna assembly 145 includes one or more antennas, such as planar loop antennas (not shown in FIG. 1). Example aspects of the antenna assembly 145 are described in further detail below.

With the patient 150 lying upon the platform 140, the one or more processors 124 (or another signal generator not shown in FIG. 1) generate and provide to the antenna(s) of the antenna assembly 145 by way of the AC current driver 127 one or more AC current signals that the antenna(s) convert into one or more respective EM signal(s) and radiate in a manner sufficient to surround a portion of the patient 150. In some aspects, the antenna assembly 145 includes a connector that has at least two terminals, and the trace of the antenna (not shown in FIG. 1) has two ends that are coupled to the two connector terminals, respectively, to form a signal communication path from the one or more processors 145 to the antenna.

Having described an example EMN system 100, reference will now be made to FIG. 2, which is a flowchart illustrating an example procedure 200 for calibrating an EMN system such as the EMN system 100, in accordance with the present disclosure. As described in further detail below, aspects of the procedure 200 may be implemented by utilizing the antenna assembly 145 described herein in connection with FIG. 1 and/or the example antenna assembly of a system for calibrating an electromagnetic navigation system described below in connection with FIG. 9. In one example embodiment, the procedure 200 is implemented at least in part by a processor executing instructions stored by a memory.

At S201, a signal having a first magnitude value and a first phase value is transmitted or radiated by way of a transmitting antenna. In various example embodiments, the signal may be a frequency multiplexed signal having multiple frequency components, a time multiplexed signal to share a common transmit and/or receive channel, and/or a combination of a frequency multiplexed signal and a time multiplexed signal. In one embodiment, for example without limitation, three parallel transmit and receive channels may each be employed to transmit and receive frequency multiplexed signals each having three frequency components, yielding a total of nine frequency components.

At S202, the signal transmitted at S201 is received by way of a receiving antenna. In one example embodiment, although not expressly shown in FIG. 2, the transmitting at S201 and the receiving at S202 are synchronized to one another to enable consistent measurements of electromagnetic signals from one sampling window to another.

At S203 the signal received at S202 is amplified, for example by way of one or more receive channel amplifiers, and at S204 the amplified signal is digitized by way of an analog-to-digital converter (ADC).

Figure 3A:
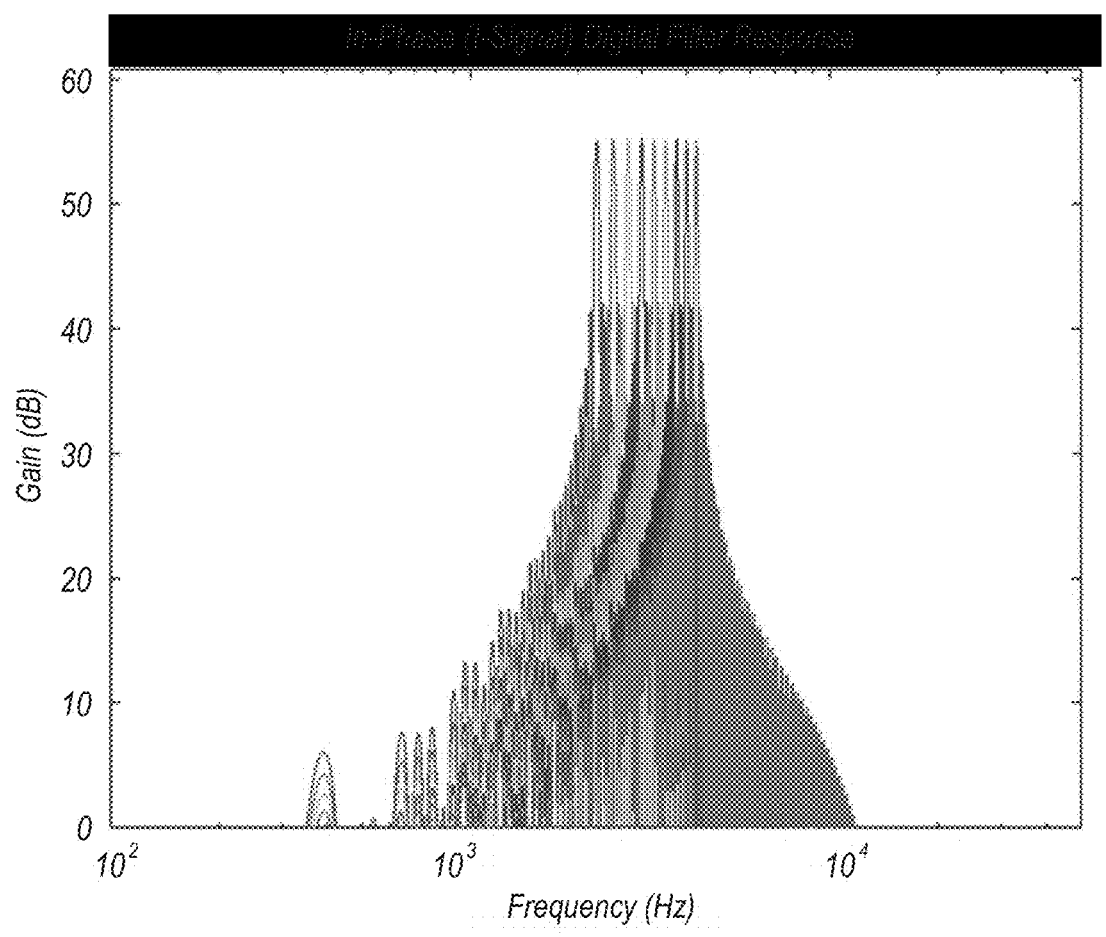
FIG. 3A and FIG. 3B (collectively, FIG. 3) depict example frequency responses of in-phase and quadrature digital filters, in accordance with the present disclosure.
Figure 3B:
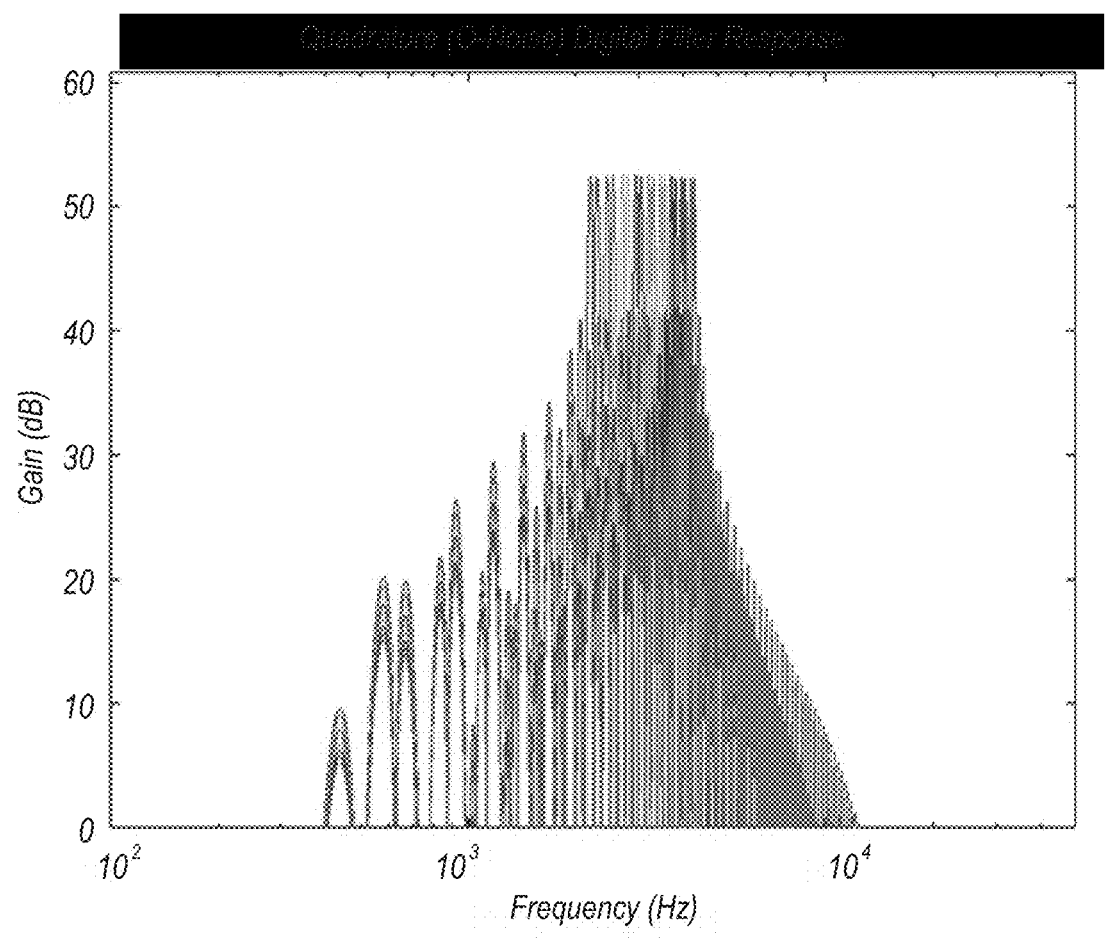

At S205, the signal digitized at S204 is filtered, for example by way of a digital filter. Example frequency responses of in-phase and quadrature digital filters are shown in FIG. 3A and FIG. 3B, respectively (collectively, FIG. 3). In particular, FIG. 3 shows example frequency responses of in-phase digital filters (FIG. 3A) and quadrature digital filters (FIG. 3B) configured as bandpass filters tuned to pass nine frequency channels of a frequency division multiplexed signal and to reject all other frequency signals. For clarity, the frequency responses of the bandpass filters are illustrated in FIG. 3A and FIG. 3B by way of lines having different colors, respectively. The number of frequency channels illustrated in FIG. 3 is provided by way of example and not limitation. Other numbers of frequency channels are contemplated within the scope of the present disclosure.

At S206, a magnitude and phase of the signal filtered at S205 are determined according to known techniques, such as by detecting a peak amplitude of the filtered signal and/or by measuring a phase of the filtered signal relative to a time of transmission of the signal or another temporal reference point.

Figure 4:
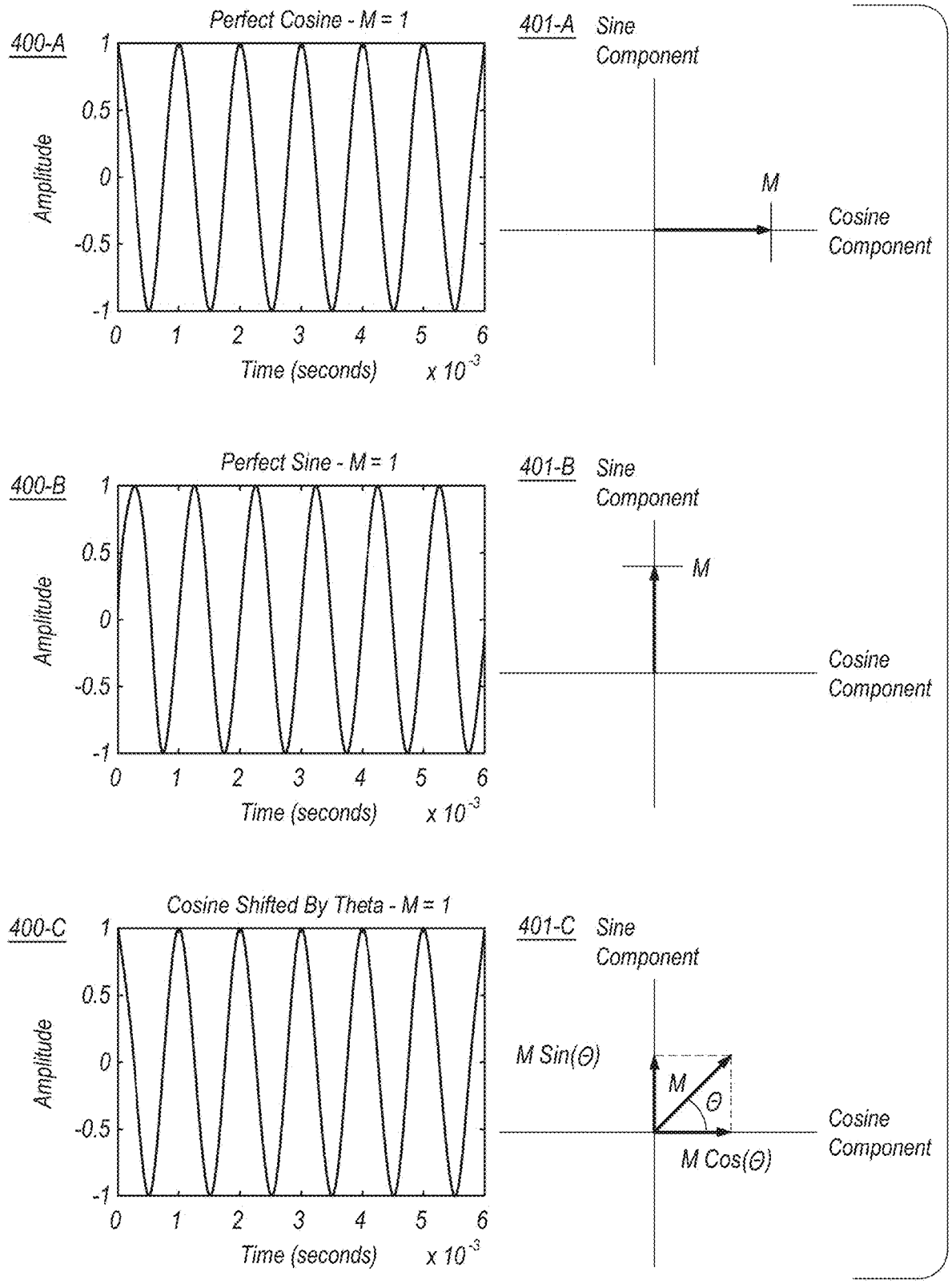
FIG. 4 illustrates example electromagnetic signals and the sine components and cosine components thereof, in accordance with the present disclosure.

At S207, a non-calibrated in-phase (I) component and a non-calibrated quadrature (Q) component of the signal are computed based on the magnitude value and the phase value determined at S206. FIG. 4 illustrates example electromagnetic signals and the in-phase components (e.g., cosine or signal component) and quadrature components (e.g., sine or noise components) thereof, in accordance with an aspect of the present disclosure. In particular, 400-A depicts an example sampled electromagnetic signal that includes a cosine waveform having a magnitude M and a phase offset of zero. 401-A is a graph illustrating that the in-phase component and quadrature component computed based on the waveform of 400-A have magnitudes of M and zero, respectively. 400-B depicts an example sampled electromagnetic signal that includes a sine waveform having a magnitude M and a phase offset of zero. 401-B is a graph illustrating that the in-phase component and quadrature component computed based on the waveform of 400-B have magnitudes of zero and M, respectively. 400-C depicts an example sampled electromagnetic signal that includes a cosine waveform having a magnitude M and having a phase offset of $\theta$. 401-C is a graph illustrating that the in-phase component and quadrature component computed based on the waveform of 400-C have magnitudes of $M \cos(\theta)$ and $M \sin(\theta)$, respectively.

In one example, the non-calibrated in-phase component is computed by performing a lookup in cosine table based on the magnitude value and the phase value determined at S206. For example, the cosine table may indicate a cosine component (or a non-calibrated in-phase component) for each combination of a magnitude and a phase value. Similarly, the non-calibrated quadrature component, in one example, is computed by performing a lookup in sine table based on the magnitude value and the phase value determined at S206. For example, the sine table may indicate a sine component (or a non-calibrated quadrature component) for each combination of a magnitude and a phase value.

At S208, a calibrated phase value is computed based on the non-calibrated in-phase component and the non-calibrated quadrature component computed at S207. In one example, the calibrated phase value is computed according to the equation:

$$\theta_{cal} = \tan^{-1}\left(\frac{Q_{non-calibrated}}{I_{non-calibrated}}\right) \quad (1)$$

where $\theta_{cal}$ represents the calibrated phase value, and $Q_{non-calibrated}$ and $I_{non-calibrated}$ represent the non-calibrated quadrature component and the non-calibrated in-phase component, respectively, computed at S207.

At S209, a calibrated in-phase component is computed based on the calibrated phase value computed at S208 and the non-calibrated in-phase component and the non-calibrated quadrature component computed at S207. In one example, the calibrated in-phase component is computed according to the equation:

$$I_{calibrated} = I_{non-calibrated} \times \cos(\theta_{cal}) + Q_{non-calibrated} \times \sin(\theta_{cal}) \quad (2)$$

where $I_{calibrated}$ represents the calibrated in-phase component, $\theta_{cal}$ represents the calibrated phase value computed at S208, and $I_{non-calibrated}$ and $Q_{non-calibrated}$ represent the non-calibrated in-phase component the non-calibrated quadrature component computed at S207.

At S210, a calibrated quadrature component is computed based on the calibrated phase value computed at S208 and the non-calibrated in-phase component and non-calibrated quadrature component computed at S207. In one example, the calibrated quadrature component is computed according to the equation:

$$Q_{calibrated} = -I_{non-calibrated} \times \sin(\theta_{cal}) + Q_{non-calibrated} \times \cos(\theta_{cal}) \quad (3)$$

where $Q_{calibrated}$ represents the calibrated quadrature component, $\theta_{cal}$ represents the calibrated phase value computed at S208, and $I_{non-calibrated}$ and $Q_{non-calibrated}$ represent the non-calibrated in-phase component and the non-calibrated quadrature component, respectively, computed at S207.

At S211, a calibrated magnitude value is computed based on the calibrated in-phase component computed at S209. In one example the calibrated magnitude value is computed according to the equation:

$$M_{cal} = \frac{1}{I_{calibrated}} \quad (4)$$

where $M_{cal}$ represents the calibrated magnitude value and $I_{calibrated}$ represents the calibrated in-phase component computed at S209.

In some example embodiments, a determination is made as to whether the calibrated magnitude value computed at S211 is less than zero, and, in response to a determination that the calibrated magnitude value is less than zero a second calibrated phase value is computed, and the calibrated magnitude value, the calibrated in-phase component, and the calibrated quadrature component are recomputed based on the second calibrated phase value.

For instance, at S212, a determination is made as to whether the calibrated magnitude value computed at S211 is less than zero and whether the calibrated phase value computed at S208 is less than or equal to zero. If it is determined at S212 that the calibrated magnitude value is less than zero and the calibrated phase value is less than or equal to zero, then at S213 a second calibrated phase value is computed according to the equation:

$$\theta_{cal}' = \theta_{cal} + \pi \quad (5)$$

where $\theta_{cal}'$ represents the second calibrated phase value, and $\theta_{cal}$ represents the calibrated phase value computed at S208. For convenience, the phase values and equations herein are described in terms of radians, although one of skill in the art would appreciate how to describe the phase values and equations herein in terms of degrees instead of radians. The procedures of S207 through S211 are then repeated (for example, the calibrated in-phase component, and the calibrated quadrature component are recomputed) based on the second calibrated phase value computed at S213.

At S214, a determination is made as to whether the calibrated magnitude value computed at S211 is less than zero and whether the calibrated phase value computed at S208 is greater than zero. If it is determined at S214 that the calibrated magnitude value is less than zero and the calibrated phase value is greater than zero, then at S215 a second calibrated phase value is computed according to the equation:

$$\theta_{cal}' = \theta_{cal} - \pi \quad (6)$$

where $\theta_{cal}'$ represents the second calibrated phase value and $\theta_{cal}$ represents the calibrated phase value. The procedures of S207 through S212 are then repeated (for example, the calibrated magnitude value, the calibrated in-phase component, and the calibrated quadrature component are recomputed) based on the second calibrated phase value computed at S215.

At S216, the calibrated phase value computed at S208 and the calibrated magnitude value computed at S211 are stored in association with one another in a table (for example, in a memory) for use during an electromagnetic navigation procedure. Table 1 below illustrates an example of a table that may be populated with calibrated phase values and calibrated magnitude values computed at S208 and S211, respectively, and stored at S216, for an example system having 9 frequencies or channels.

TABLE 1

| Frequency/Channel Index | $M_{cal}$ | $\theta_{cal}$ (radians or degrees) |
|---|---|---|
| 1 | $M_{cal1}$ | $\theta_{cal1}$ |
| 2 | $M_{cal2}$ | $\theta_{cal2}$ |
| 3 | $M_{cal3}$ | $\theta_{cal3}$ |
| 4 | $M_{cal4}$ | $\theta_{cal4}$ |
| 5 | $M_{cal5}$ | $\theta_{cal5}$ |
| 6 | $M_{cal6}$ | $\theta_{cal6}$ |
| 7 | $M_{cal7}$ | $\theta_{cal7}$ |
| 8 | $M_{cal8}$ | $\theta_{cal8}$ |
| 9 | $M_{cal9}$ | $\theta_{cal9}$ |

At S217, a determination is made as to whether steps of the calibration procedure 200 are to be repeated for an additional frequency (for instance, another frequency component of a frequency division multiplexed signal) and/or an additional channel (for instance, an additional parallel channel of a multiple channel antenna assembly system). If it is determined at S217 that steps of the calibration procedure 200 are to be repeated for an additional frequency and/or channel, then at S218 a frequency index and/or a channel index is incremented, and the procedures of S201 through S217 are repeated for an additional frequency and/or channel.

At S219, the calibrated phase value and the calibrated magnitude value stored at S216 are utilized in an electromagnetic navigation procedure. For instance, in one example, during the electromagnetic navigation procedure, a second signal having a second magnitude value and a second phase value is generated, transmitted and received in the manner described above in connection with S201 and S202. A second non-calibrated in-phase component and a second non-calibrated quadrature component are computed based on the second magnitude value and the second phase value. A corrected in-phase component and a corrected quadrature component are then computed based on the computed calibrated phase value, calibrated magnitude value, second non-calibrated in-phase component, and second non-calibrated quadrature component. In one example, the corrected in-phase component is computed according to the equation:

$$I_c = M_{cal} \times ((I_{non-cal2}) \times \cos(\theta_{cal}) + (Q_{non-cal2}) \times \sin(\theta_{cal})) \quad (7)$$

and the corrected quadrature component is computed according to the equation:

$$Q_c = M_{cal} \times (-(I_{non-cal2}) \times \sin(\theta_{cal}) + (Q_{non-cal2}) \times \cos(\theta_{cal})) \quad (8)$$

where $I_c$ represents the corrected in-phase component, $M_{cal}$ represents the calibrated magnitude value, $I_{non-cal2}$ represents the second non-calibrated in-phase component, $\theta_{cal}$ represents the calibrated phase value, $Q_{non-cal2}$ represents the second non-calibrated quadrature component, and $Q_c$ represents the corrected quadrature component.

As can be appreciated in view of the present disclosure, the calibration procedure 200 described herein can be employed to calibrate an electromagnetic navigation system, for instance, (1) to reduce the sensitivity of the electromagnetic navigation system to sources of inconsistency, such as sensor or antenna inductances, signal chain delays, and/or delays from when the synchronization pulse occurs to when the acquisition or electromagnetic field generation actually begins—that may otherwise cause a sampled electromagnetic signal captured during the sampling to not include a perfect cosine (or sine) waveform. Also, the calibration procedure 200 can also be employed to calibrate an electromagnetic navigation system to reduce its sensitivity to variations in the output current level(s) of transmitter channel(s) and/or in the gain(s) of receiver channel circuitry, which may otherwise cause the amplitude of the sampled electromagnetic signal captured at a particular location and orientation within the sensing volume relative to the field generating antenna assembly to vary from system to system. Additionally, the calibration procedure 200 may be employed to calibrate multiple electromagnetic navigation systems (for instance, being based on similar or substantially identical field generating antenna assembly 145 designs) to be calibrated to a common baseline, thereby enabling reuse in multiple electromagnetic navigation systems of a mapping that was previously generated based on an initial electromagnetic navigation system, avoiding the need to generate new mappings of electromagnetic signal measurements at respective sensor locations in the sensing volume for each electromagnetic navigation system.

Figure 5A:
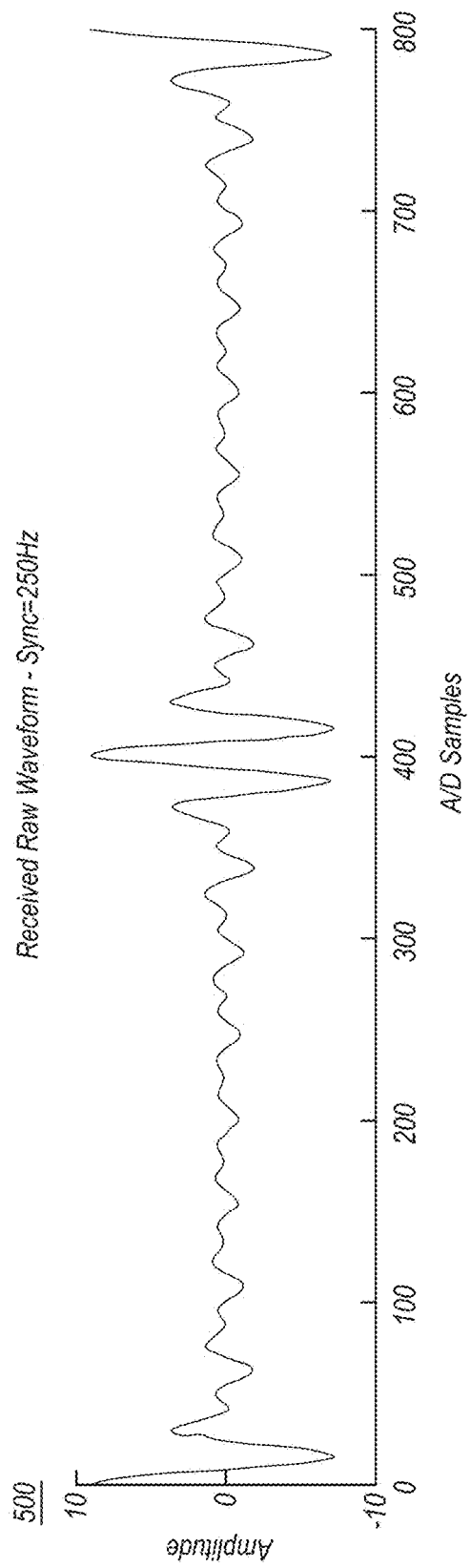
FIG. 5A, FIG. 5B, and FIG. 5C (collectively, FIG. 5) illustrate an example frequency multiplexed electromagnetic signal, and results of applying a filter and a Fast Fourier Transform (FFT) to the signal in an example electromagnetic navigation system, in accordance with the present disclosure.
Figure 5B:
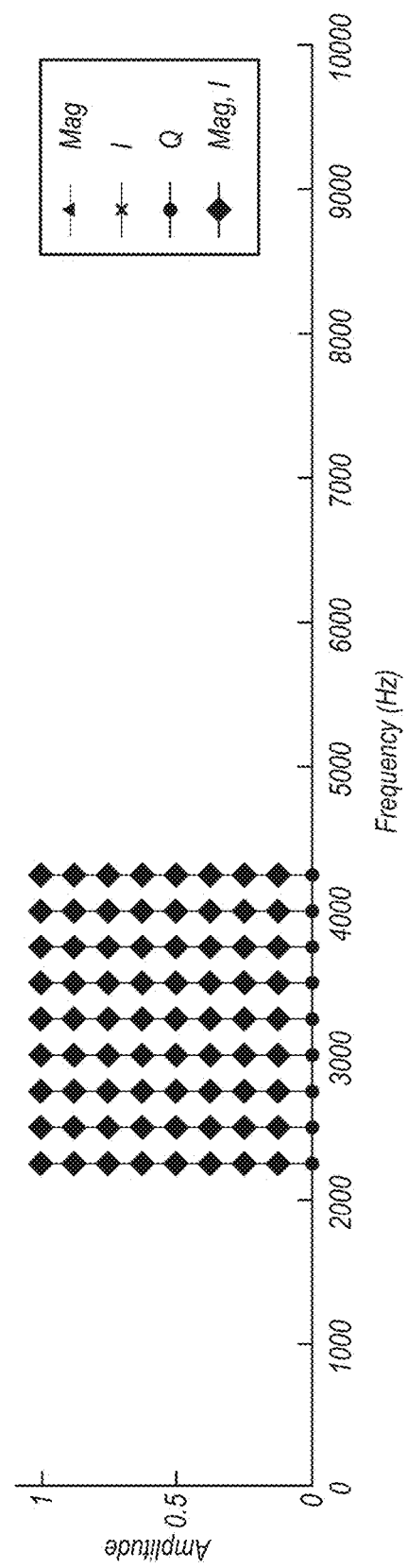
Figure 5C:
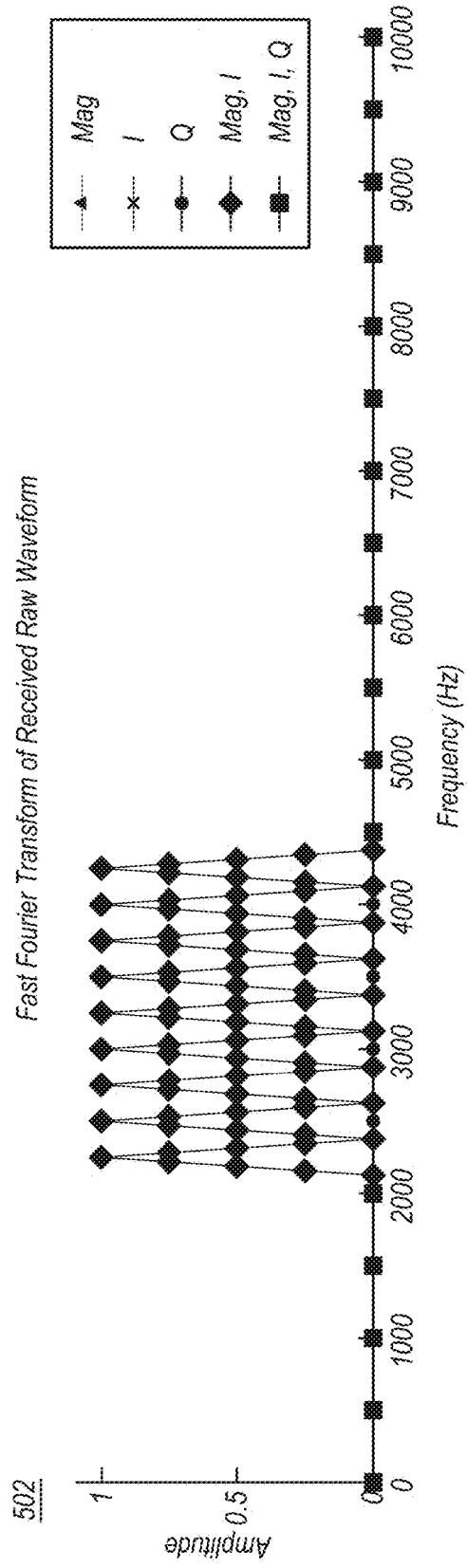

Having described an example procedure 200 for calibrating an electromagnetic navigation system, reference will now be made to FIGS. 5 through 7, which illustrate an example frequency multiplexed electromagnetic signal, and results of applying a filter and an FFT to the signal in various example electromagnetic navigation systems, in accordance with aspects of the present disclosure. In particular, graph 500 of FIG. 5A shows a captured sample of an example frequency division multiplexed (FDM) electromagnetic signal that includes nine cosine functions each having a different frequency (frequency components) and each having an amplitude of 1. In addition to magnitude values, graph 501 of FIG. 5B illustrates the in-phase (I) components and quadrature (Q) components that are computed, in a model electromagnetic navigation system, based on the signal shown in graph 500 after the signal has been filtered, for example, by way of in-phase and quadrature digital filters having the example frequency responses shown in FIG. 3. Graph 502 in FIG. 5C illustrates a result of applying an FFT to the signal shown in graph 500 in the model electromagnetic navigation system. As can be seen in graph 501, each of the nine frequency components has magnitude and in-phase component values of 1 and a quadrature component value of zero.

Figure 6A:
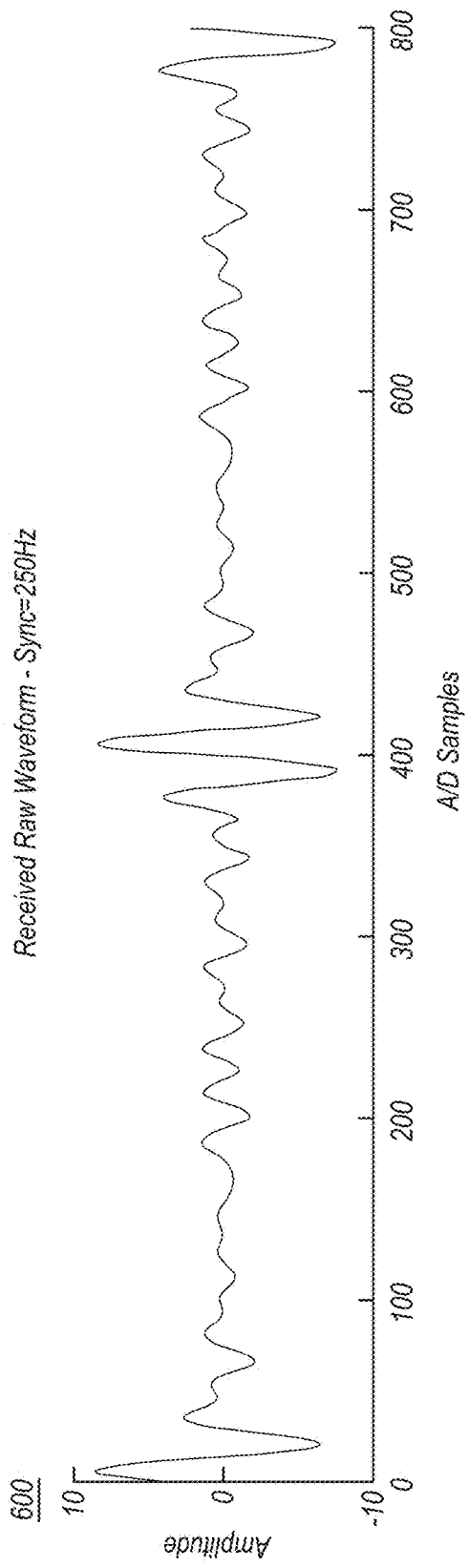

Graph 600 of FIG. 6A and graph 700 of FIG. 7A each show a captured sample of an example frequency division multiplexed (FDM) electromagnetic signal that includes nine cosine functions that are each intended to have a different frequency (frequency components) and an amplitude of 1, but due to variations and imperfections in the system, may have variations in amplitude and phase offset. In addition to magnitude values, graph 601 of FIG. 6B illustrates the in-phase (I) components and quadrature (Q) components that are computed, in a non-calibrated electromagnetic navigation system (e.g., a system that has not been calibrated based on the calibration procedure 200), based on the signal shown in graph 600A after the signal has been filtered. Graph 602 in FIG. 6C illustrates a result of applying an FFT to the signal shown in graph 600 in the non-calibrated electromagnetic navigation system. As can be seen in graph 601, the nine frequency components each have a magnitude value of 1 but have varying in-phase and quadrature component values, due to the variations or imperfections in the captured signal.

Figure 7C:
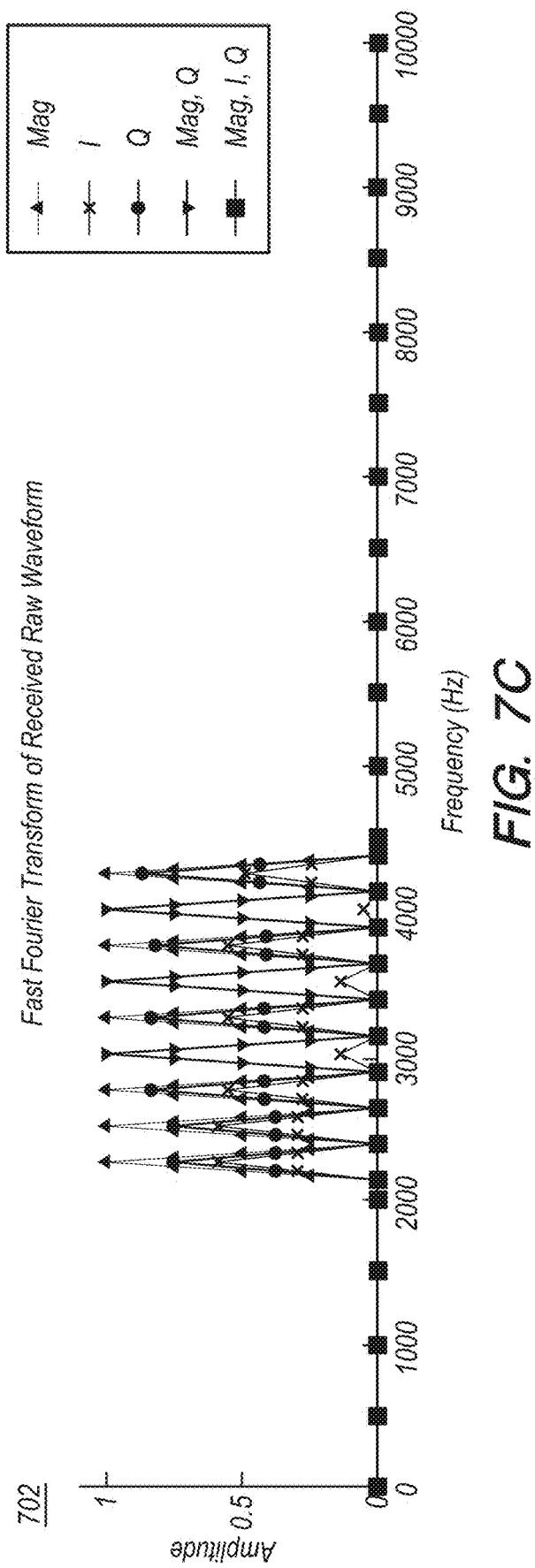

In addition to magnitude values, graph 701 of FIG. 7B illustrates the in-phase (I) components and quadrature (Q) components that are computed, in a calibrated electromagnetic navigation system (e.g., a system that has been calibrated based on the calibration procedure 200), based on the signal shown in graph 600 after the signal has been filtered. Graph 702 in FIG. 7C illustrates a result of applying an FFT to the signal shown in graph 600 in the calibrated electromagnetic navigation system. As can be seen in graph 701, each of the nine frequency components has magnitude and in-phase component values of 1 and a quadrature component value of zero, despite the imperfections in the captured signal.

Figure 8:
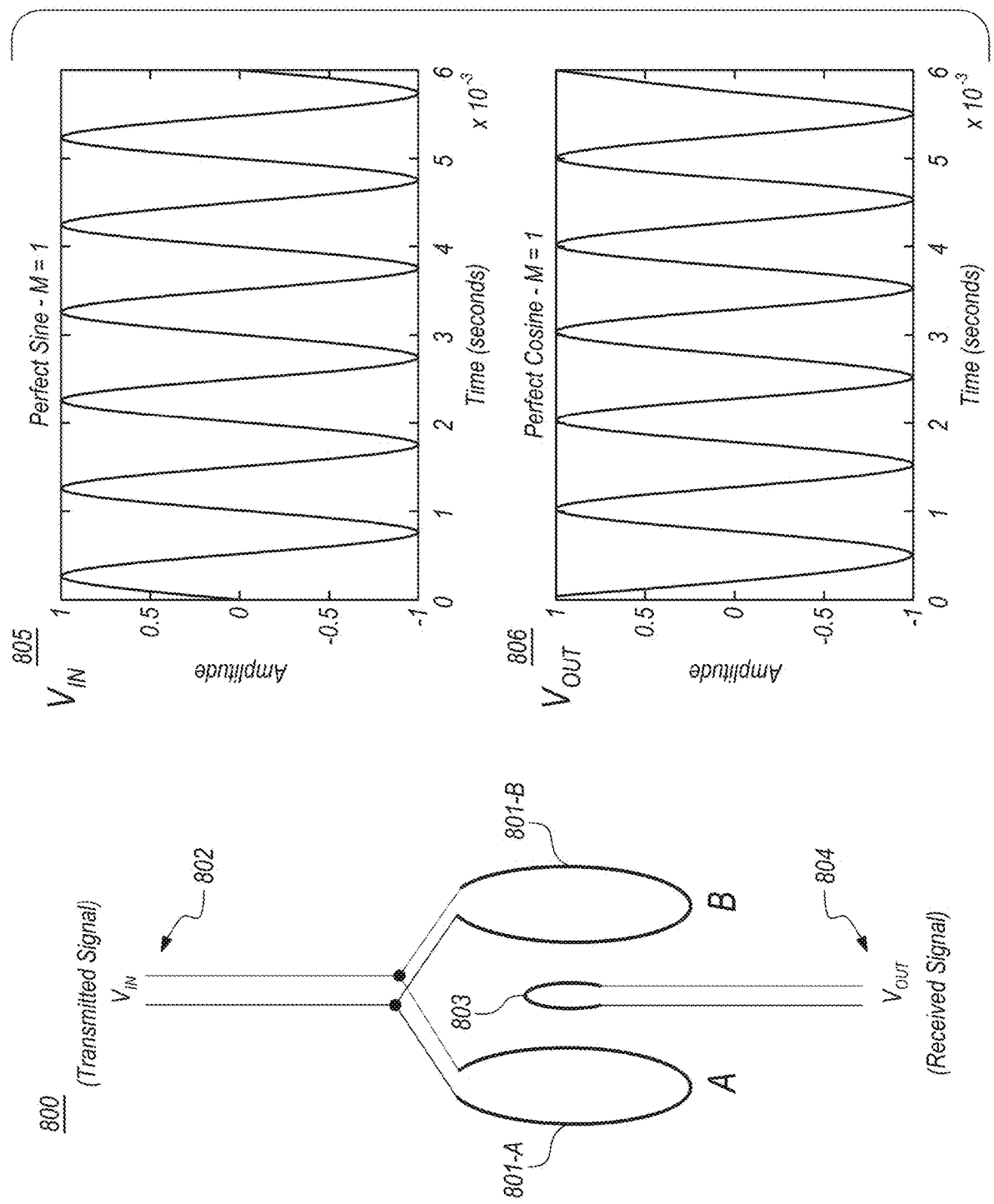
FIG. 8 shows a diagram of an example Helmholtz coil and corresponding example input and output voltage waveforms, in accordance with the present disclosure.

Reference will now be made to FIG. 8 and FIG. 9, which illustrate aspects of an example system for calibrating electromagnetic navigation systems, in accordance with the present disclosure. In particular, FIG. 8 shows a diagram of an example circuit 800 that includes a pair of transmitting coils 801-A and 801-B (collectively 801) (which may be, in some examples, a Helmholtz pair) coupled to an input terminal 802 (which in this example includes two conductors, but may in some embodiments include any number of conductors), a corresponding receive coil 803 coupled to an output terminal 804 (which in this example includes two conductors, but may in some embodiments include any number of conductors). Although the circuit 800 of FIG. 8 includes a single receive coil 803, this is merely provided as an example. As described in further detail below, other example embodiments are contemplated in which the circuit 800 includes multiple receive coils per receive channel, for example, multiple receive coils or receive coil pairs coupled to one another in a series circuit. The graph 805 illustrates an example input voltage signal (or waveform) that may be applied to the pair of transmit coils 801 by way of the input terminal 802, thereby causing the transmit coils 801 to radiate an electromagnetic field. In the example of graph 805, the input voltage signal is a sine waveform. The graph 806 illustrates an example output voltage signal (or waveform) that the radiated electromagnetic field may induce in the output terminal 804 by way of the receive coil 803. In the example of graph 806, the output voltage signal, which is induced based on the input sine waveform, is a cosine waveform. As described in further detail below, one or more circuits such as the circuit 800 may be included in an antenna assembly for calibrating an electromagnetic navigation system, in accordance with aspects of the present disclosure.

FIG. 9A, FIG. 9B, and FIG. 9C (collectively, FIG. 9) illustrate aspects of an example antenna assembly 903 that may be included in a system for calibrating an electromagnetic navigation system, such as the electromagnetic navigation system 100, in accordance with the present disclosure. Although not shown in FIG. 9, in some embodiments, the system for calibrating the electromagnetic navigation system includes several of the components that are described above in connection with FIG. 1, such as for example the computing device 120, the tracking module 160, the patient platform 140, and/or other components. In some embodiments, the system for calibrating an electromagnetic navigation system may employ the field generating antenna assembly 145 and the EM sensor 112 to calibrate one or more transmit and receive channel(s) of the electromagnetic navigation system 100, for instance according to the procedure 200 described herein. In other embodiments, in lieu of the field generating antenna assembly 145 and the EM sensor 112, the system for calibrating the electromagnetic navigation system includes the antenna assembly 903 of FIG. 9C, which includes one or more circuits, such as the circuit 800 of FIG. 8, each configured to be employed to calibrate a corresponding transmit and/or receive channel of the electromagnetic navigation system 100, for instance according to the procedure 200 described herein. In some examples, the computing device 120 is coupled to the antenna assembly 903 by way of transmit and receive channels thereof, and is configured to transmit and receive signals by way of the transmit and receive channels, respectively, to calibrate each transmit and receive channel.

With reference to FIG. 9C, a top view of the example antenna assembly 903 as fully fabricated is shown. In some embodiments, the antenna assembly 903 includes a substrate having multiple layers. FIG. 9A shows an exploded view 901 of the antenna assembly 903 that illustrates an example arrangement of the multiple layers of the substrate of the antenna assembly 903 (which arrangement may be referred to as a printed circuit board (PCB) stackup). The arrangement of the multiple layers of the substrate of the antenna assembly 903 that is shown in view 901 is provided as one example PCB stackup, but other PCB stackups are contemplated, for instance, with channels having single-receive-coil configurations and/or channels having multiple-receive-coil configurations, as described in further detail below.

FIG. 9B shows a plan view 902 of a single layer of the antenna assembly 903. The antenna assembly 903 includes multiple pairs of transmit coils and multiple receive coils (and/or receive coil pairs, not explicitly shown in FIG. 9), with each pair of transmit coils corresponding to a respective one of the receive coils (or receive coil pairs). In one embodiment, each set of a pair of transmit coils and a corresponding receive coil (or receive coil pair) corresponds to a particular transmit and receive channel (or a particular transmit and receive frequency) of the electromagnetic navigation system being calibrated. For instance, for an electromagnetic navigation system that includes N transmit channels and N receive channels, the antenna assembly 903 includes N pairs of transmit coils and N corresponding receive coils and/or receive coil pairs, respectively.

Although not explicitly shown in the view 901, in some example embodiments, each set of a pair of transmit coils and a corresponding receive coil of the antenna assembly 903 (for instance the pair of transmit coils $801\text{-}A_1$, $801\text{-}B_1$ and the corresponding receive coil $803_1$ shown in view 901) is formed as the pair of transmitting coils 801 (which may be, in some examples, a Helmholtz pair) and the corresponding receive coil 803 shown in FIG. 8. More particularly, with reference to the view 901, the pair of transmit coils $801\text{-}A_1$ and $801\text{-}B_1$ corresponds to the receive coil $803_1$, the pair of transmit coils $801\text{-}A_N$ and $801\text{-}B_N$ corresponds to the receive coil $803_N$, and so forth. Each pair of transmitting coils 801 is coupled, via printed circuit board pads, traces, and/or vias for example (not explicitly shown in FIG. 9), to a corresponding input terminal $802_1$ through $802_N$, respectively, and each receive coil (or, in some examples, each receive coil pair) $803_1$ through $803_N$ is coupled, via printed circuit board pads, traces, and/or vias for example (not explicitly shown in FIG. 9), to a corresponding output terminal $804_1$ through $804_N$, respectively. In this way, the computing device 120 can be coupled to particular coils of the transmit coils 801 and the receive coils 803 by way of respective terminals of the input terminals 802 and the output terminals 804.

As noted above, in various example embodiments, the antenna assembly 903 may include a single receive coil per channel (which is referred to as a single-receive-coil configuration) or multiple receive coils per channel (which is referred to as a multiple-receive-coil configuration). The example arrangement of the multiple layers of the substrate of the antenna assembly 903 shown in the view 901 illustrates a single-receive-coil configuration, where each channel has a single receive coil $803_1$ through $803_N$, respectively. As indicated in the view 901, each of the transmit coils (transmit coil $801\text{-}A_1$ through transmit coil $801\text{-}A_N$ and transmit coil $801\text{-}B_1$ through transmit coil $801\text{-}B_N$) is deposited on a respective one of the layers of the substrate, and each of the receive coils (receive coil $803_1$ through receive coil $803_N$) is deposited on a respective one of the layers of the substrate. In the example arrangement of view 901, each of the receive coils $803_1$ through $803_N$ is arranged on a respective one of the substrate layers located in between (though not necessarily immediately adjacent to) the pair of substrate layers upon which the corresponding pair of transmit coils 801 are respectively deposited. For instance, in the single-receive-coil configuration, the receive coil $803_1$ is arranged on a substrate layer located in between the pair of substrate layers upon which the corresponding pair of transmit coils $801\text{-}A_1$ and $801\text{-}B_1$ are respectively deposited; and the receive coil $803_N$ is arranged on a substrate layer that is located in between the pair of substrate layers upon which the corresponding pair of transmit coils $801\text{-}A_N$ and $801\text{-}B_N$ are respectively deposited.

Alternatively, although not explicitly shown in FIG. 8 or FIG. 9, in a multiple-receive-coil configuration example embodiment, each channel includes multiple (for example, a pair of) receive coils. For instance, a first channel includes a pair of series-connected receive coils arranged on a pair of substrate layers, respectively, both of which are located between the pair of substrate layers upon which the corresponding pair of transmit coils are respectively deposited, and so forth for other channels. In this example, the pair of receive coils which are deposited on different layers of the substrate, are coupled to one another in a series circuit by way of printed circuit board traces and a via that traverses the layers of the substrate, for instance. The antenna assembly 903, in some embodiments, is an impedance-controlled antenna assembly, for instance including outer layers 904 and 905 that each include traces and/or components configured to control an impedance of the antenna assembly.

As mentioned above, in various example embodiments, each receive coil 803 is implemented as a single receive coil or as a set of multiple receive coils, such as a pair of two receive coils coupled to one another in a series circuit topology. In some examples, different receive coil configurations are used to calibrate receive channels configured for different types of sensors, respectively. For instance, a receive coil configuration that includes a single receive coil (a single-receive-coil configuration) is used to calibrate a receive channel or port that, after calibration, is intended to be coupled to an EWC that includes a single coil. Alternatively, a receive coil configuration that includes multiple receive coils (a multiple-receive-coil configuration) is used to calibrate a receive channel or port that, after calibration, is intended to be coupled to a sensor, such as an LG or a PST, that includes multiple-coil assemblies, such as a pair of series-connected coils. In some example embodiments, at least one of the connectors 804 (for example, 804$_1$) is coupled to one of the receive coils 803$_1$ through 803$_N$ and is useable for single-receive-coil calibration, and at least another one of the connectors 804 (for example, 804$_N$) is coupled to a set of multiple receive coils (for instance, a series-connected pair of receive coils each deposited on a respective one of the layers of the substrate, not shown in FIG. 9) and is usable for multiple-receive-coil calibration. Thus, by way of the different connectors 804$_1$ through 804$_N$, the antenna assembly 903 facilitates calibration of receive channels that employ different receive coil configurations.

In some example aspects, the system for calibrating the electromagnetic navigation system includes a computing device, such as the computing device 120 and/or the computing device 1300 described herein, which in turn includes a processor (for example processor 124 or 1304) and a memory (for example, memory 126 or 1302) coupled to the plurality of pairs of transmit coils 801 by way of the plurality of input terminals 802, respectively, and coupled to the plurality of receive coils 803 by way of the plurality of output terminals 804, respectively. The memory may include instructions (for example, including the data 1314 and/or the application 1316) that, when executed by the processor, cause the processor to perform the calibration procedure 200 described herein. The memory may further includes instructions that, when executed by the processor, cause the processor to synchronously transmit and receive one or more electromagnetic signal(s).

Figure 10:
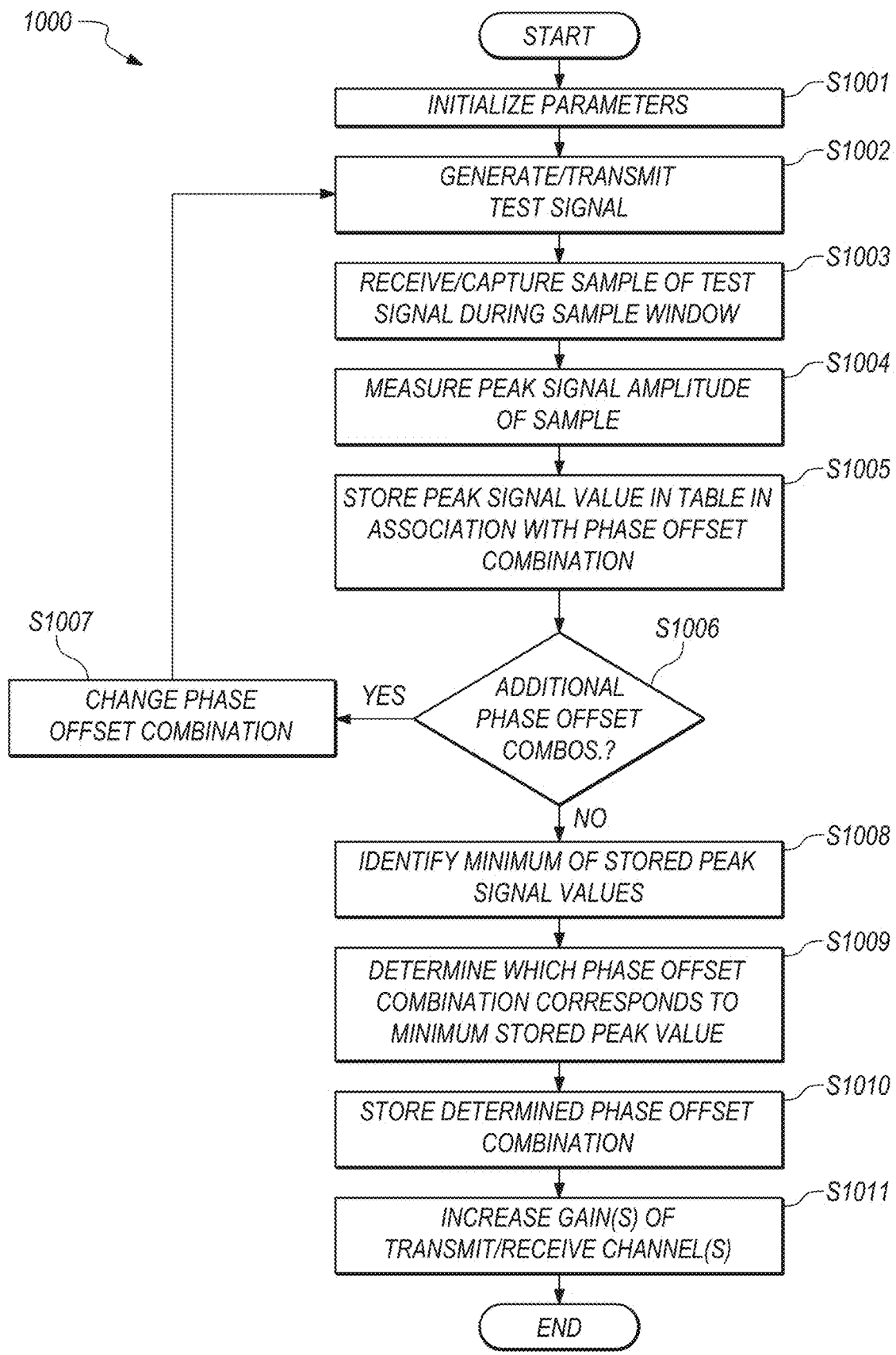
FIG. 10 is a flowchart illustrating an example procedure for optimizing an electromagnetic navigation system, in accordance with the present disclosure.

FIG. 10 is a flowchart illustrating an example procedure 1000 for optimizing an electromagnetic navigation system, in accordance with the present disclosure. In general, as described in further detail below, the procedure 1000 may be employed to determine, for a particular frequency division multiplexed signal having multiple frequency components, a combination of respective phase offsets for the frequency components (which may be referred to as an optimized combination of phase offsets) that, when the frequency components are superimposed, would yield a peak amplitude that is lower than an amplitude that would result without utilizing such phase offsets. Employing, in an electromagnetic navigation system, the phase offset combination identified by way of the procedure 1000 mitigates saturation of the ADC(s) of the system, and further enables transmit and/or receive channel gains to be increased, thereby increasing signal-to-noise ratio (SNR) and/or maximizing utilization of the dynamic range available from the ADC(s). As described below, in some example embodiments the procedure 1000 includes generating test signals and radiating or transmitting those test signals by way of an antenna, such as the antenna assembly 145 or the antenna assembly 903, and receiving and measuring samples of the transmitted test signals to determine optimal phase offsets. In other example embodiments, in lieu of radiating phase shifted waveforms using an antenna, one or more steps of the procedure 1000 are implemented by a computer (for example, by retrieving, via a processor, instructions stored in a memory and executing those instructions) to generate simulated waveforms with various phase offsets, thereby reducing the time required to determine optimal phase offsets.

Referring now to FIG. 10, at S1001, various parameters, such as for example a frequency index, a channel index, and/or other parameters, are initialized. In one example, the initialization of parameters at S1001 facilitates repetition of steps of the procedure 1000 for multiple frequencies, channels, and/or combinations of phase offset values. For instance, at S1001 a frequency index may be initialized to an initial value (e.g., 1) and a phase offset combination may be initialized to an initial value (e.g., corresponding to a phase offset combination where each phase offset equals zero).

At S1002, a frequency multiplexed electromagnetic test signal is generated, including multiple frequency components that are superimposed and that have respective phase offset values of the phase offset combination initialized at S1001. The test signal is transmitted (or radiated) by way of a transmitting antenna, such as the antenna assembly 145 or the antenna assembly 903, or is generated within a simulation environment as described above.

At S1003, the test signal radiated at S1002 is received by way of a receiving antenna, and a sample of the received test signal is captured during a sampling window. As described in further detail below, FIG. 11 illustrates example electromagnetic signal waveforms that may be captured at S1003.

At S1004, a peak signal amplitude of the captured sample is measured. At S1005, the peak signal amplitude measured at S1004 is stored in a table in association with the respective combination of phase offset values used at S1002 to generate the signal.

At S1006, a determination is made as to whether steps of the procedure 1000 are to be repeated for an additional phase offset combination for the frequency components. In one example, steps of the procedure 1000 are repeated for each possible combination of phase offset values ranging from zero to a maximum value (e.g., 2π radians or 360°) in increments of a phase offset step size. In such an example, the determination at S1006 of whether steps of the procedure 1000 are to be repeated is made based on whether the table populated at S1005 includes peak signal amplitude values for all possible combinations of phase offset values for the frequency components of the signal generated at S1002 given the particular phase offset step size. If the table populated at S1005 does not include peak signal amplitude values for all possible combinations of phase offset values for the frequency components of the signal generated at S1002 given the particular phase offset step size, then it is determined at S1006 that steps of the procedure 1000 are to be repeated for an additional phase offset combination ("YES" at S1006).

At S1007, the additional phase offset combination is set and the procedures of S1002 through S1006 are repeated based on the additional phase offset combination. In this manner, the table may be populated at S1005 for each possible combination of phase offset values for the frequency components, respectively, given the phase offset step size. In one example, the set of possible combinations of phase offset values is generated based on the frequency components of the signal and the phase offset step size. In particular, each of the combinations of phase offset values includes a respective set of phase offset values that correspond to the frequency components, respectively. Each of the phase offset values may have a value in a range from zero to a maximum value (e.g., 2π radians or 360°), in increments of the phase offset step size. For example, if the phase offset step size were 90°, the possible phase offset values for each frequency component would be 0°, 90°, 180°, and 270°. In this example, the number of possible phase offset values $N_\theta$ for a particular frequency component would be 4. Thus, for a frequency multiplexed signal having a particular number of frequencies components $N_F$, with each frequency component having a number of possible phase offset values $N_\theta$, the total number of possible combinations of phase offsets $N_C$ is computed according to the equation:

$$N_C = N_\theta^{N_F} \quad (9)$$

If, on the other hand, the table populated at S1005 includes peak signal amplitude values for all possible combinations of phase offset values for the frequency components of the signal generated at S1002 given the particular phase offset step size, then it is determined at S1006 that steps of the procedure 1000 are not to be repeated for an additional phase offset combination ("NO at S1006").

At S1008, a minimum value among the peak signal amplitudes stored at S1005 in the completed table is identified. At S1009, based on the table, a determination is made as to which one of the plurality of combinations of phase offset values in the table is associated with the minimum value of the stored peak signal amplitudes identified at S1008.

At S1010, the combination of phase offset values determined at S1009 is stored in a table, for example in a memory, for use during an electromagnetic navigation procedure in generating an electromagnetic signal that includes the plurality of frequency components having the determined combination of phase offset values, respectively. Table 2 below illustrates an example of a table that may be populated with the combination of phase offset values $\theta_{off}$ for the frequency components stored at S1010, for an example system having 9 frequencies or channels.

TABLE 2

| Frequency/Channel Index | Frequency (Hz) | $\theta_{off}$ (radians or degrees) |
|---|---|---|
| 1 | $F_1$ | $\theta_{off1}$ |
| 2 | $F_2$ | $\theta_{off2}$ |
| 3 | $F_3$ | $\theta_{off3}$ |
| 4 | $F_4$ | $\theta_{off4}$ |
| 5 | $F_5$ | $\theta_{off5}$ |
| 6 | $F_6$ | $\theta_{off6}$ |
| 7 | $F_7$ | $\theta_{off7}$ |
| 8 | $F_8$ | $\theta_{off8}$ |
| 9 | $F_9$ | $\theta_{off9}$ |

At S1011, gain values of one or more transmit and/or receive amplifiers in the electromagnetic navigation system may be increased. during the electromagnetic navigation procedure: generating a second signal including the plurality of frequency components having the determined combination of phase offset values, respectively; amplifying the second signal so as to have a magnitude greater than a magnitude of the test signal; and transmitting the second signal. 23. The method of claim 20, further comprising: during the electromagnetic navigation procedure: receiving a second signal that includes the plurality of frequency components having the determined combination of phase offset values, respectively; and amplifying the second signal so as to have a magnitude greater than a magnitude of the test signal.

Figure 11A:
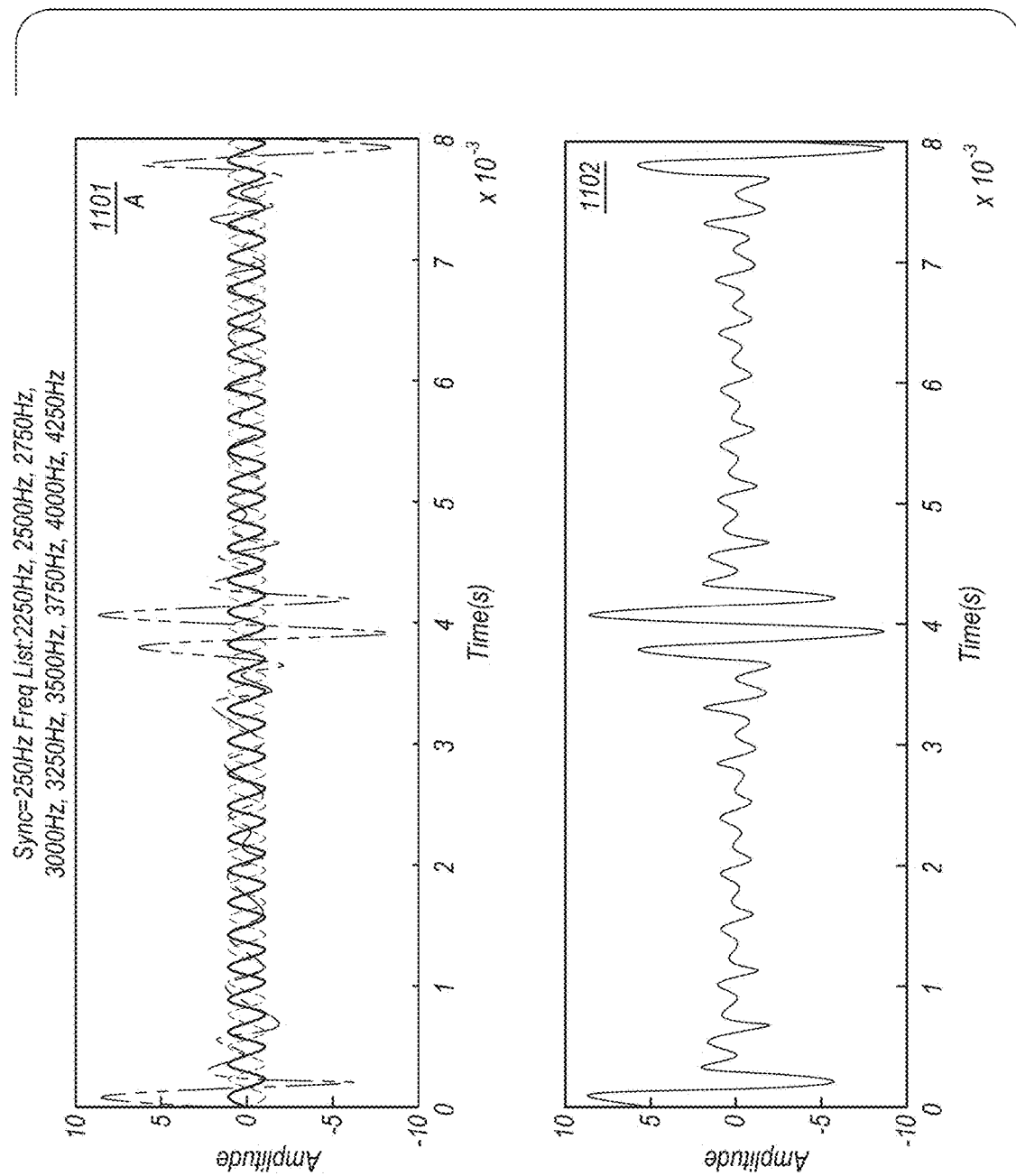
FIG. 11A and FIG. 11B (collectively, FIG. 11) illustrate example electromagnetic signal waveforms before and after optimization, in accordance with the present disclosure.
Figure 11B:
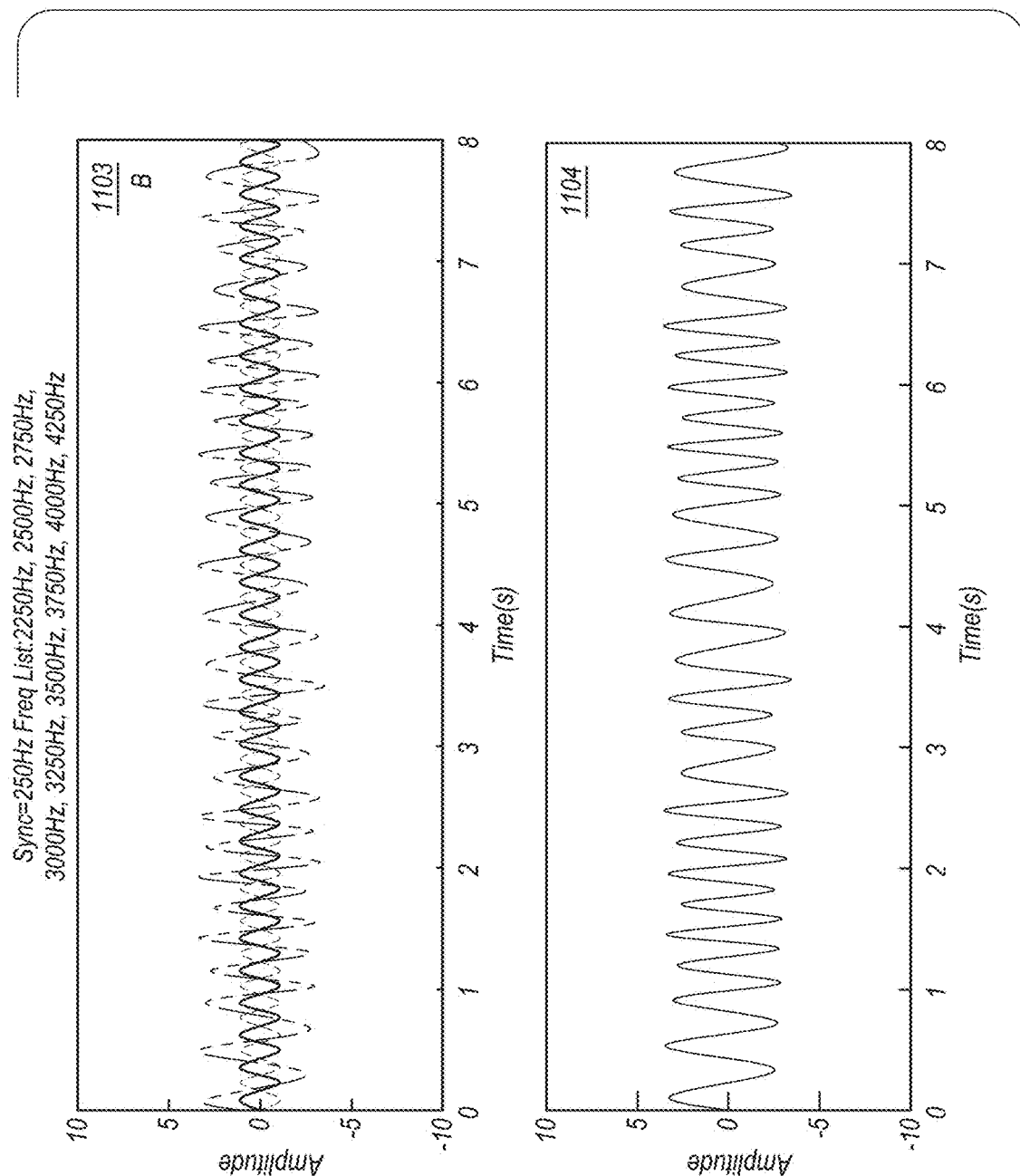

FIG. 11A and FIG. 11B (collectively, FIG. 11) illustrate example electromagnetic signal waveforms before and after optimization according to the procedure 1000, in accordance with the present disclosure. In particular, the signal waveform 1101 of FIG. 11A shows multiple separate frequency components that may be generated at S1002 without employing the combination of phase offset values determined at S1009 (for example, employing phase offset values of zero for each of the frequency components). The signal waveform 1102 of FIG. 11A represents a combination of the multiple frequency components of the waveform 1101 superimposed upon one another. The superimposed waveform 1102 has a relatively high peak amplitude that may saturate an ADC and/or make limited use of the dynamic range available from an ADC.

The signal waveform 1103 of FIG. 11B shows multiple separate frequency components that may be generated at S1002 employing the combination of phase offset values determined at S1009. The signal waveform 1104 of FIG. 11B represents a combination of the multiple frequency components of the waveform 1103 superimposed upon one another. The superimposed waveform 1104 has a peak amplitude that is lower than that of the superimposed waveform 1102, and may thus mitigate or avoid saturation of the ADC and/or make more effective use of the dynamic range available from an ADC, for example, by enabling one or more gains of the transmit and/or receive channel to be increased as described above in connection with S1011.

Figure 12A:
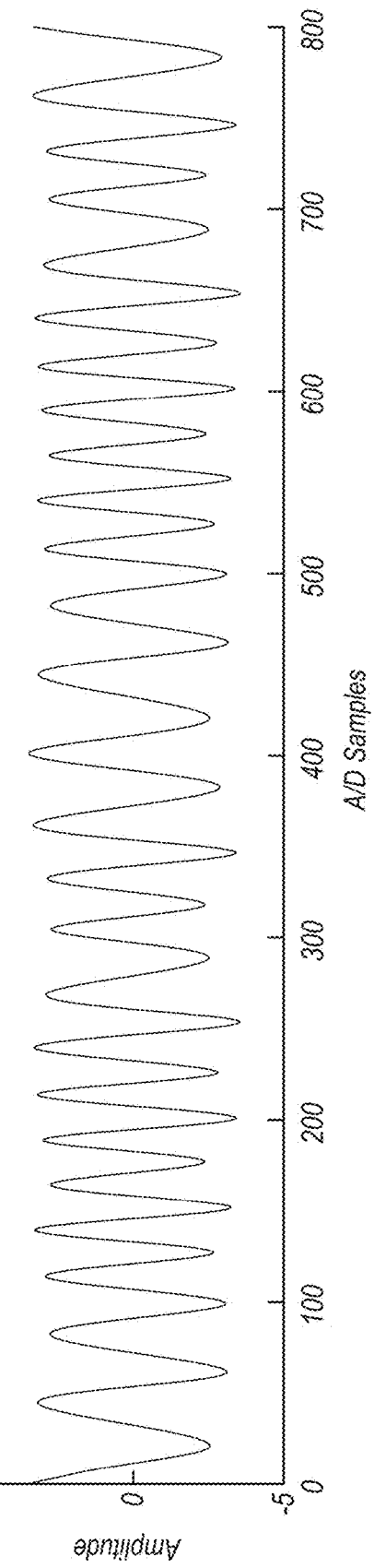
FIG. 12A, FIG. 12B, and FIG. 12C (collectively, FIG. 12) illustrate an example frequency multiplexed electromagnetic signal, and results of applying a filter and an FFT to the signal in an optimized electromagnetic navigation system, in accordance with the present disclosure.
Figure 12B:
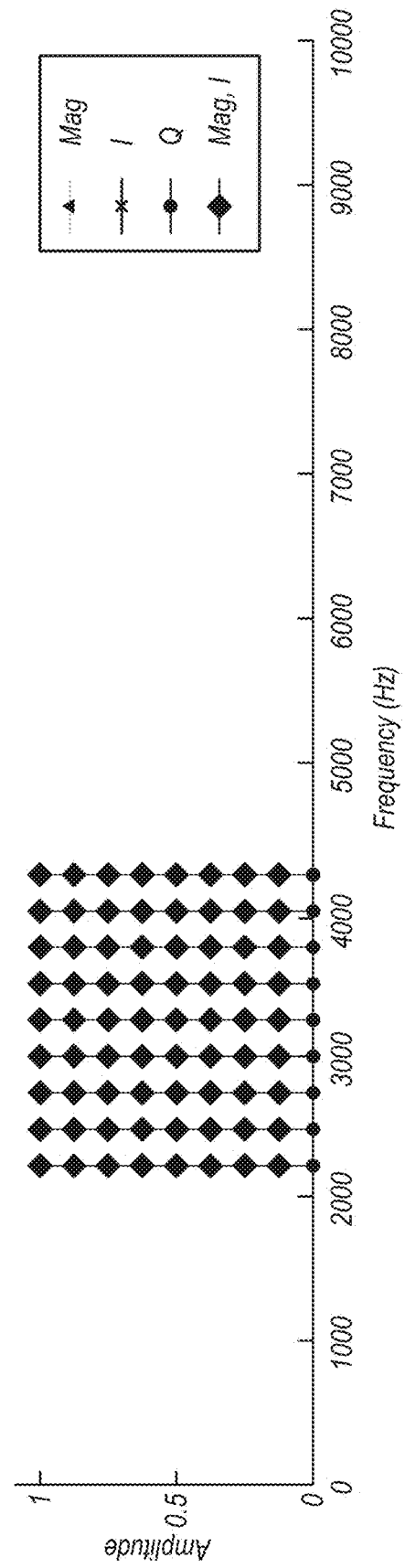
Figure 12C:
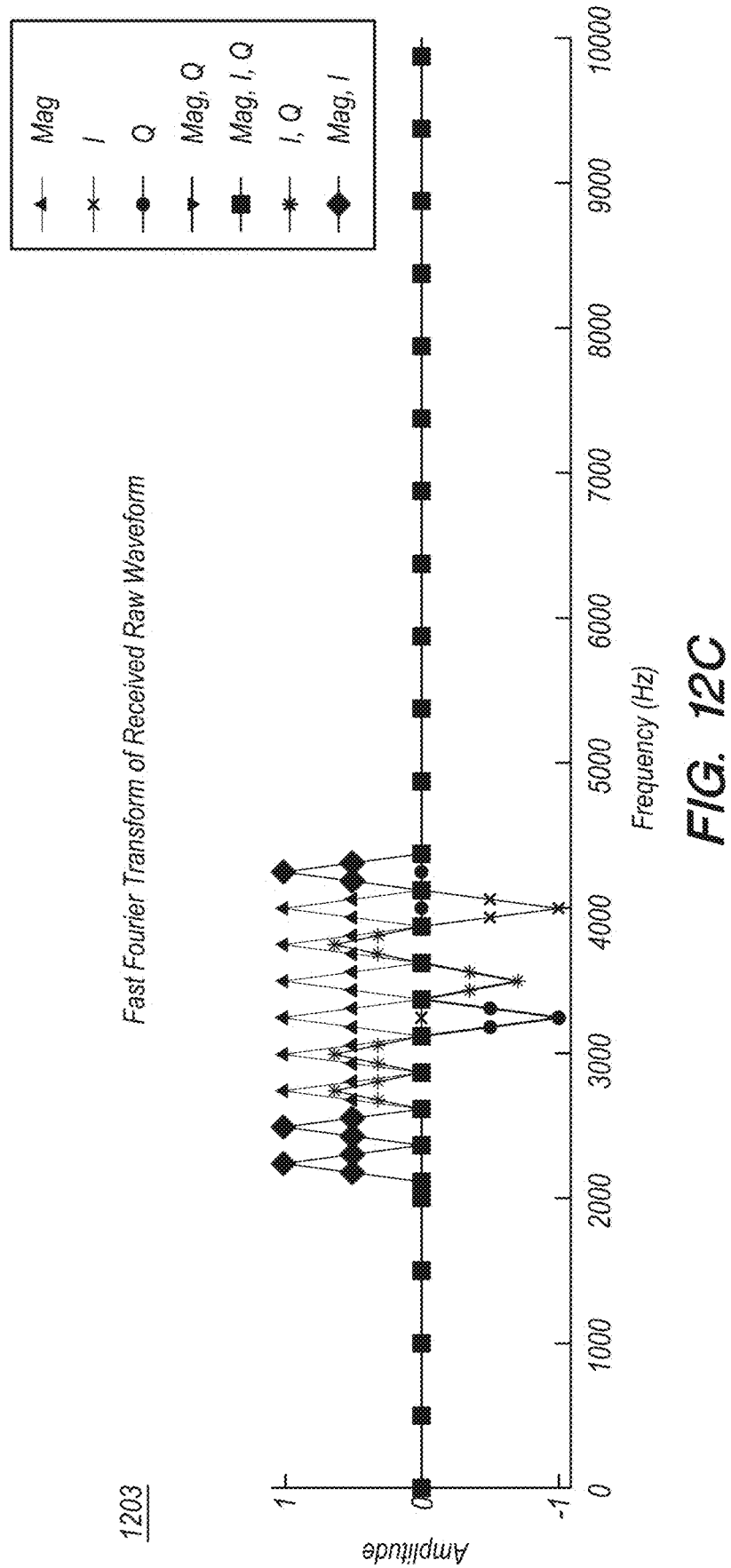

FIG. 12A, FIG. 12B, and FIG. 12C (collectively, FIG. 12) illustrate an example frequency multiplexed electromagnetic signal, and results of applying a filter and an FFT to the signal in an optimized electromagnetic navigation system (for instance an electromagnetic navigation system optimized according to the procedure 1000 herein), in accordance with the present disclosure. In particular, the waveform 1201 of FIG. 12A is generated using the same frequency components used to generate the waveform 600 of FIG. 6, except using the combination of phase offsets determined at S1009. Graph 1202 of FIG. 12B illustrates the in-phase (I) components and quadrature (Q) components that are computed based on the signal shown in graph 1201 after the signal has been filtered. Graph 1203 of FIG. 12C illustrates a result of applying an FFT to the signal shown in graph 1201. The in-phase (I) components and quadrature (Q) components that are computed based on the signal shown in graph 1201 after the signal has been filtered are the same as those in the graph 701 of FIG. 7, illustrating that, in one example embodiment, advantages of calibration and optimization may both be realized in a system that has been both calibrated according to the procedure 200 and optimized according to the procedure 1000.

Figure 2:
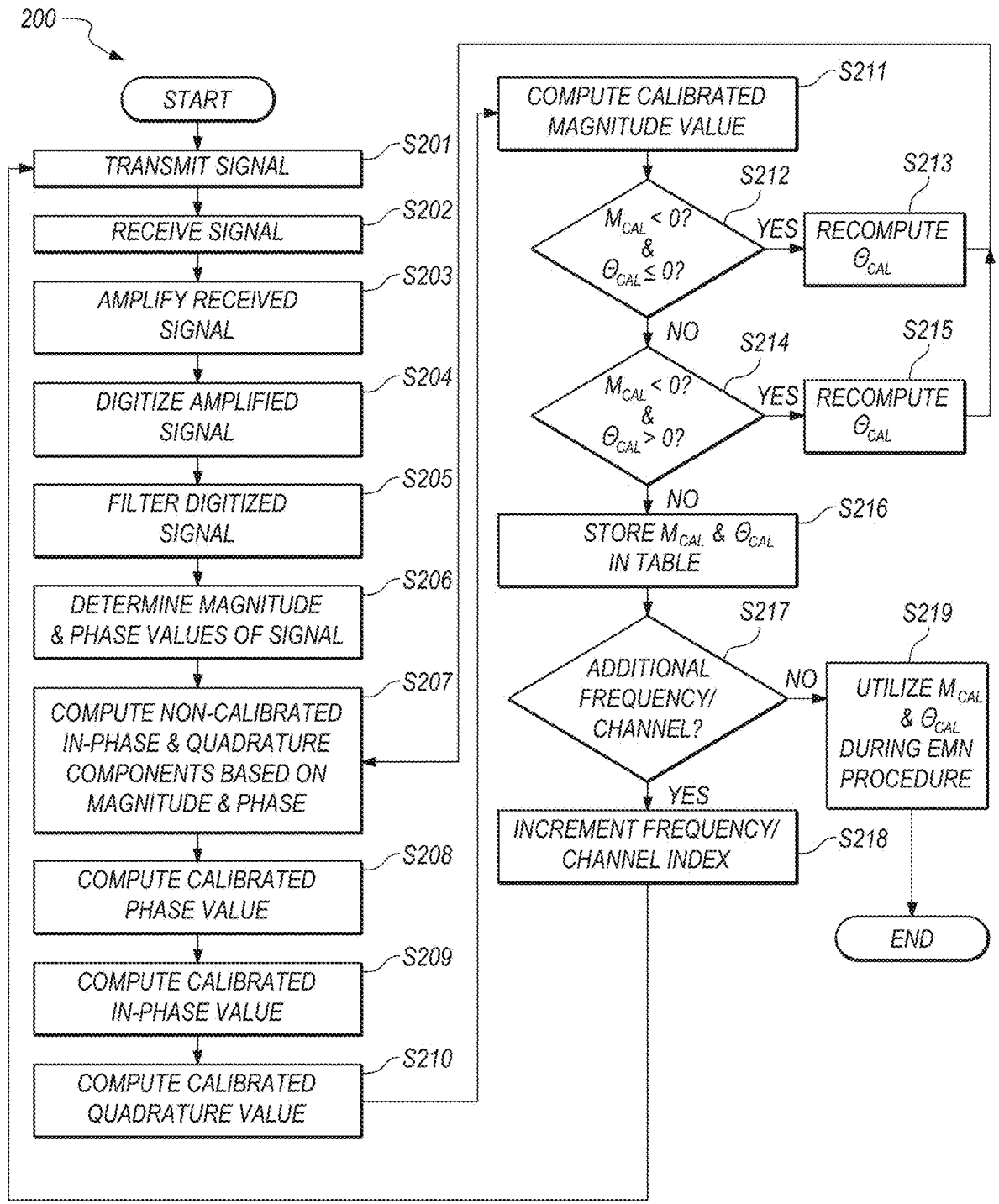
FIG. 2 is a flowchart illustrating an example procedure for calibrating an electromagnetic navigation system, in accordance with the present disclosure.
Figure 13:
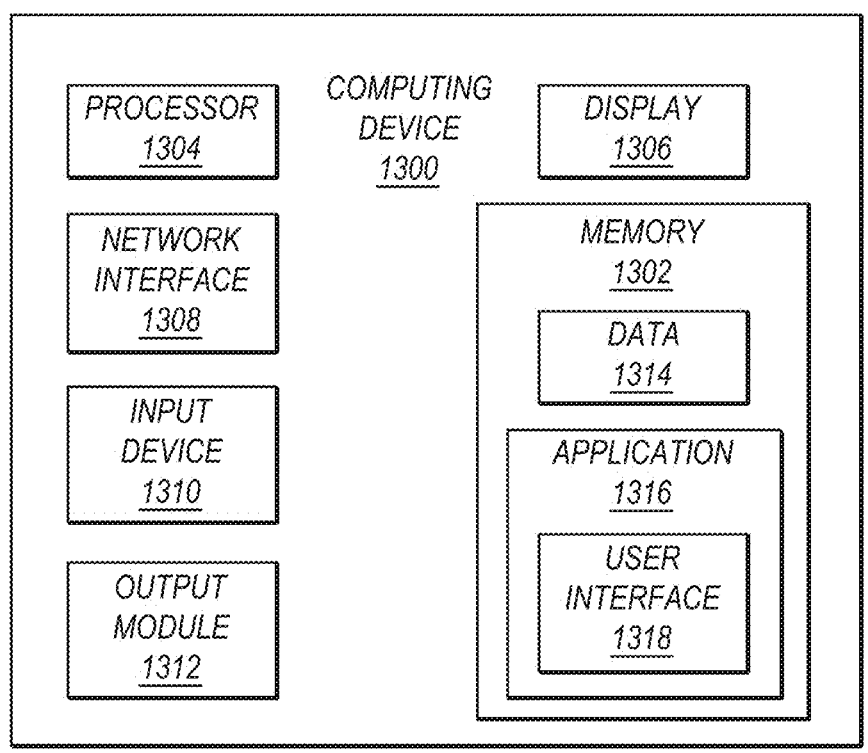
FIG. 13 is a block diagram of an example computing device for use in various embodiments of the present disclosure.

Turning now to FIG. 13, there is shown a block diagram of a computing device 1300, which can be used as the EMN system 100, the computing device 120, the tracking device 160, and/or a computer performing any of the procedures herein, such as for example the procedures 200 and/or 1000 described herein in connection with FIG. 2 and/or FIG. 10, respectively. The computing device 1300 may include one or more of each of the following components: a memory 1302, a processor 1304, a display 1306, a network interface controller 1308, an input device 1310, and/or an output module 1312.

The memory 1302 includes any non-transitory computer-readable storage media for storing data and/or software that is executable by the processor 1304 and which controls the operation of the computing device 1300. In an embodiment, the memory 1302 may include one or more solid-state storage devices such as flash memory chips. Alternatively, or in addition to the one or more solid-state storage devices, the memory 1302 may include one or more mass storage devices connected to the processor 1304 through a mass storage controller (not shown in FIG. 13) and a communications bus (not shown in FIG. 13). Although the description of computer-readable media contained herein refers to a solid-state storage, it should be appreciated by those skilled in the art that computer-readable storage media can be any available media that can be accessed by the processor 1304. That is, computer readable storage media include non-transitory, volatile and non-volatile, removable and non-removable media implemented in any method or technology for storage of information such as computer-readable instructions, data structures, program modules or other data. For example, computer-readable storage media include RAM, ROM, EPROM, EEPROM, flash memory or other solid state memory technology, CD-ROM, DVD, Blu-Ray or other optical storage, magnetic cassettes, magnetic tape, magnetic disk storage or other magnetic storage devices, or any other medium which can be used to store the desired information and which can be accessed by the computing device 1300.

The memory 1302 may store application 1316 and/or data 1314. The application 1316 may, when executed by the processor 1304, cause the display 1306 to present user interface 1318 on the display 1306.

The processor 1304 may be a general purpose processor, a specialized graphic processing unit (GPU) configured to perform specific graphics processing tasks while freeing up the general purpose processor to perform other tasks, a programmable logic device such as a field programmable gate array (FPGA) or complex programmable logic device (CPLD), and/or any number or combination of such processors or devices configured to work independently or cooperatively.

The display 1306 may be touch-sensitive and/or voice-activated, enabling the display 1306 to serve as both an input and output device. Alternatively, a keyboard (not shown), mouse (not shown), or other data input devices may be employed.

The network interface 1308 may be configured to connect to a network, such as a local area network (LAN) including a wired network and/or a wireless network, a wide area network (WAN), a wireless mobile network, a Bluetooth network, and/or the Internet. The computing device 1300 may receive updates to its software, for example, application 1316, via the network interface controller 1308. The computing device 1300 may also display notifications on the display 1306 that a software update is available.

In another aspect, the computing device 1300 may receive computed tomographic (CT) image data of a patient from a server, for example, a hospital server, Internet server, or other similar servers, for use during surgical planning. Patient CT image data may also be provided to the computing device 1300 via a removable memory (not shown in FIG. 13).

Input device 1310 may be any device by means of which a user may interact with the computing device 1300, such as, for example, a mouse, keyboard, foot pedal, touch screen, and/or voice interface.

Output module 1312 may include any connectivity port or bus, such as, for example, parallel ports, serial ports, universal serial busses (USB), or any other similar connectivity port known to those skilled in the art.

The application 1316 may be one or more software programs stored in the memory 1302 and executed by the processor 1304 of the computing device 1300. One or more software programs in the application 1316 may be loaded from the memory 1302 and executed by the processor 1304 to perform any of the procedures herein, such as for example the procedures 200 and/or 1000 described herein in connection with FIG. 2 and/or FIG. 10, respectively.

The application 1316 may be installed directly on the computing device 1300, or may be installed on another computer, for example a central server, and opened on the computing device 1300 via the network interface 1308. Application 1316 may run natively on the computing device 1300, as a web-based application, or any other format known to those skilled in the art. In some embodiments, the application 1316 will be a single software program having all of the features and functionality described in the present disclosure. In other embodiments, the application 1316 may be two or more distinct software programs providing various parts of these features and functionality. For example, the application 1316 may include one software program for automatically designing loop antennas, another one for converting the design into a CAD file, and a third program for PCB layout software program. In such instances, the various software programs forming part of the application 1316 may be enabled to communicate with each other and/or import and export various data including settings and parameters relating to the design of the loop antennas. For example, a design of a loop antenna generated by one software program may be stored and exported to be used by a second software program to convert into a CAD file, and the converted file may be also stored and exported to be used by a PCB layout software program to complete a blueprint of the loop antenna.

The application 1316 may communicate with a user interface 1318 which generates a user interface for presenting visual interactive features to a user, for example, on the display 1306 and for receiving input, for example, via a user input device. For example, user interface 1318 may generate a graphical user interface (GUI) and output the GUI to the display 1306 for viewing by a user.

In a case where the computing device 1300 is used as the EMN system 100, the computing device 120, or the tracking device 160, the computing device 1300 may be linked to the monitoring device 130, thus enabling the computing device 1300 to control the output on the monitoring device 130 along with the output on the display 1306. The computing device 1300 may control the monitoring device 130 to display output which is the same as or similar to the output displayed on the display 1306. For example, the output on the display 1306 may be mirrored on the monitoring device 130. Alternatively, the computing device 1300 may control the monitoring device 130 to display different output from that displayed on the display 1306. For example, the monitoring device 130 may be controlled to display guidance images and information during the surgical procedure, while the display 1306 is controlled to display other output, such as configuration or status information of an electrosurgical generator (not shown in FIG. 1).

The application 1316 may include one software program for use during the planning phase, a second software program for use during the navigation or procedural phase, and/or other application(s) for other phases, such as a calibration phase, an optimization phase, and/or or the like. In such instances, the various software programs forming part of application 1316 may be enabled to communicate with each other and/or import and export various settings and parameters relating to the navigation and treatment and/or the patient to share information. For example, a treatment plan and any of its components generated by one software program during the planning phase may be stored and exported to be used by a second software program during the procedure phase.

Although embodiments have been described in detail with reference to the accompanying drawings for the purpose of illustration and description, it is to be understood that the inventive processes and apparatus are not to be construed as limited. It will be apparent to those of ordinary skill in the art that various modifications to the foregoing embodiments may be made without departing from the scope of the disclosure. For example, various steps of the procedures described herein may be implemented concurrently and/or in an order different from the example order(s) described herein.

What is claimed is:

1. A method for calibrating an electromagnetic navigation system configured to identify a location of a medical device in an electromagnetic field and including a transmitting antenna and a receiving antenna, the method comprising:
   transmitting, via the transmitting antenna, an electromagnetic signal;
   receiving, via the receiving antenna positioned at a location, the electromagnetic signal transmitted directly from the transmitting antenna;
   measuring a non-calibrated in-phase component and a non-calibrated quadrature component based on a first magnitude value and a first phase value of the received electromagnetic signal, wherein the non-calibrated in-phase component is a signal component of the received electromagnetic signal and the non-calibrated quadrature component is a noise component of the received electromagnetic signal;
   computing a second phase value based on the non-calibrated in-phase component and the non-calibrated quadrature component;
   computing a calibrated in-phase component based on the second phase value, the non-calibrated in-phase component, and the non-calibrated quadrature component;
   computing a calibrated quadrature component based on the second phase value, the non-calibrated in-phase component, and the non-calibrated quadrature component;
   computing a second magnitude value based on the calibrated in-phase component; and
   storing the second phase value and the second magnitude value with the location of the receiving antenna in a table in a memory of the electromagnetic navigation system for identifying a location of a medical device used during an electromagnetic navigation procedure, wherein the transmitting and receiving of the electromagnetic signal are synchronized to one another.

2. The method of claim 1, further comprising:
   performing a lookup in at least one of a sine table or a cosine table based on the first magnitude value and the first phase value, wherein the computing of at least one of the non-calibrated in-phase component or the non-calibrated quadrature component is further based on a result of the performing of the lookup.

3. The method of claim 1, wherein the second phase value is computed according to the equation:

$$\theta_{cal} = \tan^{-1}\left(\frac{Q_{non-calibrated}}{I_{non-calibrated}}\right),$$

where $\theta_{cal}$ represents the second phase value between $Q_{non-calibrated}$ and $I_{non-calibrated}$, $I_{non\ calibrated}$ represents the non-calibrated in-phase component, and $Q_{non-calibrated}$ represents the non-calibrated quadrature component.

4. The method of claim 1, wherein the calibrated in-phase component is computed according to the equation:

$$I_{calibrated} = I_{non-calibrated} \times \cos(\theta_{cal}) + Q_{non-calibrated} \times \sin(\theta_{cal}),$$

where $I_{calibrated}$ represents the calibrated in-phase component, $I_{non-calibrated}$ represents the non-calibrated in-phase component, $\theta_{cal}$ represents the second phase value, and $Q_{non-calibrated}$ represents the non-calibrated quadrature component.

5. The method of claim 1, wherein the calibrated quadrature component is computed according to the equation:

$$Q_{calibrated} = -I_{non-calibrated} \times \sin(\theta_{cal}) + Q_{non-calibrated} \times \cos(\theta_{cal}),$$

where $Q_{calibrated}$ represents the calibrated quadrature component, $I_{non-calibrated}$ represents the non-calibrated in-phase component, $\theta_{cal}$ represents the second phase value, and $Q_{non-calibrated}$ represents the non-calibrated quadrature component.

6. The method of claim 1, wherein the second magnitude value is computed according to the equation:

$$M_{cal} = \frac{1}{I_{calibrated}},$$

where $M_{cal}$ represents the second magnitude value and $I_{calibrated}$ represents the calibrated in-phase component.

7. The method of claim 1, further comprising:
   determining whether the second magnitude value is less than zero; and
   in response to a determination that the second magnitude value is less than zero:
      computing a third phase value, and
      recomputing the second magnitude value, the calibrated in-phase component, and the calibrated quadrature component based on the third phase value.

8. The method of claim 1, further comprising:
   determining whether the second magnitude value is less than zero and whether the second phase value is less than or equal to zero; and
   in response to a determination that the second magnitude value is less than zero and the second phase value is less than or equal to zero:
      computing a third phase value according to the equation:

$$\theta_{cal}' = \theta_{cal} + \pi,$$

where $\theta_{cal}'$ represents the third phase value and $\theta_{cal}$ represents the second phase value; and recomputing the second magnitude value, the calibrated in-phase component, and the calibrated quadrature component based on the third phase value.

9. The method of claim 1, further comprising:
determining whether the second magnitude value is less than zero and whether the second phase value is greater than zero; and
in response to a determination that the second magnitude value is less than zero and the second phase value is greater than zero:
computing a third phase value according to the equation:

$$\theta_{cal}' = \theta_{cal} - \pi,$$

where $\theta_{cal}'$ represents the third phase value and $\theta_{cal}$ represents the second phase value; and
recomputing the second magnitude value, the calibrated in-phase component, and the calibrated quadrature component based on the third phase value.

10. The method of claim 1, further comprising:
during the electromagnetic navigation procedure,
receiving a second signal having a third magnitude value and a third phase value;
computing a second non-calibrated in-phase component and a second non-calibrated quadrature component based on the third magnitude value and the third phase value; and
computing a corrected in-phase component and a corrected quadrature component based on the second phase value, the second magnitude value, the second non-calibrated in-phase component, and the second non-calibrated quadrature component.

11. The method of claim 9, wherein the corrected in-phase component is computed according to the equation:

$$I_c = M_{cal} \times ((I_{non-cal2}) \times \cos(\theta_{cal}) + (Q_{non-cal2}) \times \sin(\theta cal)),$$

and wherein the corrrected quadrature component is computed according to the equation:

$$Q_c = M_{cal} \times (-(I_{non-cal2}) \times \sin(\theta_{cal}) + (Q_{non-cal2}) \times \cos(\theta_{cal})),$$

Where $I_c$ represents the corrected in-phase component, $M_{cal}$ represents the second magnitude value, $I_{non-cal2}$ represents the second non-calibrated in-phase component, $\theta_{cal}$ represents the second phase value, $Q_{non-cal2}$ represents the second non-calibrated quadarture component, and $Q_c$ represents the corrected quadrature component.

12. A system for calibrating an electromagnetic navigation system configured to identify a location of a medical device in an electromagnetic field, the system comprising:
a transmitting antenna configured to transmit an electromagnetic signal;
a receiving antenna positioned at a location and configured to receive the electromagnetic signal transmitted directly from the transmitting antenna;
a processor; and
a memory including instructions that, when executed by the processor, cause the processor to:
measure a non-calibrated in-phase component and a non-calibrated quadrature component based on a first magnitude value and a first phase value of the received electromagnetic signal, wherein the non-calibrated in-phase component is a signal component of the received electromagnetic signal and the non-calibrated quadrature component is a noise component of the received electromagnetic signal;
compute a second phase value based on the non-calibrated in-phase component and the non-calibrated quadrature component;
compute a calibrated in-phase component based on the second phase value, the non-calibrated in-phase component, and the non-calibrated quadrature component;
compute a calibrated quadrature component based on the second phase value, the non-calibrated in-phase component, and the non-calibrated quadrature component;
compute a second magnitude value based on the calibrated in-phase component; and
store, in the memory, the second phase value and the second magnitude value with the location of the receiving antenna in a table for identifying a location of a medical device used during an electromagnetic navigation procedure,
wherein the transmitting and receiving of the electromagnetic signal are synchronized to one another.

13. The system of claim 11, wherein the memory further stores instructions that, when executed by the processor, cause the processor to compute the second phase value according to the equation:

$$\theta_{cal} = \tan^{-1}\left(\frac{Q_{non-calibrated}}{I_{non-calibrated}}\right),$$

Where $\theta_{cal}$ represents the second phase between $Q_{non-calibrated}$ and $I_{non-calibrated}$, $Q_{non-calibrated}$ and represents the non-calibrated quadrature component, and $I_{non-calibrated}$ represents the non-calibrated in-phase component.

14. The system of claim 11, wherein the memory further stores instructions that, when executed by the processor, cause the processor to compute the calibrated in-phase component according to the equation:

$$I_{calibrated} = I_{non-calibrated} \times \cos(\theta_{cal}) + Q_{non-calibrated} \times \sin(\theta_{cal}),$$

where $I_{calibrated}$ represents the calibrated in-phase component, $I_{non-calibrated}$ represents the non-calibrated in-phase component, $\theta_{cal}$ represents the second phase value, and $Q_{non-calibrated}$ represents the non-calibrated quadrature component.

15. The system of claim 11, wherein the memory further stores instructions that, when executed by the processor, cause the processor to compute the calibrated quadrature component according to the equation:

$$Q_{calibrated} = -I_{non-calibrated} \times \sin(\theta_{cal}) + Q_{non-calibrated} \times \cos(\theta_{cal}),$$

where $Q_{calibrated}$ represents the calibrated quadrature component, $I_{non-calibrated}$ represents the non-calibrated in-phase, $\theta_{cal}$ represents the second phase value, and $Q_{non-calibrated}$ represents the non-calibrated quadrature component.

16. The system of claim 11, wherein the memory further stores instructions that, when executed by the processor, cause the processor to compute the second magnitude value according to the equation:

$$M_{cal} = \frac{1}{I_{calibrated}},$$

where $M_{cal}$ represents the second magnitude value and $I_{calibrated}$ represents the calibrated in-phase component.

17. The system of claim 11, wherein the memory further stores instructions that, when executed by the processor, cause the processor to:
   determine whether the second magnitude value is less than zero; and
   in response to a determination that the second magnitude value is less than zero:
   compute a third phase value, and
   recompute the second magnitude value, the calibrated in-phase component, and the calibrated quadrature component based on the third phase value.

18. The system of claim 11, wherein the memory further stores instructions that, when executed by the processor, cause the processor to:
   during the electromagnetic navigation procedure,
   receive a second signal having a third magnitude value and a third phase value;
   compute a second non-calibrated in-phase component and a second non-calibrated quadrature component based on the third magnitude value and the third phase value; and
   compute a corrected in-phase component and a corrected quadrature component based on the second phase value, the second magnitude value, the second non-calibrated in-phase component, and the second non-calibrated quadrature component.

19. A non-transitory computer-readable medium having stored thereon sequences of instructions that, when executed by an electromagnetic navigation system configured to identify a location of a medical device in an electromagnetic field and including a transmitting antenna and a receiving antenna, cause the electromagnetic navigation system to:
   transmit, via the transmitting antenna, an electromagnetic signal;
   receive, via the receiving antenna positioned at a location, the electromagnetic signal transmitted directly from the transmitting antenna;
   measure a non-calibrated in-phase component and a non-calibrated quadrature component based on a first magnitude value and a first phase value of the received electromagnetic signal, wherein the non-calibrated in-phase component is a signal component of the received electromagnetic signal and the non-calibrated quadrature component is a noise component of the received electromagnetic signal;
   compute a second phase value based on the non-calibrated in-phase component and the non-calibrated quadrature component;
   compute a calibrated in-phase component based on the second phase value, the non-calibrated in-phase component, and the non-calibrated quadrature component;
   compute a calibrated quadrature component based on the second phase value, the non-calibrated in-phase component, and the non-calibrated quadrature component;
   compute a calibrated magnitude value based on the calibrated in-phase component; and
   store the second phase value and the calibrated magnitude value with the location of the receiving antenna in a table for identifying a location of a medical device used during an electromagnetic navigation procedure,
   wherein the transmitting and receiving of the electromagnetic signal are synchronized to one another.

* * * * *